US008895583B2

(12) United States Patent
Tan et al.

(10) Patent No.: US 8,895,583 B2
(45) Date of Patent: Nov. 25, 2014

(54) SOLUBLE GUANYLATE CYCLASE ACTIVATORS

(75) Inventors: John Q. Tan, Westfield, NJ (US); Ronald M. Kim, Summit, NJ (US); John W. Mirc, Tokyo (JP)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/881,029

(22) PCT Filed: Oct. 24, 2011

(86) PCT No.: PCT/US2011/057419
§ 371 (c)(1),
(2), (4) Date: Apr. 23, 2013

(87) PCT Pub. No.: WO2012/058132
PCT Pub. Date: May 3, 2012

(65) Prior Publication Data
US 2013/0210798 A1  Aug. 15, 2013

Related U.S. Application Data

(60) Provisional application No. 61/407,712, filed on Oct. 28, 2010.

(51) Int. Cl.
| | |
|---|---|
| A61K 31/4439 | (2006.01) |
| C07D 401/14 | (2006.01) |
| A61K 45/06 | (2006.01) |
| C07D 213/72 | (2006.01) |
| A61K 31/496 | (2006.01) |
| C07D 401/04 | (2006.01) |
| A61K 31/4545 | (2006.01) |

(52) U.S. Cl.
CPC .............. *C07D 401/14* (2013.01); *A61K 45/06* (2013.01); *C07D 213/72* (2013.01); *A61K 31/4439* (2013.01); *A61K 31/496* (2013.01); *C07D 401/04* (2013.01); *A61K 31/4545* (2013.01)
USPC .......................................... 514/318; 546/194

(58) Field of Classification Search
CPC .......................... A61K 31/4439; C07D 401/14
USPC .......................................... 546/194; 514/318
See application file for complete search history.

(56) References Cited

U.S. PATENT DOCUMENTS

| | | | |
|---|---|---|---|
| 6,162,819 A | 12/2000 | Schindler et al. |
| 6,166,027 A | 12/2000 | Straub et al. |
| 6,743,798 B1 | 6/2004 | Straub et al. |
| 6,903,089 B1 | 6/2005 | Stasch et al. |
| 7,115,599 B2 | 10/2006 | Stasch et al. |
| 7,173,037 B2 | 2/2007 | Alonso-Alija et al. |
| 7,666,867 B2 | 2/2010 | Makriyannis et al. |
| 8,114,400 B2 | 2/2012 | Schirok et al. |
| 8,222,262 B2 | 7/2012 | Eriksen et al. |
| 8,309,551 B2 | 11/2012 | Schirok et al. |
| 2004/0048866 A1 | 3/2004 | Kolasa et al. |
| 2008/0188666 A1 | 8/2008 | Berger et al. |
| 2010/0029653 A1 | 2/2010 | Schirok et al. |
| 2010/0216764 A1 | 8/2010 | Kim et al. |
| 2011/0130445 A1 | 6/2011 | Lampe et al. |
| 2012/0022084 A1 | 1/2012 | Follmann et al. |
| 2012/0029002 A1 | 2/2012 | Straub et al. |

FOREIGN PATENT DOCUMENTS

| | | | |
|---|---|---|---|
| WO | WO2004/092140 A1 | 10/2004 |
| WO | WO2009/032249 A1 | 12/2009 |
| WO | WO2010/065275 A1 | 6/2010 |
| WO | WO2011/019518 A1 | 2/2011 |

OTHER PUBLICATIONS

PCT Search Report for PCT/US2011/057419 mailed on Mar. 23, 2012, 2 pages.
PCT Written Opinion for PCT/US2011/057419 completed on Feb. 15, 2012; 4 pages.
U.S. Appl. No. 13/704,980.
U.S. Appl. No. 13/806,425.
Writen Opinion of PCT/US2011/057419 filed on Oct. 24, 2011; completed on Feb. 15, 2013; 4 pages.

*Primary Examiner* — Patricia L Morris
(74) *Attorney, Agent, or Firm* — Kenrick L. Vidale; Anna L. Cocuzzo

(57) ABSTRACT

This inventions relates to compounds having the structure Formula I and pharmaceutically acceptable salts thereof which are soluble guanylate cyclase activators. The compounds are useful for treatment or prevention of cardiovascular diseases, endothelial dysfunction, diastolic dysfunction, atherosclerosis, hypertension, pulmonary hypertension, angina pectoris, thromboses, restenosis, myocardial infarction, strokes, cardiac insufficiency, pulmonary hypertonia, erectile dysfunction, asthma bronchiale, chronic kidney insufficiency, diabetes, or cirrhosis of the liver.

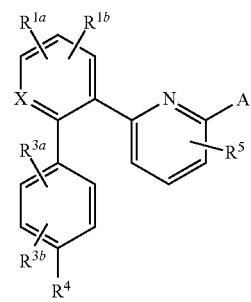

5 Claims, No Drawings

SOLUBLE GUANYLATE CYCLASE ACTIVATORS

RELATED APPLICATIONS

This application is a 35 U.S.C. §371 filing from International Application No. PCT/US2011/057419, filed Oct. 24, 2011, which claims priority to U.S. Provisional Application No. U.S. 61/407,712, filed Oct. 28, 2010. Each of the aforementioned applications is herein incorporated by reference in its entirety.

BACKGROUND OF THE INVENTION

Cyclic GMP (cGMP) is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion, cGMP is produced by particulate and soluble guanylate cyclases as a response to a number of extracellular and intracellular stimuli. In the case of the particulate guanylate cyclases, stimulation is essentially effected by peptidic messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is proposed as the mechanism of the activation by NO. The associated release of the histidine which is bound in the basal state to the iron converts the enzyme into the active conformation.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thromboses, myocardial infarction, strokes or erectile dysfunction results. Pharmacological stimulation of sGC offers a possibility to normalize cGMP production and therefore makes possible the treatment and/or prevention of such disorders.

For the pharmacological stimulation of the sGC, use has been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons predominantly only have weak effects on the cGMP formation in cell lysates. D. L. Vesely, Eur. J. Clin. Invest., vol. 15, 1985, p. 258; D. L. Vesely, Biochem. Biophys. Res. Comm., vol. 88, 1979, p. 1244. A stimulation of heme-free guanylate cyclase by protoporphyrin IX was demonstrated by Ignarro et al., Adv. Pharmacol., vol. 26, 1994, p. 35. Pettibone et al., Eur. J. Pharmacol., vol. 116, 1985 p. 307, described an antihypertensive action of diphenyliodonium hexafluorophosphate and attributed this to a stimulation of sGC. According to Yu et al., Brit. J. Pharmacol, vol. 114, 1995, p. 1587, isoliquiritigenin, which has a relaxing action on isolated rat aortas, also activates sGC. Ko et al., Blood vol. 84, 1994, p. 4226, Yu et al., Biochem, J. vol. 306, 1995, p. 787, and Wu et al., Brit. J. Pharmacol. vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent Application No. 908,456 and German Patent Application No. 19,744,027.

A series of 2-sulfonylaminobenzoic acid N-arylamides, the N-aryl group of which carries a thio substituent, have been mentioned in the literature. These compounds in which the N-aryl group generally carries as further substituents groups which are readily oxidizable such as, for example, two hydroxy groups being in para position with respect to one another and which in this case can be regarded as hydroquinone derivatives, are auxiliaries for the preparation of photographic materials (see, for example, Chemical Abstracts 119, 105757; 120, 41858; 123, 70224; or 126, 257007). British patent publication No. 876,526 (Chemical Abstracts 56, 15432e) discloses 3,5-dichloro-2-methylsulfonylaminobenzoic acid N-(5-chloro-2-(4-chlorophenylmercapto)-phenyl)-amide which can be used for the protection of wool against moths.

It has now been found that the compounds of the present invention effect a strong activation of guanylate cyclase and are therefore useful for the therapy and prophylaxis of disorders which are associated with a low cGMP level.

SUMMARY OF THE INVENTION

The present invention relates to compounds of structural Formula I, below, and the pharmaceutically acceptable salts thereof. The compounds activate soluble guanylate cyclase and are valuable pharmaceutically active compounds for the therapy and prophylaxis of diseases, for example for cardiovascular diseases such as hypertension, pulmonary hypertension, angina pectoris, diabetes, cardiac insufficiency, thromboses or atherosclerosis. The compounds of Formula I are capable of modulating the body's production of cyclic guanosine monophosphate ("cGMP") and are useful for the therapy and prophylaxis of diseases which are associated with a disturbed cGMP balance. The invention furthermore relates to processes for preparing compounds of Formula I, to their use for the therapy and prophylaxis of the abovementioned diseases and for preparing pharmaceuticals for this purpose, and to pharmaceutical preparations which comprise compounds of Formula I.

DETAILED DESCRIPTION OF THE INVENTION

This invention provides compounds of structural Formula I:

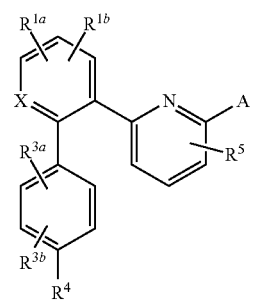

and pharmaceutically acceptable salts thereof, wherein:

X is selected from the group consisting of CH, $CR^2$ and N;

$R^{1a}$ and $R^{1b}$ are independently selected from the group consisting of —H, —F, —Cl, —Br, —CN, cyclopropyl, —$C_{1-3}$alkyl optionally substituted with one to six of —F, and —O—$C_{1-3}$alkyl optionally substituted with one to six of —F;

$R^2$ is selected from the group consisting of —F, —Cl, —Br, —CN, cyclopropyl, —$C_{1-3}$alkyl optionally substituted with one to six of —F, and —O—$C_{1-3}$alkyl optionally substituted with one to six of —F;

$R^{3a}$ and $R^{3b}$ are independently selected from the group consisting of —H, —F, —Cl, —Br, —CN, —$C_{1-3}$alkyl optionally substituted with one to six of —F, and —O—$C_{1-3}$alkyl optionally substituted with one to six of —F;

A is selected from the group consisting of:

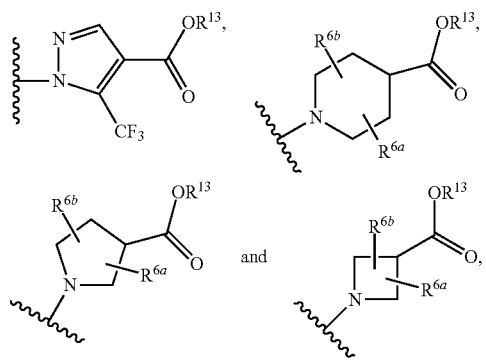

wherein $R^{6a}$ and $R^{6b}$ are independently selected from the group consisting of —H, —Cl, —F, =O (oxo), —O—$C_{1-3}$alkyl, and —$C_{1-3}$alkyl optionally substituted with one to six of —F, and provided that only one of $R^{6a}$ and $R^{6b}$ can be (but is not required to be) oxo; and $R^{13}$ is selected from the group consisting of —H and —$C_{1-6}$ alkyl;

$R^4$ is selected from the group consisting of:

a) —$C_{1-6}$alkyl optionally substituted with one to three substituents independently selected from the group consisting of —F, —OH, and —O$C_{1-3}$alkyl; and optionally substituted with one of oxo;

b) —$C_{1-6}$alkenyl optionally substituted with one to three substituents independently selected from the group consisting of —F, —OH, and —O$C_{1-3}$alkyl; and optionally substituted with one of oxo;

c) —O$C_{1-4}$alkyl optionally substituted with:
 (i) one to three substituents independently selected from the group consisting of —F, —OH, and —O$C_{1-3}$alkyl; and optionally substituted with one of oxo,
 (ii) —$C_{3-6}$cycloalkyl optionally substituted with one to three substituents independently selected from the group consisting of —OH, —CN, —Cl, —F, —$C_{1-3}$alkyl optionally substituted with one to six of —F, and —O—$C_{1-3}$alkyl; and optionally substituted with one of oxo,
 (iii) phenyl optionally substituted with one to three substituents independently selected from the group consisting of —OH, —CN, —Cl, —F, —$C_{1-3}$alkyl optionally substituted with one to six of —F, and —O—$C_{1-3}$alkyl optionally substituted with one to six of —F; and optionally substituted with one of oxo,
 (iv) a 4 to 6 membered heterocycle containing one to two heteroatoms selected from one to two of N, zero or one of O, and zero or one of S, wherein the ring is optionally substituted with one to three substituents independently selected from the group consisting of —OH, —CN, —Cl, —F, —$C_{1-3}$alkyl optionally substituted with one to six of —F, and —O—$C_{1-3}$alkyl; and is optionally substituted with one of oxo, or
 (v) a 5 to 6 membered heteroaryl containing one to three heteroatoms selected from zero to three of N, zero or one of O, and zero or one of S, wherein the ring is optionally substituted with one to three substituents independently selected from the group consisting of —OH, —CN, —Cl, —F, oxo, —$C_{1-3}$alkyl optionally substituted with one to six of —F, and —O—$C_{1-3}$alkyl optionally substituted with one to six of —F; and is optionally substituted with one of oxo;

d) —$S(O)_{0-2}C_{1-3}$alkyl;

e) —$C_{3-6}$cycloalkyl optionally substituted with one to three substituents independently selected from the group consisting of —F, —OH, —$CF_3$, and —O$C_{1-3}$alkyl; and optionally substituted with one of oxo;

f) —$C_{3-6}$cycloalkenyl optionally substituted with one or more substituents independently selected from the group consisting of —F, —OH, —$CF_3$, and —O$C_{1-3}$alkyl; and optionally substituted with one of oxo;

g) a 5-6 membered heteroaryl containing one to three heteroatoms selected from zero to three of N, zero or one of O, and zero or one of S, wherein the ring is optionally substituted with one to three substituents independently selected from the group of —OH, —CN, Cl, —F, —$C_{1-3}$alkyl optionally substituted with one to six of —F, and —O—$C_{1-3}$alkyl optionally substituted with one to six of —F; and is optionally substituted with one of oxo; and h) a heterocycle selected from the group consisting of:

(i)
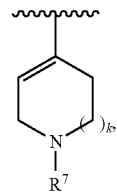

(ii)
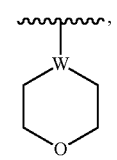

(iii)
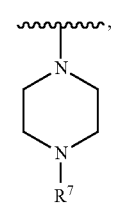

(iv)
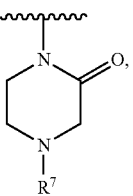

(v) 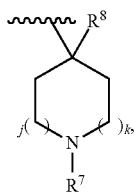

(vi) 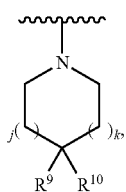

(vii) 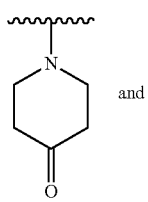 and (viii) 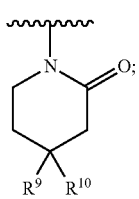

R$^5$ is selected from the group consisting of —H, —F, —OH, —CF$_3$, —OC$_{1-3}$alkyl and —OCF$_3$;
j is an integer selected from 0 and 1;
k is an integer selected from 0 and 1;
W is selected from the group consisting of CR$^8$ and N;
R$^7$ is selected from the group consisting of (a) —H, (b) —C$_{1-6}$ alkyl optionally substituted with one to six of —F, (c) —C$_{1-3}$alkyl substituted with one or two of —OCH$_3$,
(d) —(CH$_2$)$_{0-1}$—C$_{3-6}$cycloalkyl optionally substituted with (i) one to three of —F or (ii) C$_{1-3}$alkyl optionally substituted with one to three of —F, (e) 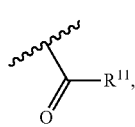

(f) 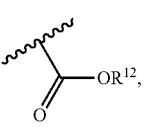

(g) 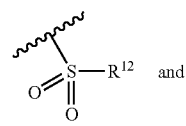 and (h) 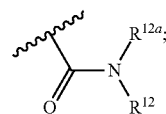

R$^8$ is selected from the group consisting of —H, —F, —OH, and —C$_{1-3}$alkyl optionally substituted with one to six of —F;
R$^9$ is selected from the group consisting of (a) —H, (b) —F, (c) —OH,
(d) —C$_{1-3}$alkyl optionally substituted with substituents selected from the group consisting of (i) —OH and (ii) one to six of —F,
(e) —C$_{3-6}$cycloalkyl optionally substituted with one to three of —F, and
(f) —O—C$_{1-3}$alkyl optionally substituted with —OH;
R$^{10}$ is selected from the group consisting of (a) —H, (b) —F, (c) —C$_{1-3}$alkyl optionally substituted with substituents selected from (i) —OH and (ii) one to six of —F, and
(d) —O—C$_{1-3}$alkyl;
R$^{11}$ is selected from the group consisting of (a) —H, (b) —C$_{1-6}$alkyl optionally substituted with one to six of —F, (c) —C$_{3-6}$cycloalkyl optionally substituted with —CH$_3$, —CF$_3$, —CN, —OH, or —NH$_2$ or one to three of —F;
R$^{12a}$ is selected from the group consisting of (a) —H, (b) —C$_{1-6}$alkyl optionally substituted with one to six of —F, (c) —C$_{3-6}$cycloalkyl optionally substituted with —CH$_3$, —CF$_3$, —CN, —OH, or one to three of —F; and
R$^{12}$ is selected from the group consisting of (a) —C$_{1-6}$alkyl optionally substituted with one to six of —F, and (b) —C$_{3-6}$cycloalkyl optionally substituted with one to three of —F.

In an embodiment of this invention are compounds of structural Formula I having structural Formula II and the pharmaceutically acceptable salts thereof wherein the variables are as defined in Formula I:

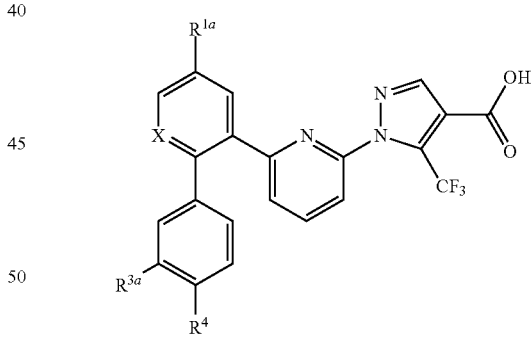

II

In an embodiment of this invention are compounds of structural Formula I or II wherein X is CH. In another embodiment are compounds of structural Formula I or II wherein X is N.

In an embodiment of this invention are compounds of structural Formula I wherein A is selected from

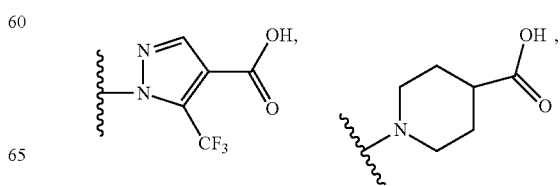

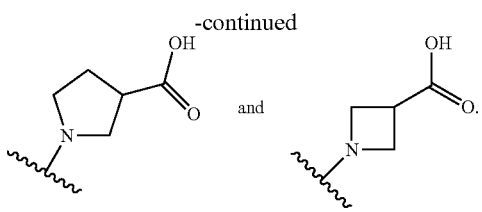 and 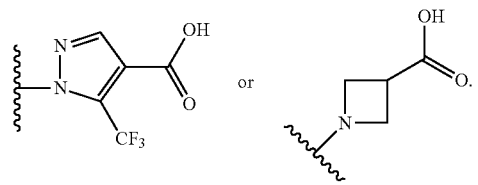 [SMILES: *n1ncc(C(=O)O)c1C(F)(F)F ; *N1CC(C(=O)O)C1]

More particularly A is

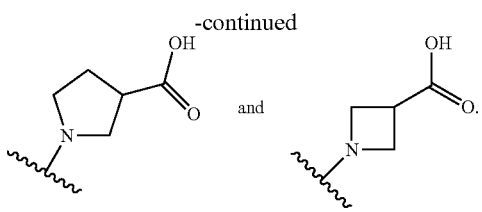 or 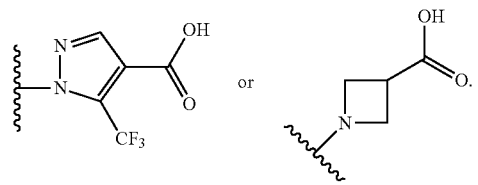 [SMILES: *n1ncc(C(=O)O)c1C(F)(F)F ; *N1CC(C(=O)O)C1]

In an embodiment of this invention are compounds of structural Formula I or II wherein $R^{1a}$ is selected from the group consisting of —H, —Cl, —F, —CH$_3$ and —CF$_3$, and more particularly it is —Cl, —F, —CH$_3$ or —CF$_3$; and $R^b$ is —H.

In an embodiment of this invention are compounds of structural Formula I wherein $R^{3a}$ and $R^{3b}$ are independently selected from the group consisting of —H, —Cl, —F, —CH$_3$, —CF$_3$, OCH$_3$ and —OCF$_3$. In an embodiment of structural Formulas I or II, $R^{3a}$ is selected from the group consisting of —H, —Cl, —F, —CH$_3$, —CF$_3$, —OCH$_3$, and —OCF$_3$ and $R^{3b}$ is —H.

In an embodiment of this invention are compounds of structural Formula I or II wherein $R^4$ is selected from the group consisting of:

a) —C$_{1-3}$alkyl optionally substituted with one to three of —F, and particularly —CF$_3$;

b) —OC$_{1-4}$alkyl optionally substituted with one to three of —F, and particularly it is —OC$_{1-3}$alkyl-CF$_3$;

c) —OC$_{1-2}$alkyl optionally substituted with:

(i) —C$_{3-6}$cycloalkyl optionally substituted with one of oxo and optionally substituted with one to three substituents independently selected from the group consisting of —OH, —CN, —Cl, —F, —C$_{1-3}$alkyl optionally substituted with one to six of —F, and —O—C$_{1-3}$alkyl. Particularly, it is cyclopropyl optionally substituted with one to three substituents independently selected from the group consisting of —F, —OH, —CF$_3$, and more particularly it is cyclopropyl substituted with 1 or 2 of —F;

(ii) phenyl optionally substituted with one of oxo and optionally substituted with one to three substituents independently selected from the group consisting of —OH, —CN, —Cl, —F, —C$_{1-3}$alkyl optionally substituted with one to six of —F, and —O—C$_{1-3}$alkyl optionally substituted with one to six of —F;

(iii) a 4 to 6 membered heterocycle containing one N, wherein the heterocycle is optionally substituted with one of oxo and optionally substituted with one to three substituents independently selected from the group consisting of —OH, —CN, —Cl, —F, —C$_{1-3}$alkyl optionally substituted with one to six of —F, and —O—C$_{1-3}$alkyl. Particularly it is selected from

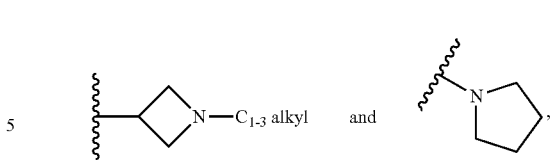

wherein the alkyl substituent on the heterocycle is optionally substituted with one to three of —F; or (iv) a 5 to 6 membered heteroaryl containing one or two heteroatoms selected from one or two of N, zero or one of O, and zero or one of S, wherein the heteroaryl is optionally substituted with one of oxo and optionally substituted with one to three substituents independently selected from the group consisting of —OH, —CN, —Cl, —F, —C$_{1-3}$alkyl optionally substituted with one to six of —F, and —O—C$_{1-3}$alkyl optionally substituted with one to six of —F. Particularly it is furanyl.

d) —C$_{3-6}$cycloalkyl optionally substituted with one of oxo and optionally substituted with one to three substituents independently selected from the group consisting of —F, —OH, —CF$_3$ and —OC$_{1-3}$ alkyl. Particularly it is

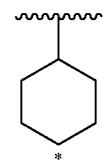 [SMILES: *C1CCCCC1]

wherein the carbon designated with * is optionally substituted with 1 or 2 of —F, —OH, —C$_{1-3}$alkyl optionally substituted with one to three of —F, or —OC$_{1-3}$alkyl, and particularly it is substituted with —CF$_3$, —OCH$_3$, or 1-2 of —F; and e) a heterocycle selected from the group consisting of:

(i)

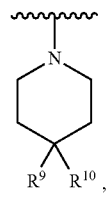

(ii)

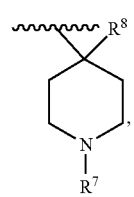

(iii)

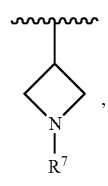

-continued (iv)
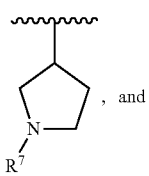, and (v)
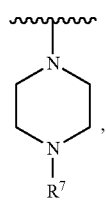

and particularly it is

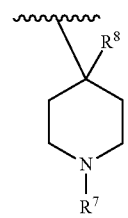

In a further embodiment, R⁴ is selected from the group consisting of:
a) —OC$_{1-2}$alkyl optionally substituted with a 4 to 6 membered heterocycle containing one N, wherein the heterocycle is optionally substituted with one of oxo and optionally substituted with one to three substituents independently selected from the group consisting of —OH, —CN, —Cl, —F, —C$_{1-3}$alkyl optionally substituted with one to six of —F, and —O—C$_{1-3}$alkyl. Particularly the heterocycle is selected from

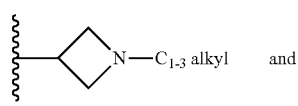 and 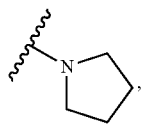, wherein the alkyl substituent on the heterocycle is optionally substituted with one to three of —F;
b) —C$_{3-6}$cycloalkyl optionally substituted with one of oxo and optionally substituted with one to three substituents independently selected from the group consisting of —F, —OH, —CF$_3$, and —OC$_{1-3}$alkyl. Particularly it is

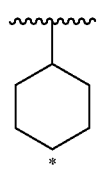

wherein the carbon designated with * is optionally substituted with (i) 1 or 2 of —F, (ii) —OH, (iii) —C$_{1-3}$alkyl optionally substituted with one to three of —F, or (iv) —OC$_{1-3}$alkyl; and particularly it is substituted with —CF$_3$, —OCH$_3$, or 1 or 2 of —F; and
c) a heterocycle selected from the group consisting of:

(i)
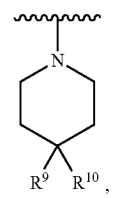, (ii)
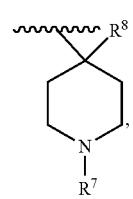, (iii)
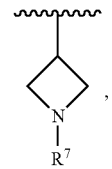, (iv)
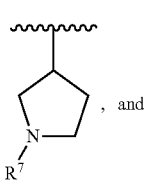, and (v)
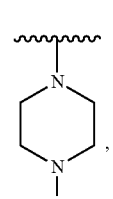, and particularly it is

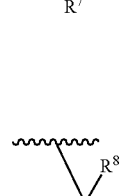.

In an embodiment of this invention are compounds of structural Formula I wherein R⁵ is —H.
In an embodiment of this invention are compounds of structural Formula I wherein R$^{6a}$ and R$^{6b}$ are each —H.
In an embodiment of this invention are compounds of structural Formula I or II wherein R⁷ is selected from:
(i) —C$_{1-3}$alkyl optionally substituted with one to three of —F, (ii) —(CH$_2$)$_{0-1}$—C$_{3-4}$cycloalkyl optionally substituted with —CF$_3$ or one to two of —F, (iii) —C(=O)—C$_{3-4}$cycloalkyl optionally substituted with —CH$_3$, —CF$_3$, —CN, —OH, or —NH$_2$ or one to three of —F, (iv) —C(=O)OC$_{1-3}$alkyl optionally substituted with one to three of —F, (v) —C(=O)—N(C$_{1-3}$alkyl)$_2$, and (vi) —SO$_2$—R$^{12}$ wherein R$^{12}$ is —C$_{1-3}$alkyl or cyclopropyl and R$^{12}$ is optionally substituted with one to three of —F.

In an embodiment of this invention are compounds of structural Formula I or II wherein R$^8$ is selected from —H, —F and —OH, and particularly it is —H.

In an embodiment of this invention are compounds of structural Formula I or II wherein R$^9$ is selected from (i) cyclopropyl optionally substituted with one or two of —F and (ii) —C$_{1-3}$alkyl optionally substituted with one to three of —F, particularly —CF$_3$.

In an embodiment of this invention are compounds of structural Formula I or II wherein R$^{10}$ is —H.

In an embodiment of this invention are compounds of structural Formula I or II wherein R$^{11}$ is selected from —C$_{1-3}$alkyl and —C$_{3-6}$cycloalkyl wherein R$^{11}$ is optionally substituted with —CH$_3$, —CF$_3$, —CN, —OH, or —NH$_2$ or one to three of —F.

In an embodiment of this invention are compounds of structural Formula I or II wherein R$^{12a}$ is selected from the group consisting of —H and —C$_{1-3}$alkyl.

In an embodiment of this invention are compounds of structural Formula I or II wherein R$^{12}$ is selected from —C$_{1-3}$alkyl and cyclopropyl wherein R$^{12}$ is optionally substituted with one to three of —F.

In an embodiment of this invention are compounds of structural Formula I wherein R$^{13}$ is —H.

In a further embodiment of this invention are compounds of structural Formula I and the pharmaceutically acceptable salts thereof wherein:

X is selected form CH and N;

A is selected from

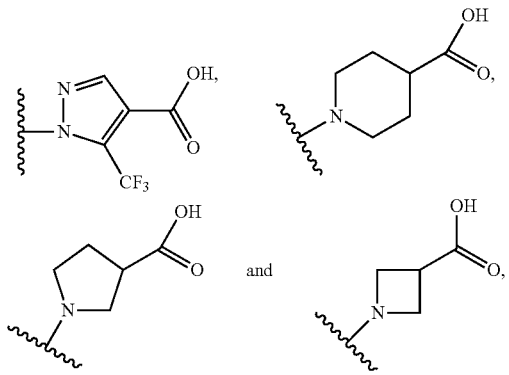

and particularly A is

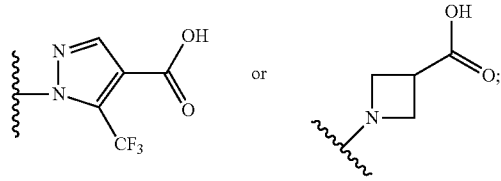 [SMILES: *n1ncc(C(=O)O)c1C(F)(F)F ; "or" ; *N1CC(C(=O)O)C1]

R$^{1a}$ is selected from the group consisting of —H, —Cl, —F, —CH$_3$ and —CF$_3$, and more particularly it is Cl, —F, —CH$_3$ or —CF$_3$;

R$^{1b}$ is —H;

R$^{3a}$ and R$^{3b}$ are independently selected from the group consisting of —H, —Cl, —F, —CH$_3$, —CF$_3$, —OCH$_3$, and —OCF$_3$, and particularly R$^{3b}$ is —H;

R$^4$ is selected from the group consisting of:

a) —C$_{1-3}$alkyl optionally substituted with one to three of —F, and particularly —CF$_3$;

b) —OC$_{1-4}$alkyl optionally substituted with one to three of —F, and particularly it is —OC$_{1-3}$alkyl-CF$_3$;

c) —OC$_{1-2}$alkyl optionally substituted with:

(i) —C$_{3-6}$cycloalkyl optionally substituted with one of oxo and optionally substituted with one to three substituents independently selected from the group consisting of —OH, —CN, —Cl, —F, —C$_{1-3}$ alkyl optionally substituted with one to six of —F, and —O—C$_{1-3}$ alkyl; particularly, it is cyclopropyl optionally substituted with one to three substituents independently selected from the group consisting of —F, —OH, —CF$_3$, and more particularly it is cyclopropyl substituted with 1 or 2 of —F;

(ii) phenyl optionally substituted with one of oxo and optionally substituted with one to three substituents independently selected from the group consisting of —OH, —CN, —Cl, —F, —C$_{1-3}$alkyl optionally substituted with one to six of —F, and —O—C$_{1-3}$alkyl optionally substituted with one to six of —F;

(iii) a 4 to 6 membered heterocycle containing one N, wherein the heterocycle is optionally substituted with one of oxo and is optionally substituted with one to three substituents independently selected from the group consisting of —OH, —CN, —Cl, —F, —C$_{1-3}$alkyl optionally substituted with one to six of —F, and —O—C$_{1-3}$alkyl; particularly it is selected from

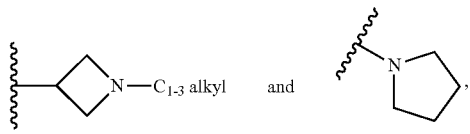

wherein the alkyl substituent on the heterocycle is optionally substituted with 1-3 of —F; or (iv) a 5 to 6 membered heteroaryl containing one or two heteroatoms selected from one or two of N, zero or one of O, and zero or one of S, wherein the heteroaryl is optionally substituted with one of oxo and is optionally substituted with one to three substituents independently selected from the group consisting of —OH, —CN, —Cl, —F, —C$_{1-3}$alkyl optionally substituted with one to six of —F, and —O—C$_{1-3}$ alkyl optionally substituted with one to six of —F; particularly it is furanyl;

d) —C$_{3-6}$cycloalkyl optionally substituted with one of oxo and optionally substituted with one to three substituents independently selected from the group consisting of —F, —OH, —CF$_3$, and —OC$_{1-3}$alkyl; particularly it is

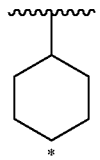 [SMILES: *C1CCCCC1]

wherein the carbon designated with * is optionally substituted with (i) one or two of —F, (ii) —OH, (iii) —C$_{1-3}$alkyl optionally substituted with one to three of —F, or (iv) —OC$_{1-3}$alkyl, and particularly it is substituted with —CF$_3$, —OCH$_3$, or one to two of —F; and e) a heterocycle selected from the group consisting of:

(i)
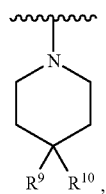

(ii)
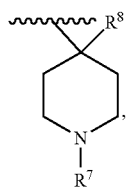

(iii)
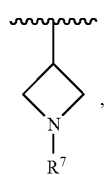

(iv)
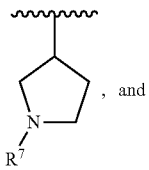, and (v)
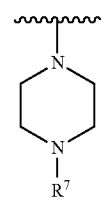

and particularly it is

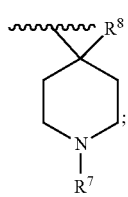;

$R^5$ is —H;
$R^{6a}$ and $R^{6b}$ are each —H;
$R^7$ is selected from:
(i) —$C_{1-3}$alkyl optionally substituted with one to three of —F,
(ii) —$(CH_2)_{0-1}$—$C_{3-4}$cycloalkyl optionally substituted with —$CF_3$ or one to two of —F,
(iii) —C(=O)—$C_{3-4}$cycloalkyl optionally substituted with —$CH_3$, —$CF_3$, —CN, —OH, or —$NH_2$ or one to three of —F,
(iv) —C(=O)O$C_{1-3}$ alkyl optionally substituted with one to three of —F, (v) —C(=O)—N($C_{1-3}$alkyl)$_2$, and
(vi) —$SO_2$—$R^{12}$ wherein $R^{12}$ is —$C_{1-3}$alkyl or cyclopropyl and $R^{12}$ is optionally substituted with one to three of —F;
$R^8$ is selected from —H, —F and —OH, and particularly it is —H;
$R^9$ is selected from (i) cyclopropyl optionally substituted with one or two of —F and (ii) —$C_{1-3}$alkyl optionally substituted with one to three of —F, particularly —$CF_3$;
$R^{10}$ is —H;
$R^{11}$ is selected from —$C_{1-3}$alkyl and —$C_{3-6}$cycloalkyl wherein $R^{11}$ is optionally substituted with —$CH_3$, —$CF_3$, —CN, —OH, or —$NH_2$ or one to three of —F;
$R^{12a}$ is selected from the group consisting of —H and —$C_{1-3}$ alkyl;
$R^{12}$ is selected from —$C_{1-3}$alkyl and cyclopropyl wherein $R^{12}$ is optionally substituted with one to three of —F; and
$R^{13}$ is —H.

Particular examples of this invention include the following compounds and their pharmaceutically acceptable salts:

Example 6: 1-[6-(4-Chloro-3'-methyl-4'-{[1-(2,2,2-trifluoroethyl)azetidin-3-yl]methoxy}biphenyl-2-yl)pyridin-2-yl]-5-(trifluoromethyl)-1H-pyrazole-4-carboxylic acid;

Example 8: 1-{6-[4-chloro-4'-(4-cyclopropylpiperidin-1-yl)biphenyl-2-yl]pyridin-2-yl}-5-(trifluoromethyl)-1H-pyrazole-4-carboxylic acid;

Example 44: 1-{6-[4-chloro-4'-(4,4-difluorocylohexyl)biphenyl-2-yl]pyridin-2-yl}-5-(trifluoromethyl)-1H-pyrazole-4-carboxylic acid;

Example 57: 1-{6-[4'-(4-cyclopropylpiperidin-1-yl)-4-methylbiphenyl-2-yl]pyridin-2-yl}-5-(trifluoromethyl)-1H-pyrazole-4-carboxylic acid;

Example 60: 1-(6-{4-chloro-4'-[1-(2,2,2-trifluoroethyl)piperidin-4-yl]biphenyl-2-yl}pyridin-2-yl)-5-(trifluoromethyl)-1H-pyrazole-4-carboxylic acid;

Example 61: 1-[2'-{4-[1-(2,2,2-trifluoroethyl)piperidin-4-yl]phenyl}-5'-(trifluoromethyl)-2,3'-bipyridin-6-yl]-5-(trifluoromethyl)-1H-pyrazole-4-carboxylic acid;

Example 68: 1-[6-(4-chloro-4'-{4-[(2,2-difluorocyclopropyl)methyl]piperazin-1-yl}biphenyl-2-yl)pyridin-2-yl]-5-(trifluoromethyl)-1H-pyrazole-4-carboxylic acid;

Example 98: 1-(6-{4-chloro-4'-[1-(methoxycarbonyl)piperidin-4-yl]biphenyl-2-yl}pyridin-2-yl)-5-(trifluoromethyl)-1H-pyrazole-4-carboxylic acid;

Example 99: 1-(6-{4-chloro-4'-[1-(ethoxycarbonyl)piperidin-4-yl]biphenyl-2-yl}pyridin-2-yl)-5-(trifluoromethyl)-1H-pyrazole-4-carboxylic acid;

Example 101: 1-(6-{4-chloro-4'-[1-(dimethylcarbamoyl)piperidin-4-yl]-3'-methylbiphenyl-2-yl}pyridin-2-yl)-5-(trifluoromethyl)-1H-pyrazole-4-carboxylic acid;

Example 111: 1-(6-{4-fluoro-4'-[1-(2,2,2-trifluoroethyl)piperidin-4-yl]biphenyl-2-yl}pyridin-2-yl)-5-(trifluoromethyl)-1H-pyrazole-4-carboxylic acid;

Example 125: 1-(6-{3',4-difluoro-4'-[1-(2,2,2-trifluoroethyl)piperidin-4-yl]biphenyl-2-yl}pyridin-2-yl)-5-(trifluoromethyl)-1H-pyrazole-4-carboxylic acid;

Example 136: 1-(6-{4-fluoro-4'-[1-(3,3,3-trifluoropropyl)piperidin-4-yl]biphenyl-2-yl}pyridin-2-yl)-5-(trifluoromethyl)-1H-pyrazole-4-carboxylic acid;

Example 138: 1-(6-{4-fluoro-3'-methyl-4'-[1-(2,2,2-trifluoroethyl)piperidin-4-yl]biphenyl-2-yl}pyridin-2-yl)-5-(trifluoromethyl)-1H-pyrazole-4-carboxylic acid;

Example 139: 1-(5'-chloro-2'-{3-methyl-4-[1-(2,2,2-trifluoroethyl)piperidin-4-yl]phenyl}-2,3'-bipyridin-6-yl)-5-(trifluoromethyl)-1H-pyrazole-4-carboxylic acid;

Example 284: 1-(6-{4-methyl-4'-[1-(2,2,2-trifluoroethyl)piperidin-4-yl]biphenyl-2-yl}pyridin-2-yl)piperidine-4-carboxylic acid;

Example 285: 1-(6-{4-methyl-4'-[1-(2,2,2-trifluoroethyl)piperidin-4-yl]biphenyl-2-yl}pyridin-2-yl)azetidine-3-carboxylic acid;

Example 286: 1-(6-{4-chloro-4'-[1-(cyclopropylcarbonyl)piperidin-4-yl]biphenyl-2-yl}pyridin-2-yl)piperidine-4-carboxylic acid;

Example 287: 1-(6-{4-methyl-4'-[1-(2,2,2-trifluoroethyl)piperidin-4-yl]biphenyl-2-yl}pyridin-2-yl)-5-oxopyrrolidine-3-carboxylic acid;

Example 291: (3R)-1-{6-(4-chloro-4'-[1-(2,2,2-trifluoroethyl)piperidin-4-yl]biphenyl-2-yl}pyridin-2-yl)pyrrolidine-3-carboxylic acid;

Example 295: 1-(6-{4-chloro-4'-[1-(cyclopropylcarbonyl)piperidin-4-yl]-3'-methylbiphenyl-2-yl}pyridin-2-yl)piperidine-4-carboxylic acid; and Example 307: 1-(6-{4-chloro-4'-[1-(2,2,2-trifluoroethyl)piperidin-4-yl]biphenyl-2-yl}pyridin-2-yl)azetidine-3-carboxylic acid.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (n-butyl, s-butyl, i-butyl, t-butyl; Bu=butyl), n- and i-propyl (Pr=propyl), ethyl (Et) and methyl (Me). "Alkenyl" is intended to include both branched and straight carbon chains having the specified number of carbon atoms and which contain at least one carbon-carbon double bond. Examples of alkenyl include but are not limited to vinyl, allyl, isopropenyl, pentenyl, hexenyl, heptenyl, 1-propenyl, 2-butenyl, 2-methyl-2-butenyl, and the like.

"Cycloalkyl" is a cyclized alkyl ring having the indicated number of carbon atoms. Examples of cycloalkyl include but are not limited to cyclopropyl, cyclobutyl, cyclopentyl and cyclohexyl. The cycloalkyl ring may be substituted on any available carbon which results in the creation of a stable structure, including the ring carbon which serves as the point of attachment to the rest of the molecule. "Cycloalkenyl" is an unsaturated alicyclic all-carbon ring with no aromatic character, having the indicated number of carbon atoms. Cycloalkenyl rings have at least one carbon-carbon double bond, and examples include but are not limited to cyclopropenyl, cyclobutenyl, cyclopentenyl and cyclohexenyl.

"Heterocycle" means a saturated ring having the specified number of atoms containing carbon atoms and at least one heteroatom selected from N, S and O. The heterocycle may be attached within the molecule via a carbon or nitrogen in the ring. Examples of heterocycles include but are not limited to azetidinyl, pyrrolidinyl, piperidinyl, piperazinyl, imidazolidinyl, morpholinyl, thiomorpholinyl, tetrahydrofuranyl, tetrahydropyranyl and the like. "Heterocycle" may be defined more specifically herein with respect to total number of atoms in the ring, number and selection of heteratoms, etc. Preferably the heterocycle contains carbon atoms and (i) one or two nitrogen atoms, (ii) one N and one O atom, or (iii) one O atom.

"Heteroaryl" means an aromatic ring having the specified number of atoms in the ring, containing carbon atoms and at least one heteroatom selected from N, S and O. Examples of "heteroaryl" include but are not limited to pyrrolyl, pyrazolyl, imidazolyl, oxazolyl, thiazolyl, thienyl (also known as thiophenyl), oxadiazolyl, thiodiazolyl, furanyl, pyridinyl. "Heteroaryl" may be defined more specifically herein with respect to total number of atoms in the ring, number and selection of heteratoms, etc.

The phrase "optionally mono- or di-substituted with one or more substituents" means that each carbon and heteroatom (when present) available for substitution in the given moiety may be independently unsubstituted or mono- or di-substituted with one or two substituents that are the same or different at each occurrence and which result in the creation of a stable structure as is understood to be reasonable by one skilled in the art, provided that the total number of substituents on the optionally substituted moiety is zero, one or two.

Use of the term "substituted" is intended to encompass mono- and poly-substitution on the specified moiety, unless otherwise specified. A mono-substituted moiety has one substituent, while a poly-substituted moiety has more than one substituent, wherein each carbon atom as well as heteroatom such as nitrogen if present, that is available for substitution in the moiety may independently be unsubstituted, mono- or poly-substituted such that it results in the creation of a stable structure. A moiety that can be optionally substituted encompasses the unsubstituted moiety as well as the substituted moiety.

In some instances the number of substituents which may be optionally present on a moiety is specified, for example but not limited to a certain number such as 1 to 3 or 1 to 6 of —F (fluoro). For example, an alkyl group that can be optionally substituted with 1 to 6 of —F includes, but is not limited to, —$CH_3$, —$CH_2F$, —$CHF_2$, —$CF_3$, —$CH_2CH_3$, —$CH_2$—$CH_2F$, —$CH_2$—$CHF_2$, —$CHF$—$CH_2F$, —$CF_2CF_3$, —$CHF$—$CHF_2$, —$(CH_2)_2CH_3$, —$CH(CF_3)_2$, and the like, as appropriate for the defined number of carbon atoms for the given alkyl group.

Unless expressly depicted or described otherwise, variables with floating bonds such as $R^{1a}$, $R^{1b}$, $R^{3a}$, $R^{3b}$ and $R^5$, are permitted on any available carbon atom in the ring to which each is attached.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

Reference to the compounds of this invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise. For example, an embodiment wherein $-OR^{13}$ is $-OH$ includes compounds having the resulting free acid moiety $-COOH$ as well as the pharmaceutically acceptable salts that can be formed from the resulting $-COOH$ moiety.

In the compounds of Formula II, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding physiologically or toxicologically acceptable salts, in particular the pharmaceutically utilizable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically (i.e., pharmaceutically) acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, $-C_{1-6}$alkyl esters and $-C_{1-6}$ alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention effect an increase of the cGMP concentration via the activation of soluble guanylate cyclase (sGC), and they are therefore useful agents for the therapy and prophylaxis of disorders which are associated with a low or decreased cGMP level or which are caused thereby, or for whose therapy or prophylaxis an increase of the present cGMP level is desired. Accordingly, an object of the instant invention is to provide a method for activating soluble guanylate cyclase in a patient in need thereof, comprising administering a compound of Formula I to the patient in an amount effective to activate soluble guanylate cyclase in the patient. An additional object is to provide a method for increasing the cGMP level in a patient in need thereof, comprising administering a compound of Formula I to the patient in an effective amount for increasing the patient's cGMP level. The activation of sGC by the compounds of Formula I can be examined, for example, in the activity assays described below.

Disorders and pathological conditions which are associated with a low cGMP level or for which an increase of the cGMP level is desired are, for example, cardiovascular diseases, such as endothelial dysfunction, diastolic dysfunction, atherosclerosis, hypertension, pulmonary hypertension, stable and unstable angina pectoris, thromboses, restenosis, myocardial infarction, stroke (ischemic and hemorrhagic), cardiac insufficiency (including acute and congestive heart failure) and/or pulmonary hypertonia, or, for example, erectile dysfunction, asthma bronchiale, chronic kidney insufficiency and/or diabetes. Compounds of Formula I can additionally be used in the therapy of cirrhosis of the liver and also for improving a restricted memory performance or ability to learn. Accordingly, the instant invention provides a method for treating or preventing the above-described medical conditions comprising administering a therapeutically or prophylactically effective, as appropriate, amount of a compound of Formula I to a patient in need of such treatment or prevention.

In general, compounds that are sGC activators can be identified as those compounds which have an Inflection Point/maximum fold induction over DMSO control in the sGC Cell-Based Assay of less than or equal to about 10 µM/equal to or greater than about 4-fold; preferably less than or equal to about 200 nM/equal to or greater than about 20-fold; and most preferably less than or equal to about 100 nM/equal to or greater than about 50-fold, in the Cell-based sGC Functional Assay described below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2.5 mg, 5 mg, 10 mg, 20 mg, 40 mg, 50 mg, 75 mg, 100 mg, etc., on a daily basis. In some cases, depending on the individual response, it may be necessary to deviate upwards or downwards from the given daily dose.

The term "patient" includes animals, preferably mammals and especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention of myocardial infarction.

In the methods of treatment of this invention, the sGC activators may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred, particularly solid oral dosage units such as pills, tablets or capsules.

Accordingly, this invention also provides pharmaceutical compositions comprised of a compound of Formula I and a pharmaceutically acceptable carrier. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. The carrier is comprised of one or more pharmaceutically acceptable excipients. Furthermore, a therapeutically effective amount of a compound of this invention can be used for the preparation of a medicament useful for activating soluble guanylate cyclase, for normalizing a disturbed cGMP balance, or for treating or preventing any of the medical conditions described herein, in dosage amounts described herein.

The amount of active compound of Formula I and/or its pharmaceutically acceptable salts in the pharmaceutical composition may be, for example but not limited to, from 0.1 to 200 mg, preferably from 0.1 to 50 mg, per dose on a free acid/free base weight basis, but depending on the type of the pharmaceutical composition and potency of the active ingredient it could also be lower or higher. Pharmaceutical compositions usually comprise 0.5 to 90 percent by weight of the active compound on a free acid/free base weight basis.

The compounds of Formula I activate soluble guanylate cyclase. On account of this property, apart from use as pharmaceutically active compounds in human medicine and veterinary medicine, they can also be employed as a scientific tool or as aid for biochemical investigations in which such an effect on soluble guanylate cyclase is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. An additional active agent (or agents) is intended to mean a pharmaceutically active agent (or agents) different from the compound of Formula I. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme (ACE) inhibitors (e.g, alacepril, benazepril, captopril, ceronapril, cilazapril, delapril, enalapril, enalaprilat, fosinopril, imidapril, lisinopril, moexepril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists (e.g., candesartan, eprosartan, irbesartan, losartan, olmesartan, telmisartan, valsartan) neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)-N-(2-carbamoyl-2-methylpropyl)-5-amino-4-hydroxy-2,7-di-isopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, bepridil, diltiazem, felodipine, gallopamil, nicardipine, nifedipine, niludipine, nimodipine, nisoldipine veraparmil), potassium channel activators (e.g., nicorandil, pinacidil, cromakalim, minoxidil, aprilkalim, loprazolam), diuretics (e.g., hydrochlorothiazide) including loop diuretics such as ethacrynic acid, furosemide, bumetanide and torsemide, sympatholitics, beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, pravastatin, fluvastatin, atorvastatin, rosuvastatin, ezetimibe); niacin in immediate-release or controlled release forms, and particularly in niacin in combination with a DP antagonist such as laropiprant (TREDAPTIVE®) and/or with an HMG-CoA reductase inhibitor; niacin receptor agonists such as acipimox and acifran, as well as niacin receptor partial agonists; or with other drugs beneficial for the prevention or the treatment of the above-mentioned diseases including nitroprusside and diazoxide.

Additional active agents may be administered in combination with a compound of this invention include metabolic altering agents such as (1) insulin sensitizing agents, for example (i) PPARγ agonists, such as the glitazones (e.g. pioglitazone, rosiglitazone, netoglitazone, rivoglitazone, and balaglitazone) and other PPAR ligands, including (a) PPARα/γ dual agonists, such as muraglitazar, aleglitazar, sodelglitazar, and naveglitazar, (b) PPARα agonists, such as fenofibric acid derivatives (gemfibrozil, clofibrate, ciprofibrate, fenofibrate and bezafibrate), (ii) biguanides, such as metformin and its pharmaceutically acceptable salts, in particular, metformin hydrochloride; (2) insulin or insulin analogs, such as insulin lispro, insulin detemir, insulin glargine, insulin glulisine, and inhalable formulations of each thereof; (3) sulfonylurea and non-sulfonylurea insulin secretagogues, such as tolbutamide, glyburide, glipizide, glimepiride, mitiglinide, and meglitinides, such as nateglinide and repaglinide; and (4) incretin mimetics, such as GLP-1, GLP-1 analogs, derivatives, and mimetics, and GLP-1 receptor agonists such as exenatide, liraglutide and taspoglutide.

Dipeptidyl peptidase-IV (DPP-4) inhibitors can be used in combination with compounds of this invention including, but not limited to, sitagliptin (disclosed in U.S. Pat. No. 6,699,871), vildagliptin, saxagliptin, alogliptin, denagliptin, carmegliptin, dutogliptin, melogliptin, and linagliptin. Antiobesity compounds can be combined with compounds of this invention, for example, topiramate, zonisamide, naltrexone, phentermine, bupropion, fenfluramine, dexfenfluramine, sibutramine; lipase inhibitors, such as orlistat and cetilistat; neuropeptide $Y_1$ or $Y_5$ antagonists such as MK-0557; and CB1 receptor inverse agonists and antagonists such as rimonabant and taranabant. Any active agent used in combination with a compound of this invention may be in a pharmaceutically acceptable salt form thereof.

The compounds of the present invention can be prepared according to the procedures of the following general Schemes using appropriate materials and are further exemplified by the specific Examples which follow. =By utilizing the procedures described herein, one of ordinary skill in the art can readily prepare additional compounds of the present invention claimed herein. In the general Schemes provided below, variables that are defined in Formula I (e.g., X, $R^{1a}$, $R^{1b}$, $R^2$, A, etc.) are also used in many of the structural depictions. Unless otherwise noted, Y represents an optionally substituted nitrogen, optionally substituted carbon or an oxygen atom. R', and R" are alkyl if not otherwise mentioned. The variables p and q are integers independently selected from 0 and 1. Other variables in the schemes are defined as noted. Throughout the synthetic schemes, the following abbreviations may be used.

Useful intermediates for preparation of compounds of Formula I include appropriately substituted phenyl or pyridyl compounds 1 (X=N or CH), where R is a group such as halogen or —OH, that will allow for further modification. Compounds where R=—OH can readily be accessed by coupling an aryl or pyridyl boronic acid or ester to chloropyridine compound 1a (PCT publication WO2009/032249). One such example is shown in Scheme 1, in which methyl ether 1b is coupled to pyridyl chloride 1a under the conditions of Suzuki reaction to provide 1e, and the methyl group is removed using TMSI to provide 1d. Further treatment with triflic anhydride in the presence of a base such as pyridine in an aprotic solvent such as DCM provides 1e.

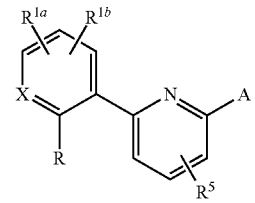

1

| | |
|---|---|
| aq, aq. = aqueous | BuLi, n-BuLi = n-butyllithium |
| Ar = aryl | ACN, MeCN = Acetonitrile |
| Ac = acetate | Bn = benzyl |
| Bu = butyl, t-Bu = tert-butyl | CBZ, Cbz = Benzyloxycarbonyl |
| cPr = cyclopropyl | conc, conc. = concentrated |
| BOC, Boc = t-butyloxcarbonyl | DAST = (diethylamino)sulfur trifluoride |
| DCM = dichloromethane | dba = dibenzylideneacetone; |
| | $Pd_2dba_3$ = tris(dibenzylidineacetone)dipalladium |
| DIEA = diisopropylethylamine | DIAD = diisopropylazodicarboxylate |
| DMAC, DMA = dimethylacetamide | DMAP = 4-dimethylaminopyridine |
| DMSO = dimethylsulfoxide | DMF = N,N-dimethylformamide |
| Et = ethyl | dppf, DPPF = 1,1'-bis(diphenylphosphino)ferrocene |
| EtOAc = ethyl acetate | DIBAL, DIBAL-H = diisobutylaluminum hydride |
| eq. = equivalent(s) | ESI = electrospray ionization |
| HOAc = acetic acid | EtOH = ethanol |
| iPr = isopropyl | HPLC = High pressure liquid chromatography |
| h, hr = hour | LAH = Lithium aluminum hydride |
| IPA, i-PrOH = isopropanol | LCMS = liquid chromatography-mass spectroscopy |
| MeOH = methanol | LHMDS = lithium bis(trimethylsilyl)amide |
| Me = methyl | min, min. = minute(s) |
| Ms = methanesulfonyl | Py = pyridyl |
| NMP = N-methylpyrrolidinone | Pd/C = palladium on activated carbon |
| NMR = nuclear magnetic resonance | RT, rt = room temperature |
| Ph = phenyl | sat. = saturated |
| Pr = propyl | Tosyl = toluenesulfonyl |
| THF = tetrahydrofuran | Tf, triflate = trifluoromethanesulfonate; triflic = trifluoromethanesulfonic |
| TBAF = tetrabutylammonium fluoride | TLC = thin layer chromatography; |
| TBAI = tetrabutylammonium iodide | prep TLC = preparative thin layer chromatography |
| TFA = Trifluoroacetic acid | Xantphos = 4,5-bis(diphenylphosphino)-9,9-dimethylxanthene |
| DAST = (Diethylamino)sulfur trifluoride | Boc = tert-butyl carbonyl |
| tBu, $^tBu$, t-butyl = tert-butyl | DIEA, Hunig's base = N,N-diisopropylethyl amine |
| DMSO = dimethyl sulfoxide | Ent, Ent. = enantiomer |
| Hex, hex = hexanes | Xphos, X-Phos = 2-Dicyclohexylphosphino-2',4',6'-triisopropylbiphenyl |
| TMS = Trimethyl silyl | TMSI = Iodo trimethyl silane, Trimethyl silyl iodide |
| DCM = dichloromethane | |

SCHEME 1

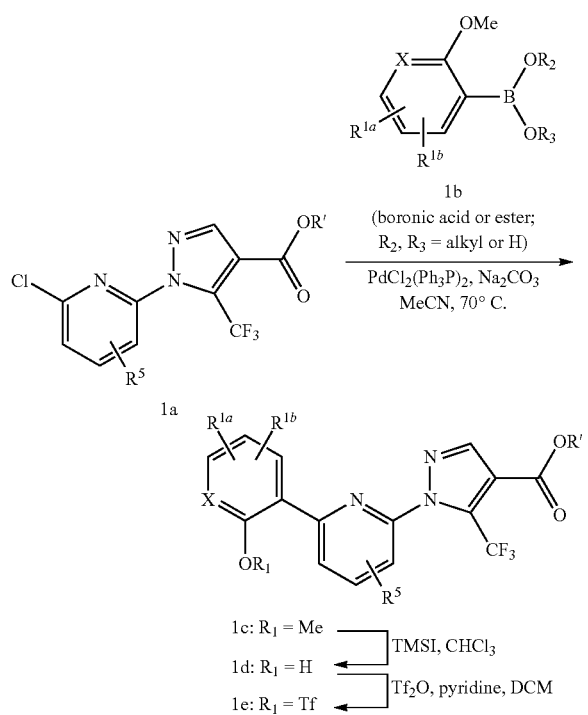

Alternatively, for compounds 1d where X=N, the hydroxyl group may be introduced by displacement of a fluoride or chloride via hydrolysis, or by introduction of a methoxy group, followed by demethylation by TMSI or BBr$_3$, to provide the hydroxypyridine (as will be known to those skilled in the art, the hydroxypyridine can also exist in the tautomeric pyridone form, but is depicted as the hydroxypyridine throughout for simplicity), as in the example shown in Scheme 2.

As will be known to those skilled in the art, several methods exist to cross-couple an aryl group to an appropriately substituted intermediate 1e, including the conditions of Suzuki and Stille. One such method is shown in Scheme 3, involving a Suzuki cross coupling reaction between an appropriately substituted intermediate and a phenylboronic acid or boronic ester 3a, utilizing a catalyst such as dichloro bis(triphenylphosphine)palladium(II) and a base such as aqueous sodium carbonate in an appropriate solvent such as acetonitrile, often at elevated temperatures (Heterocycles, 2003, 60, 1891) to give compound 3d. Alternatively, 1e can be converted to the boronate ester 3b by reaction with bis(pinacolato)diboron using a catalyst such as Pd(dppf)Cl$_2$ or Pd(di$^t$Budppf)Cl$_2$ in the presence of a base such as potassium acetate and an appropriate solvent such as DMSO, typically at elevated temperatures (*J. Org. Chem.* 1995, 60, 7508), or employing a catalyst such as bis(tricyclohexylphosphine)palladium(0) and a base such as sodium carbonate in a solvent such as acetonitrile (*Tetrahedron*, 2001, 57, 9813). The resultant boronate ester 3b can then be cross-coupled to an appropriately substituted aryl or heteroaryl ring 3c (L=Cl, Br, I, or OTf) using Suzuki coupling conditions, as described above, to provide compound 3d.

SCHEME 2

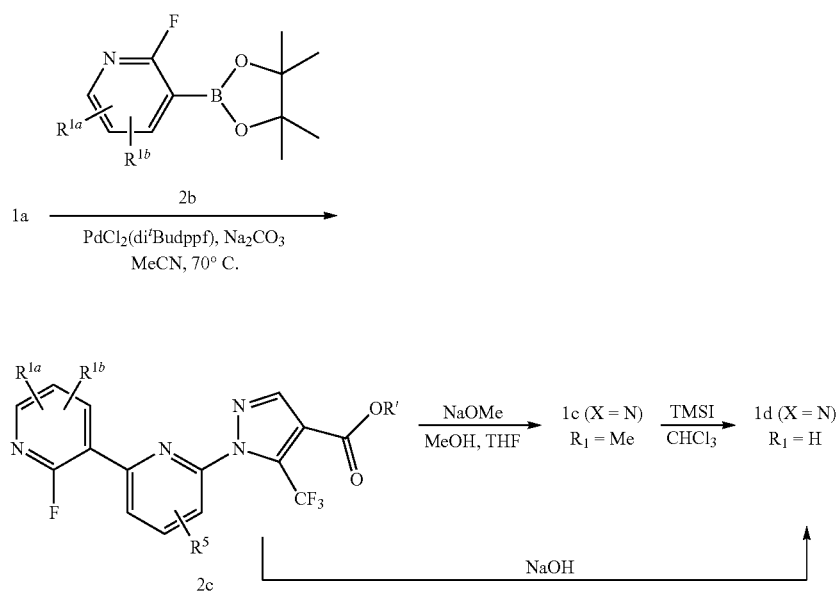

SCHEME 3

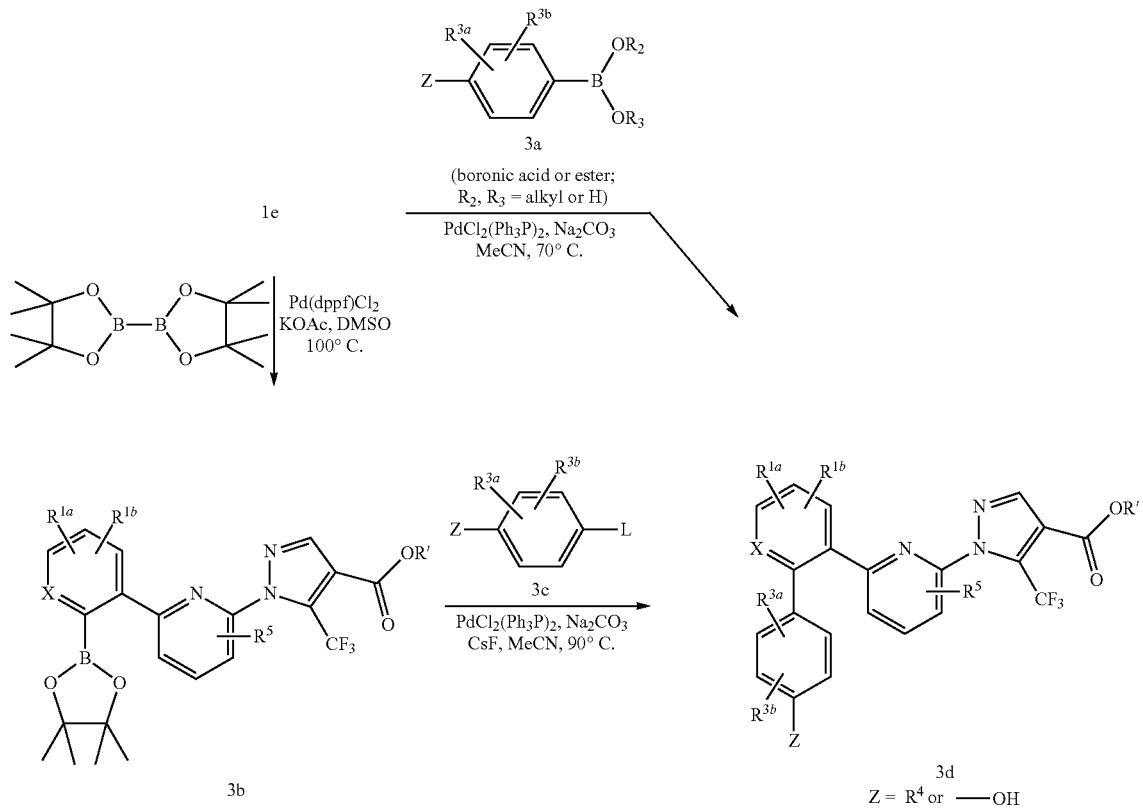

When Z=—OH, the hydroxy group in 3d may be alkylated. For example, as depicted in Scheme 4, treatment of 4a with L-R$_1$ (R$_1$=alkyl) which is an alkyl halide (when L=Cl, Br or I) or alkyl triflate (when L=triflate) in presence of a base such as K$_2$CO$_3$ or Cs$_2$CO$_3$, typically in a polar solvent such as DMF at ambient or slightly elevated temperatures, affords ethers 4b. Such ethers may also be formed using Mitsunobu conditions, involving reaction of 4a with an alcohol R$_1$—OH (R$_1$=alkyl), typically in an aprotic solvent such as DCM or THF, in presence of a phosphine such as triphenylphosphine and an azodicarbonyl reagent such as diisopropyl azodicarboxylate (*Synthesis* 1981, 1).

SCHEME 4

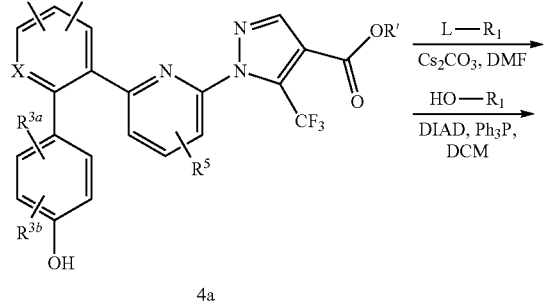

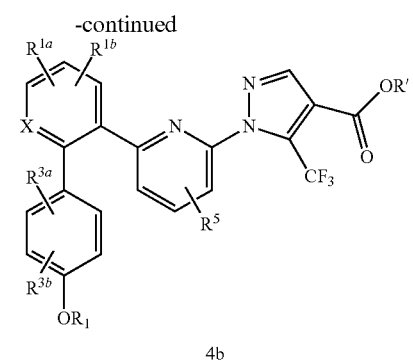

Another example of modification of a hydroxyaromatic group is shown in Scheme 5, in which treatment with a halogenating agent such as iodine in the presence of silver sulfate in a solvent such as EtOH provides a halogenated species such as 5b. Such halogenations typically occur ortho and/or para to the phenol. Especially when V=I or Br, the hydroxyaryl halogen may be further modified by reactions including, but not limited to, cross-coupling reactions, nitration, carbonylation, and cyanation. One example shown in Scheme 5 involves conversion of 5b to the methyl derivative 5c by reaction with trimethylboroxine, in the presence of a catalyst such as Pd(di$^t$Bu-dppf)Cl$_2$ and a base such as sodium carbonate, and in a solvent such as dioxane, typically at elevated temperatures. (Tetrahedron Letters 2000, 6237)

SCHEME 5

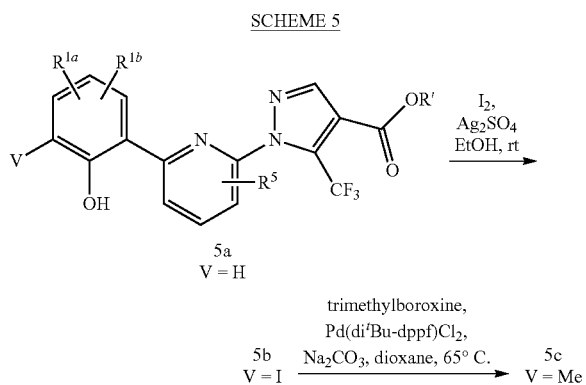

A particularly versatile intermediate to the preparation of compounds of Formula I is triflate 6a, which may then undergo coupling reactions with various agents including, but not limited to, boronic acids and esters, amines, amides, thiol, alcohol and heterocycles. One such example is shown in Scheme 6, involving coupling of triflate 6a with an alkenyl-boronic acid or ester 6b, wherein Y is optionally substituted C or N. Such boronic esters can be obtained commercially, or synthesized using procedures known to those skilled in the art (For example: *J. Org. Chem.* 1995, 60, 7508; *Tetrahedron*, 2001, 57, 9813). Cross-coupling can be realized in the presence of a catalyst such as dichloro bis(triphenylphosphine) palladium(II) and a base such as aqueous solution of sodium carbonate, and in a solvent such as MeCN, typically at elevated temperature to provide 6d. If desired, the resultant alkene 6d may be reduced to alkane 6f via hydrogenation, using a catalyst such as platinum(IV) oxide in a solvent such as EtOH-EtOAc under a hydrogen atmosphere. An example of a cross-coupling reaction of triflate 6a and an amino compound 6e is also shown in Scheme 6, in which a piperidine or piperazine is coupled to the triflate using a phosphine ligand such as 2-(di-t-butyl(phosphino)-2"-methylbiphenyl, a Pd(0) catalyst such as $Pd_2dba_3$ and a base such as $K_3PO_4$, by heating in a solvent such as toluene to provide 6e (Buchwald et al, *J. Org. Chem.* 2000, 65, 1158).

SCHEME 6

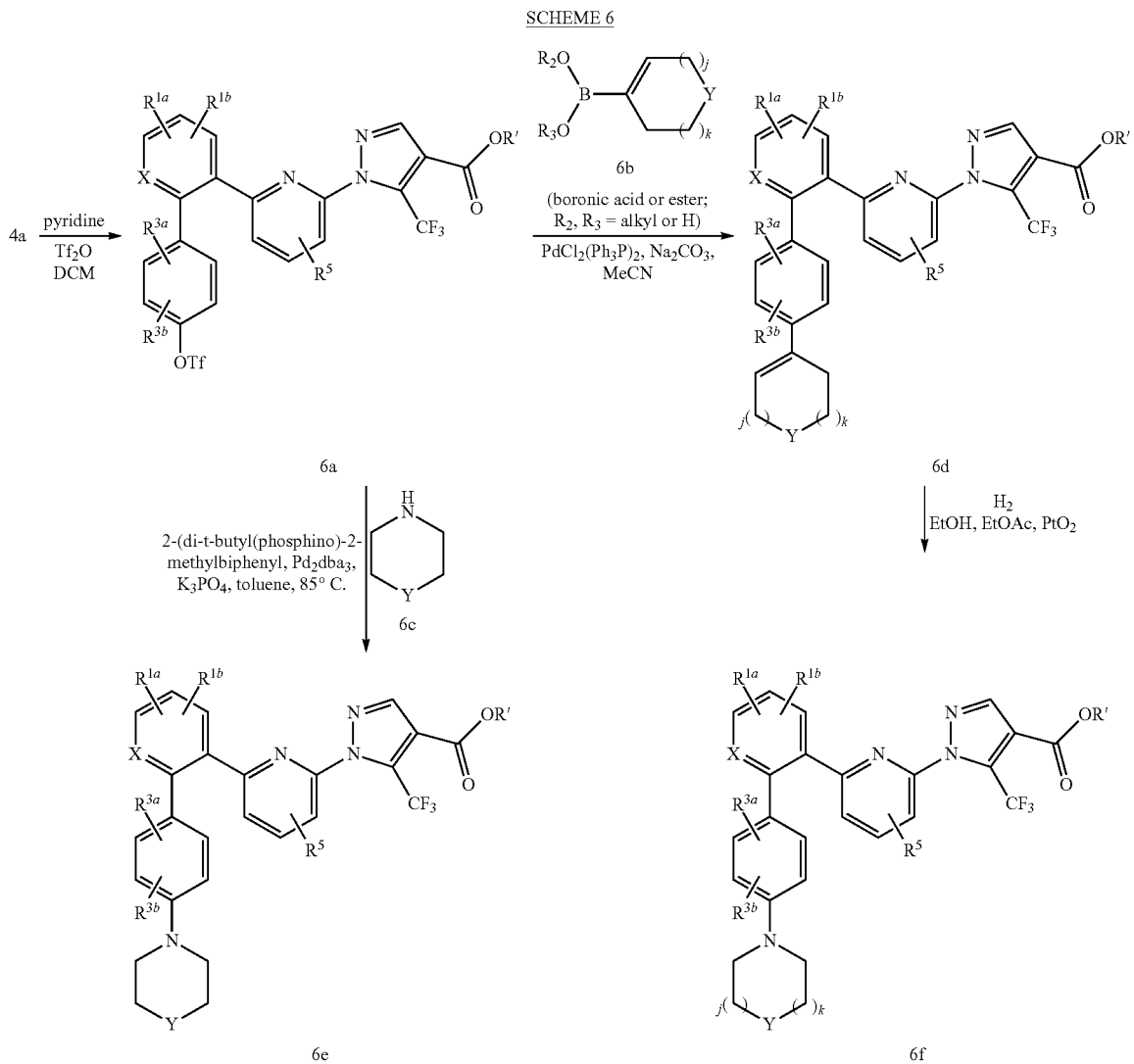

When intermediate 3e has the form of 7b, 7c, 7d, 7e, or 7f, its synthesis may commence with a bromo, iodo-substituted arene such as 7a shown in Scheme 7. Such arenes may undergo selective cross-coupling reactions at iodide by methods known to those skilled in the art. Examples include, but are not limited to, Suzuki, Stille, amidation and amination reactions, and coupling with organozine reagents. In one example, commerically available 7a is reacted with a compound containing an amino group, in the presence of a phosphine ligand such as 2-(di-t-butyl(phosphino)-2"-methylbiphenyl, a Pd(0) catalyst such as $Pd_2$ $dba_3$ and a base such as $K_3PO_4$, by heating in a solvent such as toluene, to give compound 7b. In another example, 7a is reacted with a compound containing an amide group, in the presence of a diamine ligand such as N,N'-dimethylethane-1,2-diamine, CuI and a base such as $K_3PO_4$, by heating in a solvent such as toluene, to give compound 7c. In another example, 7a is reacted with a compound containing a boronic acid or boronic ester group, in the presence of a Pd catalyst such as $Pd(PPh_3)_2Cl_2$ and a base such as aqueous solution of $Na_2CO_3$, by heating in a solvent such as MeCN, to give compound 7d, which is further reduced by hydrogen gas in the presence of a catalyst such as $PtO_2$ to give compound 7e. In another example, 7a is reacted with an N-Boc protected iodoazetidine, upon treatment with Zn powder pretreated with TMSCl, in the presence of a Pd catalyst such as $Pd_2$ $dba_3$ and a ligand such as $P(2-furyl)_3$, to give compound 7f.

SCHEME 7

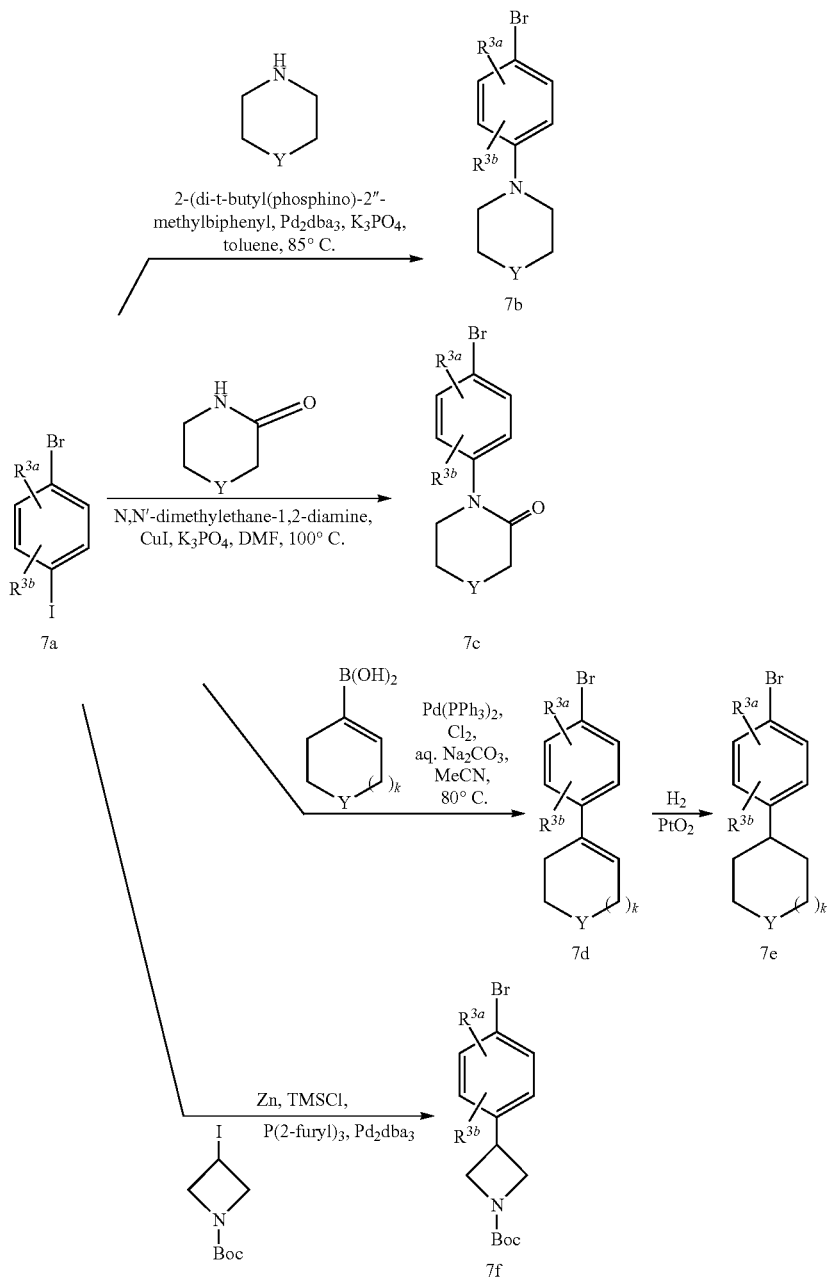

Ketone and aldehyde groups can be incorporated into the compounds and modified by, for example, conversion to difluoro species, alcohols, alkyl or haloalkyl groups. As depicted in Scheme 8, if desired a difluoromethyl group may be introduced by reaction of a suitably substituted aldehyde or ketone such as 8a, 8e or 8e with DAST, in a solvent such as DCM to provide difluoromethyl analog 8b, 8d, or 8g, respectively. In another example, ketone 8e may react with TMSCF$_3$, in the presence of a catalyst such as TBAF, in a solvent such as THF, followed by treatment with an aqueous acid such as 6 M HCl to provide trifluoromethyl tertiary alcohol 8f.

SCHEME 8

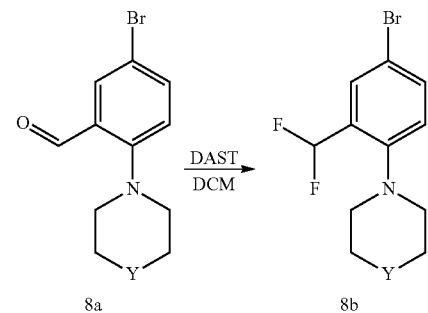

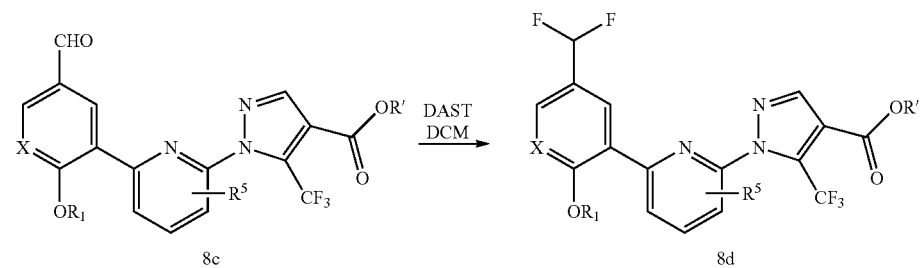

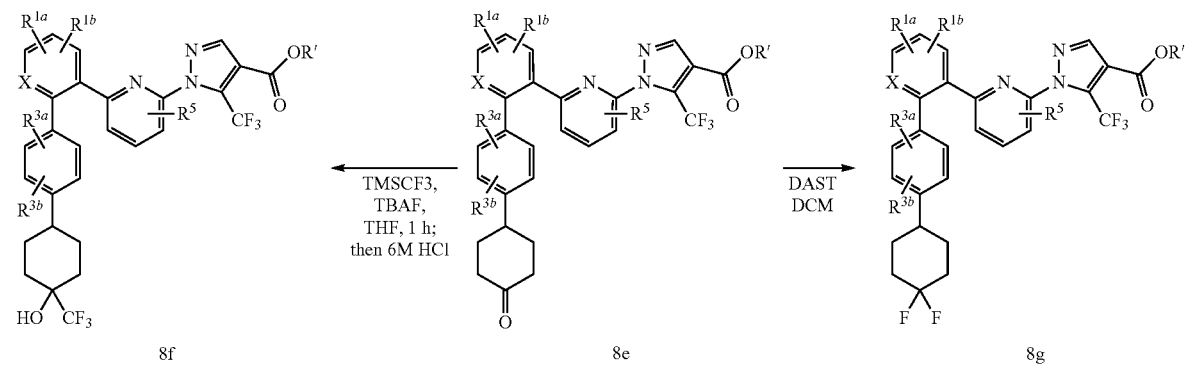

R$_1$ = alkyl

As depicted in Scheme 9, if desired a monofluoro group substituent may be introduced by reaction of a suitably substituted alcohol such as 9a with DAST, in a solvent such as DCM to provide fluoro analog 9b.

SCHEME 9

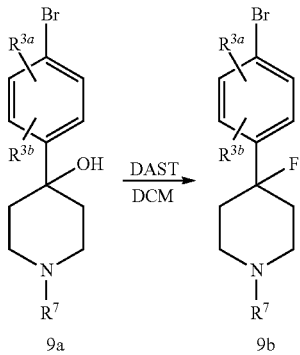

As depicted in Scheme 10, if desired a protecting group such as a Boc group may be removed from an amine such as 10a by treatment of an acid such as TFA in a solvent such as DCM to give free amine 10b. The amine may be further reacted with an electrophile in the presence of a base such as DIEA and in a solvent such as MeCN or DCM, to provide analog 10e with an alkyl, acyl, carbamyl, sulfonyl or carbonyl substituent, respectively.

SCHEME 10

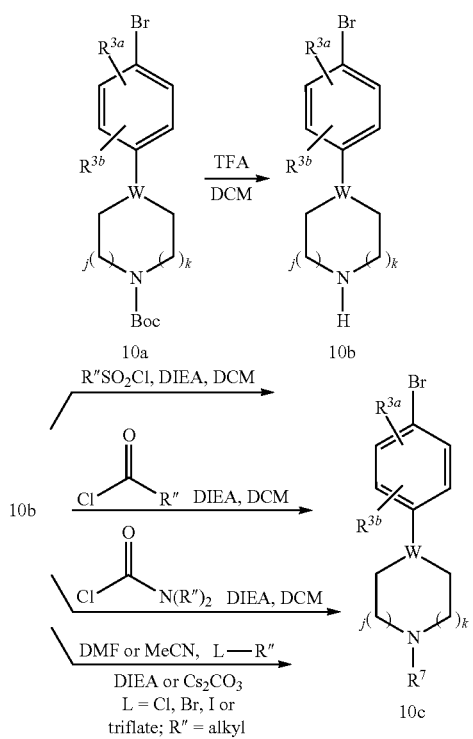

If $R^7$ in the above 10c is an acyl group, the amide 111a if desired can be further converted to alkyl amine 11b, typically by employing reaction with a strong reductant such as LiAlH$_4$ or borane-THF complex, in an aprotic solvent such as THF.

SCHEME 11

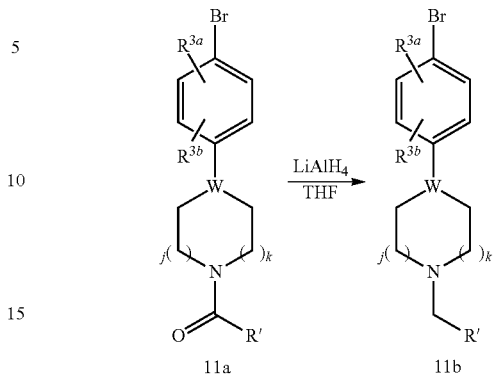

As depicted in Scheme 12, 12a (L=Cl, Br, I, or OTf) can be converted to the boronic ester 12b, by reaction with bis(pinacolato)diboron using a catalyst such as Pd(di$^t$Bu-dppf)Cl$_2$ in the presence of a base such as potassium acetate and an appropriate solvent such as dioxane or DMSO, typically at elevated temperatures (J. Org. Chem. 1995, 60, 7508), or employing a catalyst such as bis(tricyclohexylphosphine)palladium(0) and a base such as sodium carbonate in a solvent such as acetonitrile (Tetrahedron, 2001, 57, 9813).

SCHEME 12

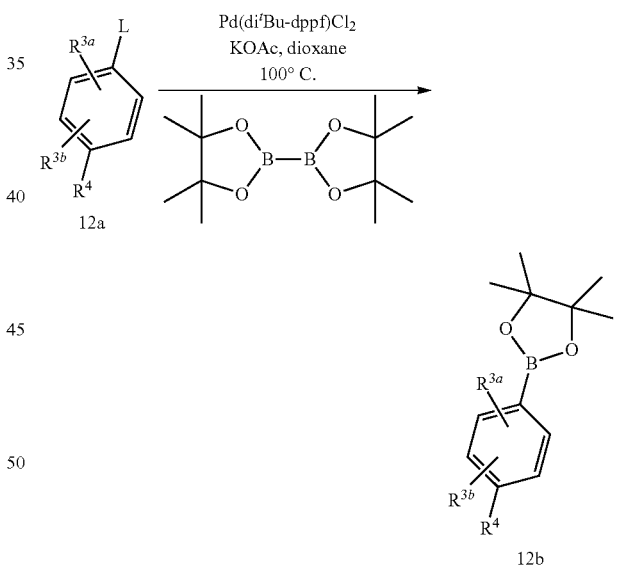

12b can react with 13a selectively on the iodo group, utilizing a catalyst such as dichloro bis(triphenylphosphine) palladium(II) and a base such as aqueous sodium carbonate in an appropriate solvent such as acetonitrile, often at elevated temperatures (Heterocycles, 2003, 60, 1891) to give compound 13b. 13b can be converted to the boronic ester 13c by reaction with bis(pinacolato)diboron using a catalyst such as Pd(dppf)Cl$_2$ or Pd(di$^t$Bu-dppf)Cl$_2$ in the presence of a base such as potassium acetate and an appropriate solvent such as dioxane, typically at elevated temperatures (J. Org. Chem. 1995, 60, 7508).

SCHEME 13

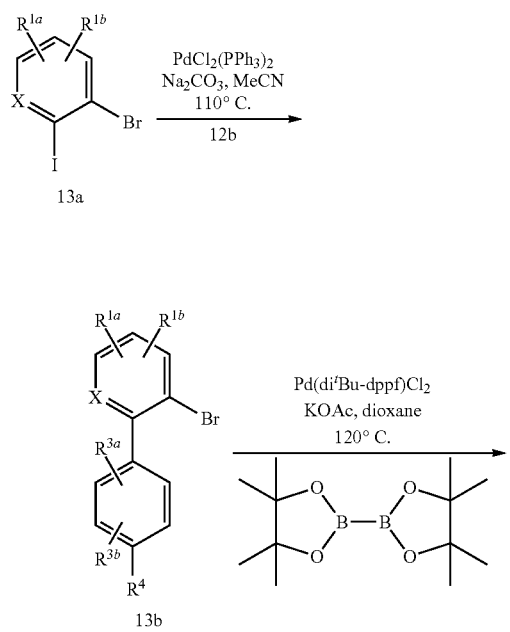

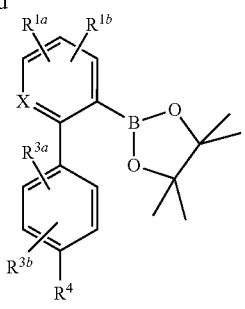

13e can be reacted with a 2-halopyridine such as 14a1 and 14a2, employing a catalyst such as dichloro bis(triphenylphosphine)palladium(II) and a base such as aq. sodium carbonate in a solvent such as acetonitrile (Tetrahedron, 2001, 57, 9813). The resultant 14b1 can be cross-coupled with an amine or an amide such as 14c1 employing a Pd(0) source such as $Pd_2dba_3$, and a phosphine ligand such as X-phos, with a base such as $K_3PO4$, in a solvent such as dioxane, typically at elevated temperature (J. Am. Chem. Soc. 2003, 125, 6653; Nature Protocols 2007, 2, 2881), to give 14d. If the resultant pyridine carries a good leaving group such as a fluorine at 2-position, for example 14b2, the leaving group can be displaced by amine such as 14c2 using base such as cesium carbonate, in a polar solvent such as DMF, typically at elevated temperature to give 14d when q=0.

SCHEME 14

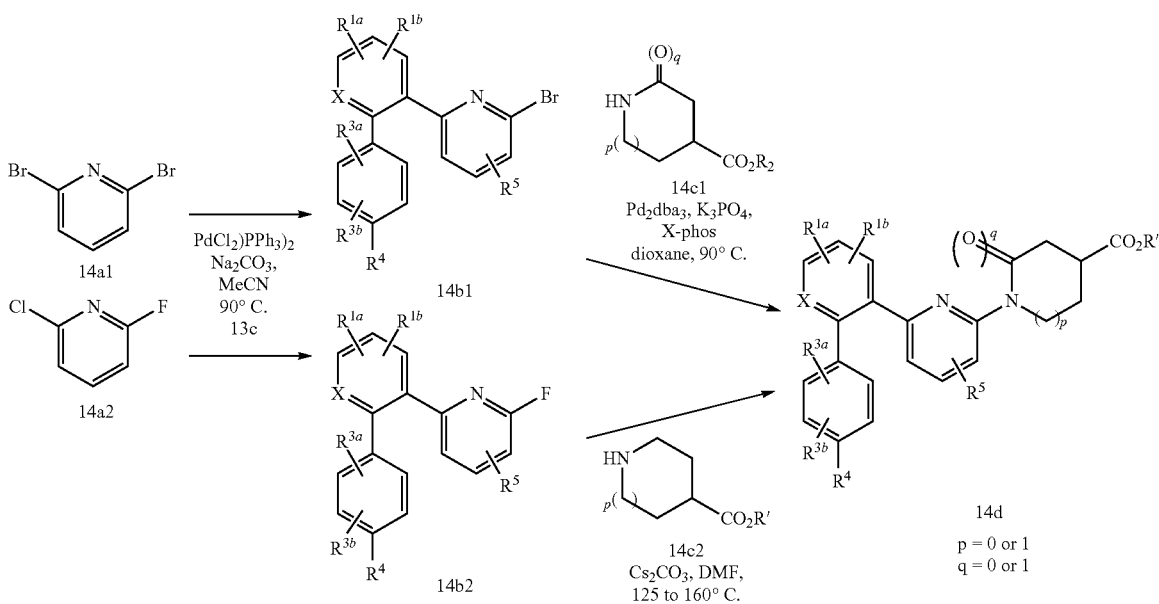

If 3d or 14d contains an amine with a protecting group, such as the Boc group in 15a, wherein $R^{13}$ within A is $C_{1-6}$alkyl, the protecting group may be removed and the revealed amine can be further elaborated. In one example, 15a is treated with an acid such as TFA in a solvent such as DCM to give free amine 15b. The amine may be further reacted with an electrophile such as, but not limited to, an alkyl sulfonate, alkyl halide, acyl halide, carbonyl halide, sulfonyl halide and carbamyl halide, in the presence of a base such as DIEA or cesium carbonate, and in a solvent such as DCM, MeCN or DMF, to provide analog 15e in which $R^7$ may be an alkyl, acyl, carbamyl, sulfonyl or carbonyl group, respectively.

SCHEME 15

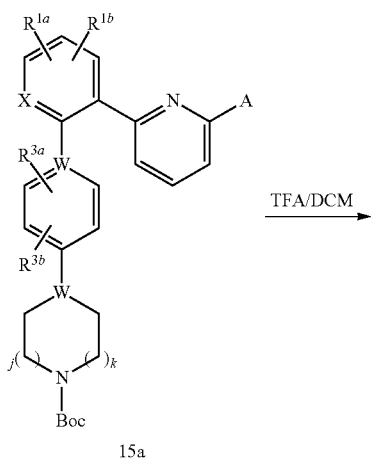

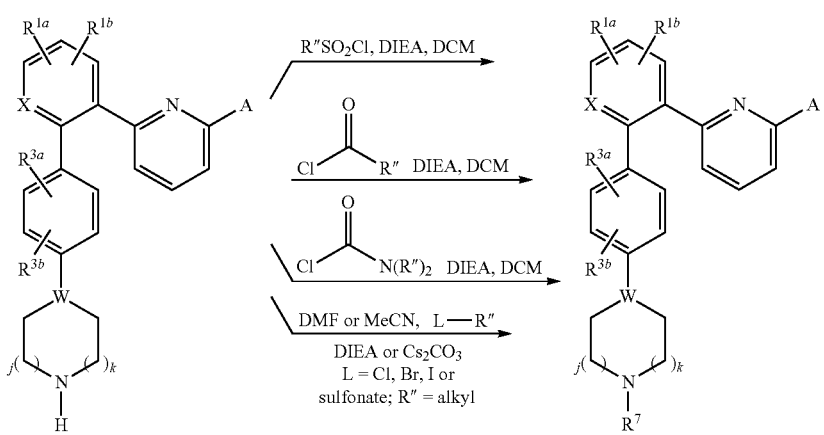

Additionally, as depicted in Scheme 16, wherein R$^{13}$ within A is C$_{1-6}$ alkyl, the amino group in 15b may be further elaborated by reaction with an appropriate aldehyde or ketone in the presence of a hydride reducing agent such as sodium (triacetoxy)borohydride and a protic acid such as acetic acid in an aprotic solvent such as DMF to provide alkyl amine 16a.

SCHEME 16

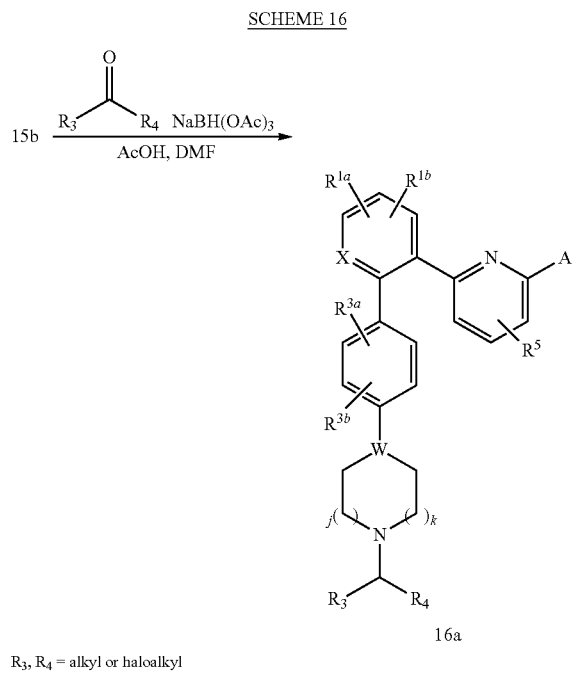

R$_3$, R$_4$ = alkyl or haloalkyl

As depicted in Scheme 17, the ester form of compounds of Formula I wherein R$^{13}$ is an alkyl group obtained by methods described above may be converted to their corresponding carboxylic acids under standard aqueous hydrolysis conditions. In one example, reaction of the ester with sodium hydroxide in a mixed solvent of dioxane, MeOH and water, often at ambient or slightly elevated temperature, provides the acid form of I wherein R$^{13}$ is H.

SCHEME 17

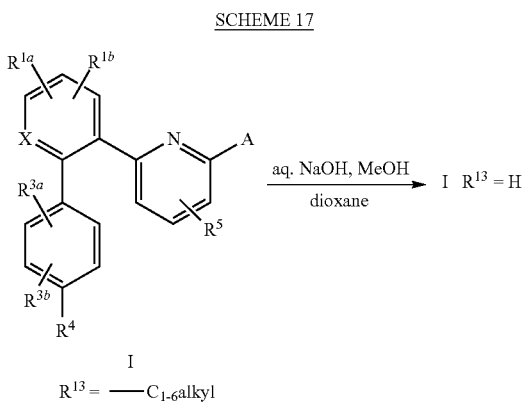

As will be known to those skilled in the art, in all schemes, the products of Formula I and all synthetic intermediates may be purified from unwanted side products, reagents and solvents by recrystallization, trituration, preparative thin layer chomatography, flash chomatography on silica gel as described by W. C. Still et al, J. Org. Chem. 1978, 43, 2923, or reverse-phase HPLC. Compounds purified by HPLC may be isolated as the corresponding salt.

Preparative HPLC, if not otherwise stated, was performed on either a YMC-Pack Pro C18 column (150×20 mm i.d.) or a Kromasil 100-10C8 column (100×30 mm i.d.) at an initial flow rate of 4-5 mL/min, followed by 15-20 mL/min. The gradients employed during the faster part of the run are described, and all runs were followed with a 100% organic wash. Flash chromatography on silica gel was performed using pre-packed silica gel columns on ISCO, Biotage Horizon or Biotage SP-1 instruments equipped with UV detectors.

Additionally, in some instances the final compounds of Formula I and synthetic intermediates may be comprised of a mixture of cis and trans isomers, enantiomers or diastereomers. As will be known to those skilled in the art, such cis and trans isomers, enantiomers and diastereomers may be separated by various methods including crystallization, chomatography using a homochiral stationary phase and, in the case of cis/trans isomers and diastereomers, normal-phase and reverse-phase chomatography.

Chemical reactions were monitored by LCMS, and the purity and identity of the reaction products were assayed by LCMS (electrospray ionization or ESI) and/or $^1$H NMR. Data for $^1$H NMR are reported with chemical shift (δ ppm), multiplicity (s=singlet, d=doublet, t=triplet, q=quartet, m=multiplet, br=broad; broad s=br s=broad singlet, br m=broad multiplet), coupling constant (J, or J, in Hz), and integration. Unless otherwise noted, all LCMS ions listed are [M+H]. All temperatures are degrees Celsius unless otherwise noted.

In the Examples, some intermediates and final compounds having a chiral carbon were prepared as racemates, and some chiral intermediates were resolved and the enantiomers were used separately to synthesize enantiomeric downstream intermediates and final products. In some cases racemic final products may have been resolved. In the instances where chiral compounds were separated by chiral HPLC purification, the term "enantiomer A" or "ent A" or "Ent A" and "enantiomer B" or "ent B" or "Ent B" are used to refer to the two different enantiomers and the downstream compounds derived from them respectively. The term "rac" refers to a racemic mixture. As a result, the chemical nomenclature may indicate that an S and/or an R enantiomer was obtained, but the absolute stereochemistry of the separate enantiomers A and/or B was not determined.

The following examples are provided so that the invention might be more fully understood. They should not be construed as forming the only genus that is considered as the invention nor limiting the invention in any way.

EXAMPLE 1A and 1B

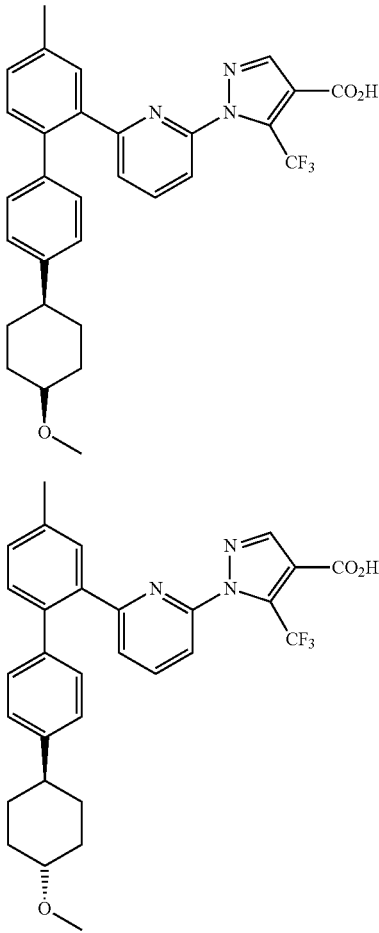

Step A. Ethyl 1-(6-chloropyridin-2-yl)-5-(trifluoromethyl)-1H-pyrazole-4-carboxylate

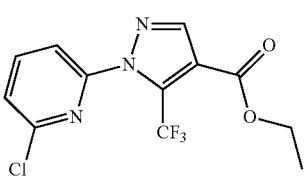 [SMILES: CCOC(=O)c1cnn(-c2cccc(Cl)n2)c1C(F)(F)F]

To a solution 2-chloro-6-hydrazinopyridine (1.00 g, 6.97 mmol) and triethylamine (971 mL, 6.97 mmol) in acetonitrile (35 mL) was added ethyl 2-(ethoxymethylene)-4,4,4-trifluoro-3-oxobutyrate (1.36 mL, 6.97 mmol). After 20 min, the reaction mixture was placed in a 60° C. oil bath. After 30 min, the reaction mixture was allowed to cool to ambient temperature, then was concentrated in vacuo. Purification by flash chromatography on silica gel (0 to 30% EtOAc in hexanes, then 30 to 100% EtOAc in hexanes) gave the title compound (PCT publication WO 2009/032249): LCMS m/z 319.9 [M+H]; $^1$H NMR (500 MHz, CDCl$_3$) δ 8.10 (s, 1 H),7.88 (t, J=7.5 Hz, 1 H),7.58 (d, J=8.0 Hz, 1 H),7.47 (d, J=8.0 Hz, 1 H),4.38 (q, J=7.0 Hz, 2 H), 1.38 (t, J=7.0 Hz, 3 H).

Step B. Ethyl 1-[6-(2-methoxy-5-methylphenyl)pyridin-2-yl]-5-(trifluoromethyl)-1H-pyrazole-4-carboxylate

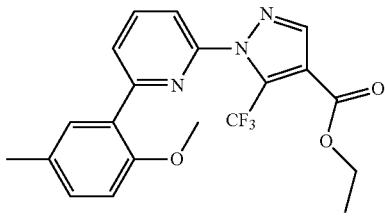 [SMILES: CCOC(=O)c1cnn(-c2cccc(-c3cc(C)ccc3OC)n2)c1C(F)(F)F]

To a flask containing the title compound from the above Step A (1.50 g, 4.69 mmol) were added 2-methoxy-5-methylphenyl boronic acid (0.779 g, 4.69 mmol) and dichloro bis(triphenylphosphine) palladium (0.33 g, 0.469 mmol). Acetonitrile (12 mL) and sodium carbonate (11.7 mL of 1.0 M aqueous solution, 11.7 mmol) were added, and the resulting mixture was degassed via nitrogen sparge. The reaction mixture was stirred at 70° C. for 18 h, then was allowed to cool to room temperature and was poured into water. The mixture was extracted with EtOAc, and the organic was concentrated in vacuo. Purification by chromatography on silica gel (0 to 20% EtOAc in hexanes, then 20 to 100% EtOAc in hexanes) provided the title compound: LCMS m/z 406.4 [M+H]$^+$; $^1$H NMR (500 MHz, CDCl$_3$) δ 8.12 (s, 1 H),8.11 (d, J=8.0 Hz, 1 H),7.91 (t, J=8.0 Hz, 1 H),7.77 (d, J=2.0 Hz, 1 H),7.52 (d, J=8.0 Hz, 1 H),7.19 (dd, J=8.0, 2.0 Hz, 1 H),6.91 (d, J=8.0 Hz, 1 H),4.39 (q, J=7.0 Hz, 2 H), 3.87 (s, 3 H),2.35 (s, 3 H),1.40 (t, J=7.0 Hz, 3 H).

Step C. Ethyl 1-[6-(2-hydroxy-5-methylphenyl)pyridin-2-yl]-5-(trifluoromethyl)-1-pyrazole-4-carboxylate

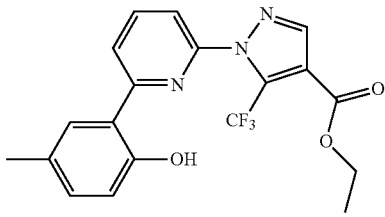 [SMILES: CCOC(=O)c1cnn(-c2cccc(-c3cc(C)ccc3O)n2)c1C(F)(F)F]

To a cooled (0° C.) solution of the title compound from the above Step B in DCM (20 mL) was added boron tribromide (11.7 mL of 1.0 M solution in DCM, 11.7 mmol). After 15 min, the reaction mixture was allowed to warm to ambient temperature. After an additional 2 h, the reaction mixture was cooled to 0° C., then was quenched by dropwise addition of sat. aq. NaHCO$_3$ (gas evolution) and was extracted with DCM. The organic phase was separated and concentrated in vacuo. Purification by flash chromatography on silica gel (0 to 30% EtOAc in hexanes, then 30 to 100% EtOAc in hexanes) provided the title compound: LCMS m/z 392.6 [M+H]$^+$; $^1$H NMR (500 MHz, CDCl$_3$) δ 11.78 (s, 1 H),8.17 (s, 1 H),8.07-8.03 (m, 2 H),7.60 (d, J=1.5 Hz, 1 H),7.48 (dd, J=7.0, 1.5 Hz, 1 H),7.17 (dd, J=8.0, 2.0 Hz, 1 H),6.94 (d, J=8.0 Hz, 1 H),4.39 (q, J=7.0 Hz, 2 H),2.36 (s, 3 H),1.40 (t, J=7.0 Hz, 3 H).

Step D. Ethyl 1-[6-(5-methyl-2-{(trifluoromethyl)sulfonyl]oxy}phenyl)pyridin-2-yl-5-(trifluoromethyl)-1H-pyrazole-4-carboxylate

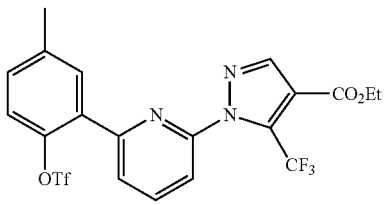 [SMILES: CCOC(=O)c1cnn(-c2cccc(-c3cc(C)ccc3OS(=O)(=O)C(F)(F)F)n2)c1C(F)(F)F]

To a cooled (−78° C.) solution of the title compound from the above Step C (2.05 g, 5.24 mmol) and pyridine (1.06 mL, 13.1 mmol) in DCM (50 mL) was added trifluoromethanesulfonic anhydride (1.06 mL, 6.29 mmol), then after 5 min the reaction mixture was allowed to warm to ambient temperature. After 20 min the mixture was quenched with 2 N aqueous HCl and the aqueous phase was extracted with hexanes:ethyl acetate (3:1 v/v). The organic phase was separated, dried over sodium sulfate, passed through a pad of silica gel, eluting with DCM, and concentrated in vacuo. The title compound was used without further purification: LCMS m/z 524.6 [M+H]$^+$; $^1$H NMR (500 MHz, CDCl$_3$) δ 8.14 (s, 1 H),8.02 (t, J=7.9 Hz, 1 H),7.81 (d, J=7.8 Hz, 1 H),7.71 (s, 1 H),7.68 (d, J=8.0 Hz, 1 H),7.30 (s, 2 H),4.39 (q, J=7.2 Hz, 2 H), 2.44 (s, 3 H),1.39 (t, J=7.2 Hz, 3 H).

Step E. Ethyl 1-[6-(4'-hydroxy-4-methylbiphenyl-2-yl)pyridin-2-yl]-5-(trifluoromethyl)-1H-pyrazole-4-carboxylate

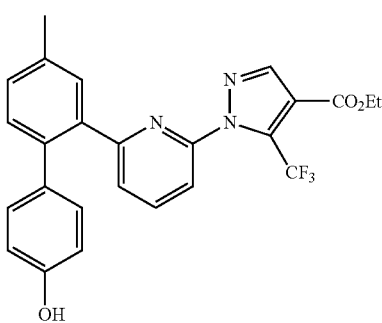 [SMILES: CCOC(=O)c1cnn(-c2cccc(-c3cc(C)ccc3-c3ccc(O)cc3)n2)c1C(F)(F)F]

To a flask containing the product from the above Step D (976 mg, 1.87 mmol) was added 4-hydroxyphenyl boronic acid (386 mg, 2.80 mmol) and 1,1'-bis(di-t-butylphosphino)ferrocene palladium dichloride (273 mg, 0.373 mmol). Acetonitrile (15 mL), cesium fluoride (284 mg, 1.87 mmol) and sodium carbonate (5.59 mL of 1.0 M aqueous solution, 5.59 mmol) were added, and the resulting mixture was degassed via nitrogen sparge. The reaction mixture was stirred at 90° C. for 3 h, then was allowed to cool to room temperature and was poured into water. The mixture was extracted with EtOAc, and the organic phase was concentrated in vacuo. Purification by chromatography on silica gel (0 to 25% EtOAc in hexanes, then 30 to 100% EtOAc in hexanes) provided the title compound: LCMS m/z 467.7 [M+H]; $^1$H NMR (500 MHz, acetone-d$_6$) δ 8.21 (s, 1 H),7.80 (t, J=7.8 Hz, 1 H),7.61 (d, J=7.9 Hz, 1 H),7.51 (s, 1 H), 7.31 (d, J=1.1 Hz, 2 H),7.02 (d, J=8, 1 H),6.98 (d, J=8.6 Hz, 2 H),6.76 (d, J=8.6, 2 H), 4.36 (q, J=7.1 Hz, 2 H),2.41 (s, 1 H),1.36 (t, J=7.1 Hz, 3 H).

Step F. Ethyl-[6-(4-methyl-4'-{[(trifluoromethyl)sulfonyl]oxy}biphenyl-2-yl)pyridin-2-yl]-5-(trifluoromethyl)-1H-pyrazole-4-carboxylate

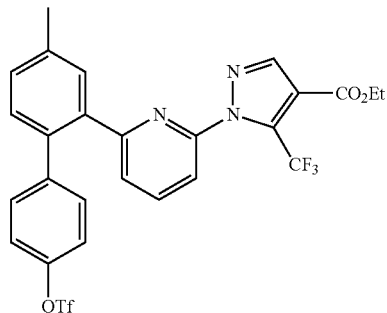 [SMILES: CCOC(=O)c1cnn(-c2cccc(-c3cc(C)ccc3-c3ccc(OS(=O)(=O)C(F)(F)F)cc3)n2)c1C(F)(F)F]

To a vial containing the product from the above Step E (203 mg, 0.43 mmol) in DCM, was added pyridine (0.09 mL, 1.08 mmol), then the reaction mixture was cooled to −78° C. in an ice bath. Subsequently, trifluoromethanesulfonic anhydride (0.11 mL, 0.18 mmol) was added dropwise. After stirring the reaction mixture for 5 min at −78° C. it was allowed to warm to ambient temperature and stirred for another 20 min. The reaction mixture was quenched with 2N HCl (aq) and the resultant mixture was extracted with DCM. The organic phase was collected and concentrated in vacuo. Purification by flash chromatography on silica gel (0 to 25% EtOAc in hexanes, then 25 to 100% EtOAc in hexanes) provided the title compound: LCMS m/z 599.7 [M+H]$^+$; $^1$H NMR (500 MHz, acetone-d$_6$) δ 8.19 (s, 1 H),7.88 (t, J=7.82, 1 H),7.86 (d, J=7.86 Hz, 1 H),7.55 (s, 1 H),7.40 (d, J=0.82 Hz, 2 H),7.37-7.32 (m, 4 H),7.15 (d, J=7.81, 1 H), 4.35 (q, J=7.12, 2 H),2.45 (s, 3 H),1.35 (t, J=7.14 Hz, 3 H).

Step G. 2-(4-Methoxycyclohex-1-en-1-yl)-4,4,5,5-tetramethyl-1,3,2-dioxaborolane

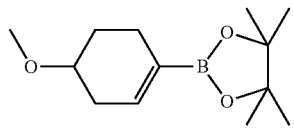

To a flask of 4-methoxycyclohexanone (2 g, 15.60 mmol) in THF (100 mL) cooled to −78° C. was added LHMDS (17.2 mL of 1 M LHMDS in THF, 17.2 mmol). The reaction mixture was aged for 5 min., then N-(5-chloropyridin-2-yl)-1,1,1-trifluoro-N—[(trifluoromethyl)sulfonyl]methanesulfonamide (6.13 g, 15.60 mmol) was added and the reaction mixture was allowed to slowly warm to ambient temperature overnight. The reaction mixture was then concentrated and purified by flash chromatography on silica gel (100% hexanes, then 0 to 15% DCM in hexanes, then 15% to 25% DCM in hexanes). This material was charged to a round bottomed flask with bis(pinacolato)diboron (2.80 g, 11.02 mmol), potassium acetate (3.15 g, 32.10 mmol), and 1,1'-bis(di t-butylphosphino)ferrocene palladium dichloride (0.153 g, 0.276 mmol). The flask was purged with nitrogen. Anhydrous 1,4-dioxane (50 mL) was added, and the resulting suspension was degassed via nitrogen sparge. The mixture was then placed in a pre-heated oil bath (80° C.), and was held at this temperature for 20 h, whereupon it was allowed to cool to ambient temperature, then the reaction mixture was diluted with hexanes (50 mL) and passed through a silica gel pad eluted by dichloromethane. The elutant was then concentrated and purified by flash chromatography on silica gel (15 to 35% DCM in hexanes, then 10 to 20% EtOAc in hexanes) to provide the title compound: $^1$H NMR (500 MHz, CD$_2$Cl$_2$) δ (ppm) 6.42 (s, 1 H),3.45 (m, 1 H),3.36 (s, 3 H),2.46 (m, 1 H),2.28 (m, 1 H),2.08 (m, 2 H),1.91 (m, 1 H), 1.54 (m, 1 H),1.26 (s, 12 H).

Step H. Ethyl 1-{6-[4'-(4-methoxycyclohex-1-en-1-yl-4-methylbiphenyl-2-yl]pyridin-2-yl}-5-(trifluoromethyl)-1H-pyrazole-4-carboxylate

Step I. Ethyl 1-{6-[4'-(trans-4-methoxycyclohexyl)-4-methylbiphenyl-2-yl]pyridin-2-yl}-5-(trifluoromethyl)-1H-pyrazole-4-carboxylate; Ethyl 1-{6-[4'-(cis-4-methoxycyclohexyl)-4-methylbiphenyl-2-yl]pyridin-2-yl}-5-(trifluoromethyl)-1H-pyrazole-4-carboxylate

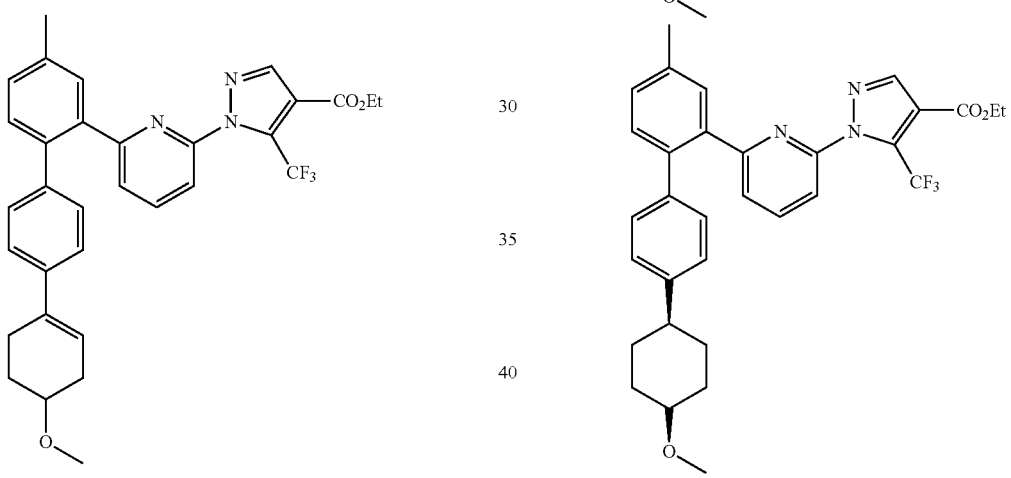

To a flask containing the title compound from the above Step F (240 mg, 0.40 mmol) was to added the title compound from the above Step G (143 mg, 0.60 mmol) and 1,1'-bis(di t-butylphosphino)ferrocene palladium dichloride (59 mg, 0.08 mmol). Acetonitrile (4 mL) and sodium carbonate (0.8 mL of 1.0 M aqueous solution, 0.8 mmol) were added, and the resulting mixture was degassed via nitrogen sparge. The reaction mixture was stirred at 120° C. for 1.5 h, then was allowed to cool to room temperature and was poured into water. The mixture was extracted with EtOAc, and the organic layer was concentrated in vacuo. Purification by chromatography on silica gel (0 to 25% EtOAc in hexanes, then 30 to 100% EtOAc in hexanes) provided the title compound: LCMS m/z 561.9 [M+H]$^+$; $^1$H NMR (500 MHz, (CD$_2$C2) δ 8.14 (s, 1 H),7.61 (t, J=7.8 Hz, 1 H),7.53 (s, 1 H),7.44 (d, J=7.8 Hz, 1 H),7.36-7.27 (m, 4H), 7.10 (d, J=8.2 Hz, 2 H),6.97 (d, J=7.8 Hz, 1 H),6.02 (m, 1 H),4.37 (q, J=7.2 Hz, 2 H),3.66-3.60 (m, 1 H),3.43 (s, 3 H),2.60-2.51 (m, 2 H),2.44 (m, 4 H),2.26-2.19 (m, 1 H),2.10-2.03 (m, 1 H),1.85-1.77 (m, 1 H),1.39 (t, J=7.2 Hz, 3 H).

To a degassed solution of the title compound from the above Step H (225 mg, 0.40 mmol) in EtOAc (10 mL) was added platinum(IV) oxide (67.4 mg, 30 wt %). The reaction flask was fitted with a 3-way adapter with a hydrogen balloon attached. The reaction flask was then evacuated and backfilled with hydrogen. After this process was repeated three times, the reaction mixture was stirred vigorously. After 30 min, the reaction mixture was filtered through Celite, rinsing with EtOAc. Purification by flash chromatography on silica gel (5 to 25% EtOAc in hexanes, then 25 to 100% EtOAc in hexanes) provided the separated cis and trans isomers: LCMS: cis isomer, m/z 563.9 [M+H]$^+$; trans isomer, m/z 563.9 [M+H]. $^1$H NMR (500 MHz, CD$_2$Cl$_2$) cis δ 8.12 (s, 1 H),7.58 (t, J=7.9 Hz, 1 H),7.54 (s, 1 H),7.44 (d, J=7.8 Hz, 1 H),7.34 (d, J=7.8 Hz, 1 H),7.31 (d, J=8.0 Hz, 1 H),7.12 (d, J=7.8, 1 H),7.06 (d, J=7.9 Hz, 1 H), 6.94 (d, J=7.7 Hz, 1 H),4.37 (q, J=7.1 Hz, 2 H),3.48 (s, 1 H),3.30 (s, 3 H),2.52 (t, J=12.0 Hz, 1 H),2.44 (s, 3 H),2.03 (d, J=13.6 Hz, 2 H),1.79-1.69 (m, 2 H),1.62-1.46 (m, 4 H),1.39 (t, J=7.1 Hz, 3 H).

Step J. 1-{6-[4'-(cis-4-methoxycyclohexyl)-4-methylbiphenyl-2-yl]pyridin-2-yl}-5-(trifluoromethyl)-1H-pyrazole-4-carboxylic acid (Example 1A); 1-{6-[4'-(trans-4-methoxycyclohexyl)-4-methylbiphenyl-2-yl]pyridin-2-yl}-5-(trifluoromethyl)-1H-pyrazole-4-carboxylic acid (Example 1B)

To a solution of the cis isomer of the title compounds from the above Step I (30.2 mg, 0.054 mmol) in 1,4-dioxane (0.5 mL) was added sodium hydroxide (0.11 mL, 1.0 M in water, 0.11 mmol), and the resulting mixture was stirred at 60° C. After 15 min, the reaction mixture was rendered acidic by addition of 2N trifluoroacetic acid in DMSO, then was diluted with dioxane/water 2:1 and passed through a 0.45 µm syringe filter. Purification by reverse phase HPLC (30 to 100% acetonitrile in water, each with 0.1% v/v TFA) provided the title compound of Example 1A: LCMS m/z 535.8 [M+H]$^+$; $^1$H NMR (500 MHz, CD$_2$Cl$_2$) δ 8.18 (s, 1 H),7.60 (t, J=7.82, 1 H),7.52 (s, 1 H),7.44 (d, J=7.84 Hz, 1 H),7.35-7.30 (m, 2 H),7.12 (d, J=8.1 Hz, 2 H),7.06 (d, J=8.16 Hz, 2 H),6.97 (d, J=7.82 Hz, 1 H),3.52-3.49 (m, 1 H),3.31 (s, 3 H), 2.54-2.49 (m, 1 H),2.43 (s, 3 H),2.03 (d, J=13.7 Hz, 2 H),1.74 (m, 2 H),1.61-1.48 (m, 4 H).

Utilization of the above procedure employing the trans isomer of the title compounds from the above Step I, gave the title compound of Example 1B: LCMS m/z 535.9 [M+H]$^+$; $^1$H NMR (500 MHz, CD$_2$Cl$_2$) δ 8.18 (s, 1 H),7.60 (t, J=7.89, 1 H),7.52 (s, 1 H),7.4 (d, J=7.80 Hz, 1 H),7.34-7.30 (m, 2 H),7.10 (d, J=8.30 Hz, 2 H),7.06 (d, J=8.30 Hz, 2 H),6.97 (d, J=7.80 Hz, 1 H),3.34 (s, 3 H),3.22-3.15 (m, 1 H),2.53-2.46 (m, 1 H),2.44 (s, 3 H),2.16 (d, J=11.21 Hz, 2 H),1.90 (d, J=12.66 Hz, 2 H),1.52-1.41 (m, 2 H),1.35-1.25 (m, 2 H).

EXAMPLE 2

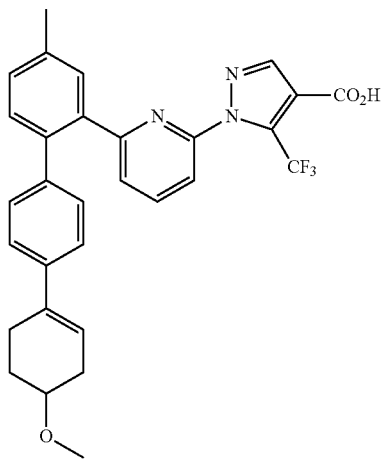 [SMILES: CCOC(=O)c1cnn(-c2cccc(-c3cc(C)ccc3-c3ccc(C4=CCC(OC)CC4)cc3)n2)c1C(F)(F)F]

1-{6-[4'-(4-methoxycyclohex-1-en-1-yl)-4-methylbiphenyl-2-yl]pyridin-2-yl}-5-(trifluoromethyl)-1H-pyrazole-4-carboxylic acid To a solution of the title compound from Example 1 Step H (49.6 mg, 0.09 mmol) in 1,4-dioxane (0.5 mL) was added sodium hydroxide (0.18 mL of 1.0 M solution in water, 0.18 mmol), and the resulting mixture was stirred at 60° C. After 15 min, the reaction mixture was rendered acidic by addition of 2N trifluoroacetic acid in DMSO, then was diluted with 2:1 dioxane:water and passed through a 0.45 µm syringe filter. Purification by reverse phase HPLC (30 to 100% acetonitrile in water, each with 0.1% v/v TFA) provided the title compound: LCMS m/z 533.9 [M+H]$^+$; $^1$H NMR (500 MHz, CD$_2$Cl$_2$) δ 8.21 (s, 1 H),7.61 (t, J=7.8, 1 H),7.54 (s, 1 H),7.46 (d, J=7.8 Hz, 1 H),7.37-7.27 (m, 4 H),7.10 (d, J=8.1 Hz, 2 H),6.98 (d, J=7.7 Hz, 1 H),6.04 (m, 1 H),3.59-3.52 (m, 1 H),3.38 (s, 3 H),2.59-2.51 (m, 2 H),2.44 (m, 4 H),2.24-2.16 (m, 1 H), 2.08-2.00 (m, 1 H),1.84-1.74 (m, 1 H).

EXAMPLE 3

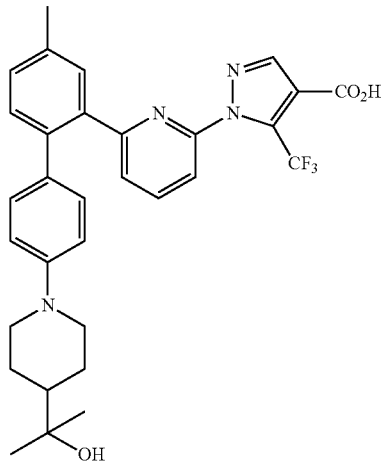 [SMILES: Cc1ccc(-c2ccc(N3CCC(C(C)(C)O)CC3)cc2)c(-c2cccc(-n3ncc(C(=O)O)c3C(F)(F)F)n2)c1]

1-(6-{4'-[4-(2-hydroxypropan-2-yl)piperidin-1-yl]-4-methylbiphenyl-2-yl}pyridin-2-yl)-5-(trifluoromethyl)-1H-pyrazole-4-carboxylic acid To a solution of the title compound from Example 1 Step F (58.5 mg, 0.10 mmol) in toluene (1.5 mL) were added 2-(piperidin-4-yl)propan-2-ol (30.0 mg, 0.15 mmol), tris(dibenzylidene acetone) dipalladium (0) (4.5 mg, 0.005 mmol), 2-(di-tert-butyl(phosphino)-2"-methylbiphenyl (3.1 mg, 0.01 mmol), and potassium phosphate tribasic (62.1 mg, 0.29 mmol). The resulting mixture was degassed via nitrogen sparge. The mixture was then placed in a pre-heated oil bath (85° C.), and was held at this temperature for 1 h, whereupon it was allowed to cool to ambient temperature, then was poured into water and then extracted with EtOAc. The organic phase was separated, dried over sodium sulfate, filtered through a silica plug, and concentrated in vacuo. The crude material was dissolved in 1,4-dioxane (0.5 mL) and a solution of sodium hydroxide (0.1 ml, 1.0 M in water, 0.1 mmol) was added, and the resulting mixture was stirred at 60° C. After 15 min, the reaction mixture was rendered acidic by addition of 2N trifluoroacetic acid in DMSO, then was diluted with a dioxane/water 2:1 mixture and passed through a 0.45 µm syringe filter. Purification by reverse phase HPLC (30 to 100% acetonitrile in water, each with 0.1% v/v TFA) provided the title compound: LCMS m/z 564.9 [M+H]$^+$; $^1$H NMR (500 MHz, CD$_2$Cl$_2$) δ 8.12 (s, 1 H),7.79 (t, J=7.9 Hz, 1 H),7.53 (s, 1 H),7.51 (d, J=7.9 Hz, 1 H),7.43 (d, J=7.7 Hz, 2 H),7.39-7.32 (m, 2 H),7.29-7.23 (m, 3 H),3.71 (d, J=11.8 Hz, 2 H),3.20 (m, 2 H),2.48 (s, 3 H),2.14-1.58 (m, 5 H),1.28 (s, 6 H).

EXAMPLE 4

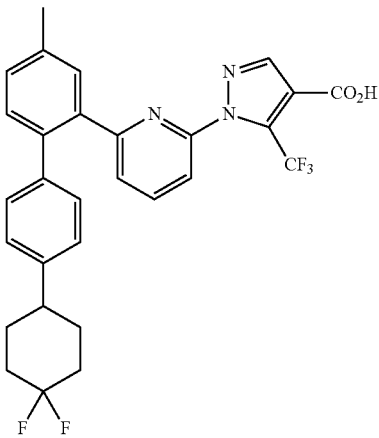 [SMILES: Cc1ccc(-c2ccc(C3CCC(F)(F)CC3)cc2)c(-c2cccc(-n3ncc(C(=O)O)c3C(F)(F)F)n2)c1]

Step A. 4-(4-Oxocyclohexyl)phenyl trifluoromethanesulfonate

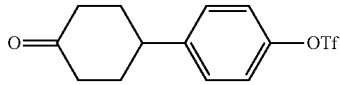 [SMILES: O=C1CCC(c2ccc(OS(=O)(=O)C(F)(F)F)cc2)CC1]

To a vial containing 4-(4-hydroxyphenyl)cyclohexanone (0.88 g, 4.61 mmol) in dichloromethane (15 mL), was added pyridine (1.12 mL, 13.8 mmol), and then reaction mixture was cooled to 0° C. Subsequently, triflic anhydride (1.01 mL, 5.99 mmol) was added dropwise. After stirring for 5 min the reaction mixture was allowed to warm to ambient temperature, then stirred for another 20 min. The reaction mixture was quenched with 2N HCl in water and then extracted with ethyl acetate. The organic phase was collected, dried over sodium sulfate, passed through a silica plug and concentrated in vacuo.: LCMS m/z 322.7 [M+H]$^+$; $^1$H NMR (500 MHz, acetone-d$_6$) δ 7.55 (d, J=8.6 Hz, 2 H),7.39 (d, J=8.8 Hz, 2 H),3.27-3.21 (m, 1 H),2.63-256 (m, 2 H),2.36-2.30 (m, 2 H),2.22-2.15 (m, 2 H),2.00-1.91 (m, 1 H).

Step B. Ethyl 1-{6-[5-methyl-2-(4,4,5,5-tetramethyl-1,3,2-dioxaborolan-2-yl)phenyl]pyridin-2-yl}-5-(trifluoromethyl-1H-pyrazole-4-carboxylate

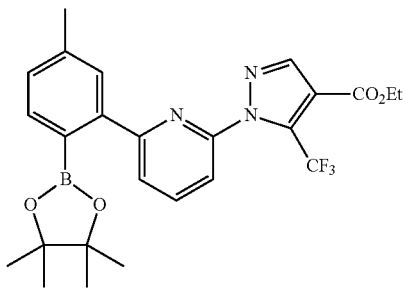 [SMILES: CCOC(=O)c1cnn(-c2cccc(-c3cc(C)ccc3B3OC(C)(C)C(C)(C)O3)n2)c1C(F)(F)F]

A round bottomed flask was charged with the title compound from Example 1 Step D (0.77 g, 1.47 mmol), bis(pinacolato)diboron (0.56 g, 2.21 mmol), potassium acetate (0.36 g, 3.68 mmol), and 1,1'-bis(di-t-butylphosphino)ferrocene palladium dichloride (0.22 g, 0.29 mmol). The flask was purged with nitrogen. Anhydrous ACN (15 mL) was added, and the resulting suspension was degassed via nitrogen sparge. The mixture was then placed in a pre-heated oil bath (80° C.), and was held at this temperature for 15 h, whereupon it was allowed to cool to ambient temperature, then was poured into water. The aqueous phase was extracted with ethyl acetate and the organic phase was washed with brine. The organic phase was then separated, dried over anhydrous sodium sulfate and concentrated in vacuo. Purification by chromatography on silica gel (0 to 30% EtOAc in hexanes, then 30 to 100% EtOAc in hexanes) provided the title compound: LCMS m/z 501.8 [M+H]$^+$; $^1$H NMR (500 MHz, CD$_2$Cl$_2$) δ 8.10 (s, 1 H),7.96 (t, J=7.9 Hz, 1 H),7.67 (d, J=7.7 Hz, 1 H),7.63 (d, J=7.5 Hz, 1 H),7.58 (d, J=7.9 Hz, 1 H),7.47 (s, 1 H),7.27 (d, J=7.3 Hz, 1 H),4.35 (q, J=7.2 Hz, 2 H),2.43 (s, 3 H),1.37 (t, J=7.2, 2 H), 1.09 (s, 12 H).

Step C. Ethyl 1-{6-[4-methyl-4'-(4-oxocyclohexyl)biphenyl-2-yl]pyridin-2-yl}-5-(trifluoromethyl)-1H-pyrazole-4-carboxylate

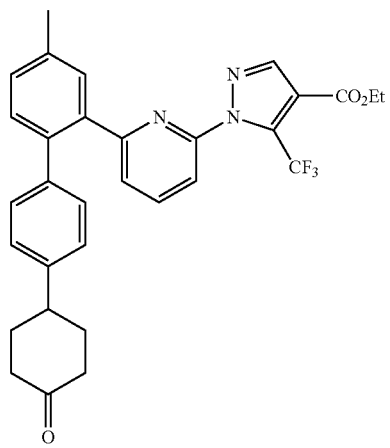 [SMILES: CCOC(=O)c1cnn(-c2cccc(-c3cc(C)ccc3-c3ccc(C4CCC(=O)CC4)cc3)n2)c1C(F)(F)F]

To a flask containing the title compound from the above Step B (28.7 mg, 0.06 mmol) were added the title compound from the above Step A (27.6 mg, 0.09 mmol) and 1,1'-bis(di t-butylphosphino)ferrocene palladium dichloride (6.28 mg, 0.008 mmol). 1,4-Dioxane (1 mL) and sodium carbonate (0.1 mL of 1.0 M aqueous solution, 0.1 mmol) were added, and the resulting mixture was degassed via nitrogen sparge. The reaction mixture was stirred at 80° C. for 15 h, then was allowed to cool to room temperature and was poured into water. The mixture was extracted with EtOAc, and the organic was concentrated in vacuo. Purification by chromatography on silica gel (0 to 25% EtOAcin hexanes, then 30 to 100% EtOAc in hexanes) provided the title compound: LCMS m/z 548.1 [M+H]$^+$; $^1$HNMR(500 MHz, acetone-d$_6$) δ 8.20 (s, 1 H),7.78 (t, J=7.8 Hz, 1 H),7.61 (d, J=8.0 Hz, 1 H),7.53 (s, 1 H),7.35 (s, 2 H),7.24 (d, J=8.1 Hz, 2 H),7.10 (d, J=8.2 Hz, 2 H),7.05 (d, J=7.9 Hz, 1 H),4.36 (q, J=7.1 Hz, 2 H), 3.14-3.04 (m, 1 H),2.61-2.51 (m, 2 H),2.34-2.26 (m, 2 H),2.18-2.10 (m, 2 H),1.96-1.86 (m, 2 H), 1.36 (t, J=7.1 Hz, 3 H).

Step D. 1-{6-[4'-(4,4-difluorocyclohexyl)-4-methyl-biphenyl-2-yl]pyridin-2-yl}-5-(trifluoromethyl)-1H-pyrazole-4-carboxylic acid A plastic vial was charged with a solution of the title compound from the above Step C (20.0 mg, 0.04 mmol) in DCM (0.75 mL). (Diethylamino)sulfur trifluoride (0.01 mL, 0.073 mmol) was added, and the resulting mixture was stirred at ambient temperature. After 1 h, the reaction mixture was quenched by addition of saturated aqueous sodium bicarbonate and was extracted with DCM. The organic phase was dried over anhydrous sodium sulfate, filtered through a silica plug and concentrated in vacuo. To a solution of the crude material in 1,4-dioxane (0.5 mL) was added sodium hydroxide (0.1 mL, 1.0 M in water, 0.1 mmol), and the resulting mixture was stirred at 60° C. After 15 min, the reaction mixture was rendered acidic by addition of 2N trifluoroacetic acid in DMSO, then was diluted with a 2:1 dioxane:water mixture and passed through a 0.45 μm syringe filter. Purification by reverse phase HPLC (30 to 100% acetonitrile in water, each with 0.1% v/v TFA) provided the title compound: LCMS m/z 541.8 [M+H]+; 1H NMR (500 MHz, acetone-d6) δ 8.21 (s, 1 H),7.78 (t, J=7.9 Hz, 1 H),7.61 (d, J=7.7 Hz, 1 H),7.53 (s, 1 H),7.35 (d, J=0.9 Hz, 2 H),7.19 (d, J=8.2 Hz, 2 H),7.10 (d, J=8.3 Hz, 2 H),7.04 (d, J=7.6 Hz, 1 H),2.76-2.68 (m, 1 H),2.43 (s, 3 H),2.18-2.09 (m, 2 H),1.99-1.98 (m, 4 H),1.79-1.68 (m, 2 H).

EXAMPLE 5

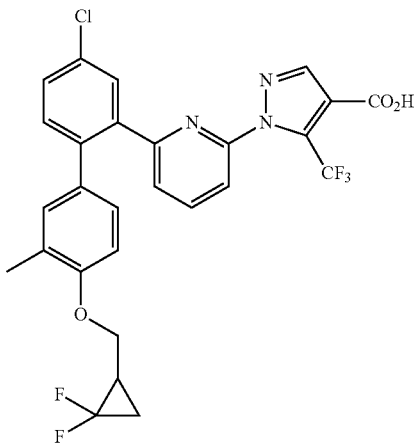 [SMILES: Cc1cc(-c2ccc(Cl)cc2-c2cccc(-n3ncc(C(=O)O)c3C(F)(F)F)n2)ccc1OCC1CC1(F)F]

Step A. Ethyl-1-(6-chloropyridin-2-yl)-5-trifluoromethyl-1H-pyrazole-4-carboxylate To a solution 2-chloro-6-hydrazinopyridine (1.00 g, 6.97 mmol) and triethylamine (0.971 mL, 6.97 mmol) in acetonitrile (35 mL) was added ethyl 2-(ethoxymethylene)-4,4,4-trifluoro-3-oxobutyrate (1.36 mL, 6.97 mmol). After 20 min, the reaction mixture was placed in a 60° C. oil bath. After 30 min, the reaction mixture was allowed to cool to ambient temperature, then was concentrated in vacuo. Purification by flash chromatography on silica gel (0 to 30% EtOAc in hexanes, then 30 to 100% EtOAc in hexanes) gave the title compound: LCMS m/z 319.9 [M+H]+; 1H NMR (500 MHz, CDCl3) δ 8.10 (s, 1 H),7.88 (t, J=7.5 Hz, 1 H),7.58 (d, J=8.0 Hz, 1 H),7.47 (d, J=8.0 Hz, 1 H),4.38 (q, J=7.0 Hz, 2 H),1.38 (t, J=7.0 Hz, 3 H).

Step B. Ethyl 1-[6-(2-hydroxylphenyl)pyridine-2-yl]-5-trifluoromethyl-1H-pyrazole-4-carboxylate To a flask containing the title compound from the above Step A (500 mg, 1.56 mmol) were added 2-hydroxyphenylboronic acid (237 mg, 1.72 mmol) and trans-dichlorobis (triphenylphosphine)palladium (II) (112 mg, 0.16 mmol). Acetonitrile (4 mL) and sodium carbonate (3.9 mL of 1.0 M aqueous solution, 3.9 mmol) were added, and the resulting mixture was degassed via nitrogen sparge. The reaction mixture was stirred at 70° C. for 3 h, then was allowed to cool to ambient temperature and was poured into water. The mixture was extracted with EtOAc, and the organic phase was concentrated in vacuo. Purification by chromatography on silica gel (0 to 30% EtOAc in hexanes, then 30 to 100% EtOAc in hexanes) provided the title compound: LCMS m/z 378.5 [M+H]+; 1H NMR (500 MHz, CDCl3) δ 12.02 (s, 1 H),8.18 (s, 1 H),8.09-8.04 (m, 2 H),7.82 (dd, J=8.0, 1.5 Hz, 1 H),7.50 (dd, J=7.5, 1.5 Hz, 1 H),7.38-7.34 (m, 1 H),7.06-7.03 (m, 1 H),6.99-6.95 (m, 1 H),4.40 (q, J=7.0 Hz, 2 H), 1.40 (t, J=7.0 Hz, 3 H).

Step C. Ethyl 1-[6-(5-chloro-2-hydroxyphenyl)pyridin-2-yl]-5-(trifluoromethyl)-1H-pyrazole-4-carboxylate

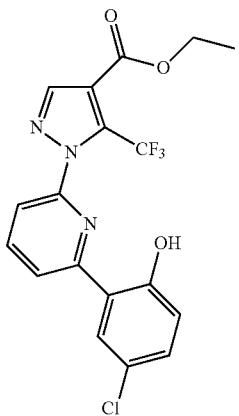 [SMILES: CCOC(=O)c1cnn(-c2cccc(-c3cc(Cl)ccc3O)n2)c1C(F)(F)F]

To a solution of the title compound from the above Step B (1.00 g, 2.65 mmol) in DCM (13 mL) was added benzyltrimethylammonium tetrachloroiodate (1.13 g, 2.70 mmol), and the resulting mixture was allowed to stir at room temperature. After 24 h, the mixture was concentrated in vacuo. Purification by chromatography on silica gel (0 to 100% EtOAc in hexanes) provided the title compound: LCMS m/z 412.0 [M+H]+; 1H NMR (500 MHz, CDCl3) 11.98 (s, 1 H),8.18 (s, 1 H),8.10 (t, J=8.0 Hz, 1 H),8.00 (d, J=8.0 Hz, 1 H),7.78 (br s, 1 H), 7.55 (d, J=8.0 Hz, 1 H),7.30 (dd, J=9.0, 2.0 Hz, 1 H),6.98 (d, J=9.0 Hz, 1 H),4.39 (q, J=7.0 Hz, 2 H),1.40 (t, J=7.0 Hz, 3 H).

Step D. Ethyl 1-[6-(5-chloro-2-{[(trifluoromethyl) sulfonyl]oxy}phenyl)pyridin-2-yl]-5-(trifluoromethyl)-1H-pyrazole-4-carboxylate

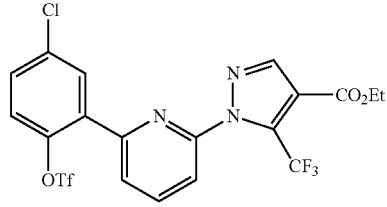 [SMILES: CCOC(=O)c1cnn(-c2cccc(-c3cc(Cl)ccc3OS(=O)(=O)C(F)(F)F)n2)c1C(F)(F)F]

To a vial containing the product from the above Step C (10.0 g, 24.3 mmol) in DCM (30 mL) was added pyridine (4.90 mL, 60.7 mmol), and then reaction mixture was cooled to 0° C. Subsequently, trifluoromethanesulfonic anhydride (5.74 mL, 34.00 mmol) was added dropwise. After stirring the reaction mixture for 5 min it was allowed to warm to ambient temperature, then stirred for another 20 min. The reaction mixture was quenched with 2N HCl in water and then extracted with DCM. The organic phase was collected and concentrated in vacuo. Purification by flash chromatography on silica gel (0 to 25% EtOAc in hexanes, then 25 to 100% EtOAc in hexanes) provided the title compound: LCMS m/z 543.8 [M+H]+; $^1$H NMR (500 MHz, acetone-$d_6$) δ 8.34 (t, J=7.9 Hz, 1 H),8.24 (s, 1 H),8.05 (d, J=7.8 Hz, 1 H),7.96-7.93 (m, 2 H),7.73 (dd, J=8.9, J=2.7 Hz, 1 H),7.66 (d, J=8.8 Hz, 1 H),4.36 (q, J=7.1 Hz, 2 H),1.35 (t, J=7.2 Hz, 3 H).

Step E. Ethyl 1-{6-[4'-(benzyloxy-4-chloro-3'-methylbiphenyl-2-yl]pyridin-2-yl}-5-(trifluoromethyl)-1H-pyrazole-4-carboxylate

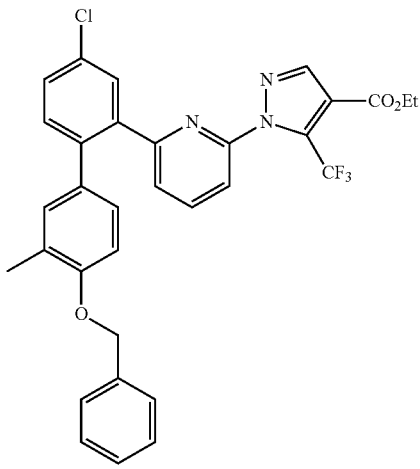 [SMILES: CCOC(=O)c1cnn(-c2cccc(-c3cc(Cl)ccc3-c3ccc(OCc4ccccc4)c(C)c3)n2)c1C(F)(F)F]

To a flask containing the product from the above Step D (2.11 g, 3.88 mmol) were added [4-(benzyloxy)-3-methylphenyl]boronic acid (1.410 g, 5.83 mmol) and dichloro bis(triphenylphosphine)palladium (0.41 g, 0.58 mmol). Acetonitrile (25 mL) and sodium carbonate (7.77 mL of 1.0 M aqueous solution, 7.77 mmol) were added, and the resulting mixture was degassed via nitrogen sparge. The reaction mixture was stirred at 80° C. for 48 h, then was allowed to cool to room temperature and was poured into water. The mixture was extracted with EtOAc, and the organic phase was concentrated in vacuo. Purification by chromatography on silica gel (0 to 25% EtOAc in hexanes, then 30 to 100% EtOAc in hexanes) provided the title compound: LCMS m/z 591.9 [M+H]+; $^1$H NMR (500 MHz, CDCl$_3$) δ 8.15 (s, 1 H),7.74 (d, J=2.2 Hz, 1 H),7.59 (t, J=7.9 Hz, 1 H),7.48-7.31 (m, 8 H),6.98 (d, J=1.8 Hz, 1 H),6.93 (d, J=7.7 Hz, 1 H),6.87 (dd, J=8.4, 2.2 Hz, 1 H),6.77 (d, J=8.4 Hz, 1 H),5.06 (s, 2 H),4.40 (q, J=7.1 Hz, 2 H),2.21 (s, 3 H),1.40 (t, J=7.2 Hz, 3 H).

Step F. Ethyl 1-[6-(4-chloro-4'-hydroxy-3'-methylbiphenyl-2-yl)pyridin-2-yl]-5-(trifluoromethyl)-1H-pyrazole-4-carboxylate

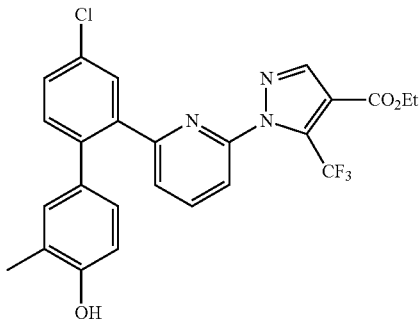 [SMILES: CCOC(=O)c1cnn(-c2cccc(-c3cc(Cl)ccc3-c3ccc(O)c(C)c3)n2)c1C(F)(F)F]

To a degassed solution of the title compound from the above Step E (2.29 g, 3.88 mmol) in a mixture of EtOAc (12 mL) and EtOH (3 mL) was added 10% Pd on carbon (687 mg). The reaction flask was fitted with a 3-way adapter with a hydrogen balloon attached. The reaction flask was then evacuated and back-filled with hydrogen. After this process was repeated three times, the reaction mixture was stirred vigorously. After 1.5 h, the reaction mixture was filtered through celite, rinsing with EtOAc. The filtrate and washings were concentrated and the crude is material was used without further purification. LCMS m/z 501.9 [M+H]+; $^1$H NMR (500 MHz, CDCl$_3$) δ 8.13 (s, 1 H),7.71 (d, J=2.2 Hz, 1 H),7.59 (t, J=7.9 Hz, 1 H),7.45 (d, J=7.7 Hz, 1 H), 7.41 (dd, J=8.2, 2.3 Hz, 1 H),7.32 (d, J=8.2 Hz, 1 H),6.93-6.90 (m, 2 H),6.80 (dd, J=8.2, 2.2 Hz, 1 H),6.64 (d, J=8.2 Hz, 1 H),4.38 (q, J=7.2 Hz, 2 H),2.16 (s, 3 H),1.39 (t, J=7.1 Hz, 3 H).

Step G. 1-(6-{4-Chloro-4'-[(2,2-difluorocyclopropyl) methoxy]-3'-methylbiphenyl-2-yl}pyridin-2-yl)-5-(trifluoromethyl)-1H-pyrazole-4-carboxylic acid To a solution of the title compound from the above Step F (32.2 mg, 0.06 mmol) and 2-(bromomethyl)-1,1-difluorocyclopropane (21.9 mg, 0.13 mmol) in DMF (1 mL) was added cesium carbonate (41.8 mg, 0.13 mmol), and the resulting mixture was stirred for 30 minutes at 60° C. The mixture was quenched by addition of 2N HCl. The aqueous phase was extracted with ethyl acetate, and the organic phase was dried over sodium sulfate, and concentrated in vacuo. To a solution of the crude material in 1,4-dioxane (0.5 mL) was added sodium hydroxide (0.1 mL of 1.0 M solution in water, 0.1 mmol), and the resulting mixture was stirred at 60° C. After 15 min, the reaction mixture was rendered acidic by addition of 2N trifluoroacetic acid in DMSO, then was diluted with a mixture of 2:1 dioxane:water and passed through a 0.45 μm syringe filter. Purification by reverse phase HPLC (30 to 100% acetonitrile in water, each with 0.1% v/v TFA) provided the title compound: LCMS m/z 563.9 [M+H]+; $^1$H NMR (500 MHz, CD$_2$Cl$_2$) δ 8.21 (s, 1 H),7.70 (d, J=2.1 Hz, 1 H),7.65 (t, J=7.8 Hz, 1 H),7.50 (d, J=8.0 Hz, 1 H),7.47-7.44 (m, 1 H),7.38 (d, J=8.3 Hz, 1 H),7.00-6.96 (m, 2 H),6.89 (d, J=8.0 Hz, 1 H),6.71 (d, J=8.5 Hz, 1 H),4.10-3.98 (m, 2 H),2.16 (s, 3 H),2.13-2.04 (m, 1 H),1.64-1.55 (m, 1 H),1.34-126 (m, 1 H).

EXAMPLE 6

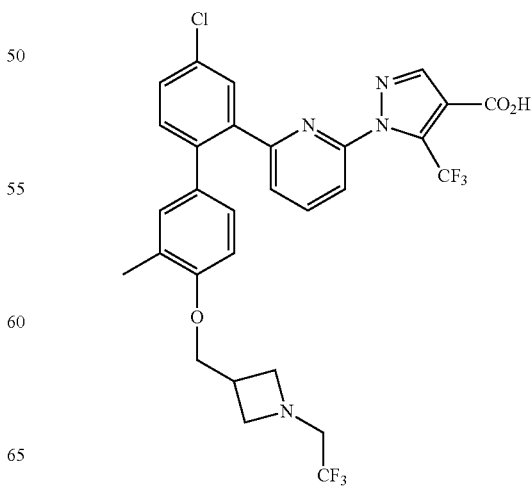

Step A. Ethyl 1-{6-[4'(azetidin-3-ylmethoxy)-4-chloro-3'-methylbiphenyl-2-yl]pyridin-2-yl}-5-(trifluoromethyl)-1H-pyrazole-4-carboxylate

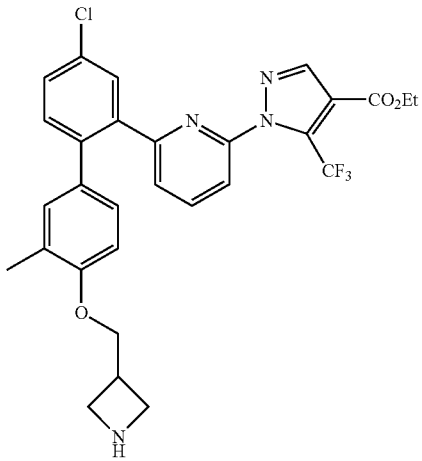 [SMILES: CCOC(=O)c1cnn(-c2cccc(-c3cc(Cl)ccc3-c3ccc(OCC4CNC4)c(C)c3)n2)c1C(F)(F)F]

To a solution of the title compound of Example 5 Step F (214 mg, 0.43 mmol) and tert-butyl 3-(hydroxymethyl)azetidine-1-carboxylate (120 mg, 0.64 mmol) in 1,4-dioxane were added triphenylphosphine (168 mg, 0.64 mmol), followed by diisopropyl azodicarboxylate (0.12 mL, 0.64 mmol). The vial was capped and stirred at 60° C. After 1.5 h, the reaction mixture was allowed to cool to ambient temperature, quenched with water and the aqueous phase was extracted with ethyl acetate. The organic phase was dried over sodium sulfate and concentrated in vacuo. The residue was purified by chromatography on silica gel (0 to 25% EtOAc in hexanes, then 30 to 100% EtOAc) to provide the N-Boc protected azetidine compound. Subsequently the deprotection was carried out by dissolving the Boc protected intermediate in DCM (5 mL) followed by the addition of 1 mL of trifluoroacetic acid and stirring for 20 min. The reaction mixture was then concentrated and the remaining trifluoroacetic acid was azeotroped three times with toluene. The resulting crude azetidine TFA salt was used without further purification: LCMS m/z 570.9 [M+H]$^+$; $^1$H NMR (500 MHz, CDCl$_3$) δ 8.14 (s, 1 H), 7.72 (d, J=2.2 Hz, 1 H), 7.62 (t, J=7.9 Hz, 1 H), 7.47 (d, J=7.7 Hz, 1 H), 7.43 (dd, J=8.3, 2.3 Hz, 1 H), 7.33 (d, J=8.2 Hz, 1 H), 7.00 (d, J=1.9 Hz, 1 H), 6.94 (d, J=7.8 Hz, 1 H), 6.88 (dd, J=8.4, 2.3 Hz, 1 H), 6.67 (d, J=8.4 Hz, 1 H), 4.97 (br, s, 1 H), 4.39 (q, J=7.1 Hz, 2 H), 4.22 (s, 4 H), 4.08 (d, J=4.8 Hz, 2 H), 2.18 (s, 3 H), 1.40 (t, J=7.2 Hz, 3 H), 1.30 (m, 1 H).

Step B. 1-[6-(4-Chloro-3'-methyl-4'-{[1-(2,2,2-trifluoroethyl)azetidin-3-yl]methoxy}biphenyl-2-yl)pyridin-2-yl]-5-(trifluoromethyl)-1H-pyrazole-4-carboxylic acid To a solution of the title compound from the above Step A (40.3 mg, 0.07 mmol) and 2,2,2-trifluoroethyl trifluoromethanesulfonate (24.6 mg, 0.11 mmol) in acetonitile (1 mL) was added DIEA (0.02 mL, 0.14 mmol), and the resulting mixture was stirred at 50° C. for 30 min. The mixture was concentrated in vacuo. To a solution of the crude material in 1,4-dioxane (0.5 mL) was added sodium hydroxide (0.2 mL of 1.0 M solution in water, 0.2 mmol), and the resulting mixture was stirred at 60° C. After 15 min, the reaction mixture was rendered acidic by addition of 2N trifluoroacetic acid in DMSO, then was diluted with a dioxane/water 2:1 mixture and passed through a 0.45 μm syringe filter. Purification by reverse phase HPLC (30 to 100% acetonitrile in water, each with 0.1% v/v TFA) provided the title compound:

LCMS m/z 625.0 [M+H]$^+$; $^1$H NMR (500 MHz, acetone-d$_6$) δ 8.23 (s, 1 H), 7.86 (t, J=7.9 Hz, 1 H), 7.71-7.67 (m, 2 H), 7.54 (dd, J=8.2 Hz, 2.3 Hz, 1 H), 7.41 (d, J=8.4 Hz, 1 H), 7.09 (d, J=7.8 Hz, 1 H), 7.00 (s, 1 H), 6.94 (dd, J=8.4 Hz, J=2.2 Hz, 1 H), 6.87 (d, J=8.4 Hz, 1 H), 4.18 (d, J=6.1 Hz, 2 H), 3.96 (m, 2 H), 3.75 (m, 2 H), 3.59 (m, 2 H), 3.20 (m, 1 H), 2.14 (s, 3 H).

EXAMPLE 7

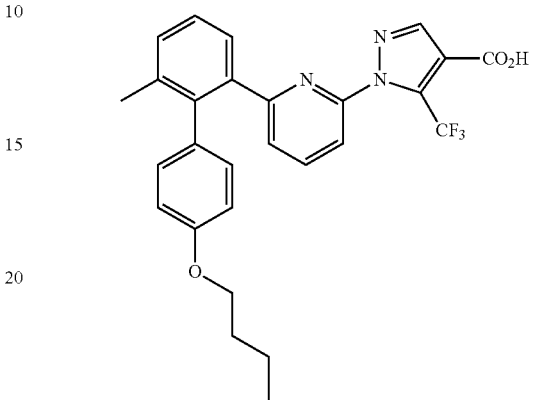

Step A. Ethyl 1-[6-(2-hydroxy-3-iodophenyl)pyridin-2-yl]-5-(trifluoromethyl)-1H-pyrazole-4-carboxylate

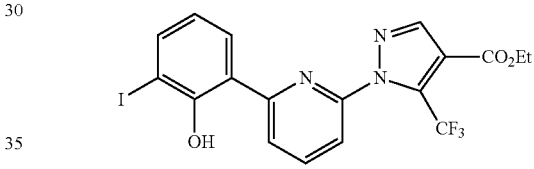

To a suspension of the title compound from Example 5 Step B (4.0 g, 10.6 mmol) and silver sulfate (3.31 g, 10.6 mmol) in ethanol (20 mL) was added iodine (2.69 g, 10.6 mmol), and the resulting mixture was vigorously stirred at room temperature. After 2 h, the reaction mixture was quenched with water and sodium bisulfite solution, extracted with ethyl acetate and concentrated in vacuo. Purification by chromatography on silica gel (0 to 15% EtOAc in hexanes, then 15 to 100% EtOAc in hexanes) provided the title compound: LCMS m/z 503.7 [M+H]$^+$; $^1$H NMR (500 MHz, CDCl$_3$) δ 13.08 (s, 1 H), 8.17 (s, 1 H), 8.10 (t, J=8.0 Hz, 1 H), 8.06 (d, J=8.0 Hz, 1 H), 7.86 (dd, J=7.5, 1.5 Hz, 1 H), 7.82 (dd, J=8.0, 1.5 Hz, 1 H), 7.52 (d, J=7.5 Hz, 1 H), 6.75 (t, J=8.0 Hz, 1 H), 4.33 (q, J=7.0 Hz, 2 H), 1.43 (t, J=7.0 Hz, 3 H).

Step B. Ethyl 1-(6-(2-hydroxy-3-methylphenyl)pyridin-2-yl)-5-(trifluoromethyl-1H-pyrazole-4-carboxylate

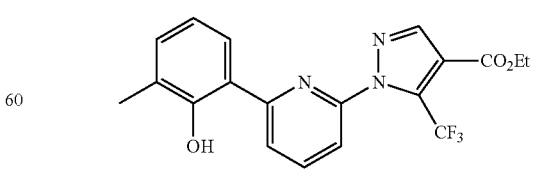

To a solution of the title compound from the above Step A (1.22 g, 2.24 mmol) in DMF (10 mL) were added iodomethane (0.23 mL, 3.64 mmol) and cesium carbonate (1.58 g, 4.85 mmol). The resulting mixture was stirred at ambient temperature for 1 h, then the reaction mixture was poured into sodium bicarbonate and extracted with ethyl acetate. The combined organic phase was dried with sodium sulfate and concentrated in vacuo. A round bottomed flask was charged with the crude material, trimethylboroxine (3.04 g, 12.1 mmol) and 1,1'-bis(di-t-butylphosphino)ferrocene palladium dichloride (0.20 g, 0.24 mmol). The flask was purged with nitrogen. Anhydrous 1,4 dioxane (10 mL) and sodium carbonate (3.9 mL of 1.0 M aqueous solution, 3.9 mmol) were added, and the resulting suspension was degassed via nitrogen sparge. The mixture was then placed in a pre-heated oil bath (65° C.), and was held at this temperature for 18 h, whereupon it was allowed to cool to ambient temperature, then was poured into water. The aqueous phase was extracted with ethyl acetate and the organic phase was washed with brine, dried over anhydrous sodium sulfate and concentrated in vacuo. Purification by flash chromatography on silica gel (0 to 25% EtOAc in hexanes, then 25 to 100% EtOAc in hexanes) provided the methyl ether. Lastly, to a cooled (0° C.) solution of the protected compound in DCM (10 mL), was added boron tribromide (6.1 mL of a 1.0 M solution in DCM, 6.1 mmol). After 30 min the reaction mixture was allowed to warm to ambient temperature, whereupon it was stirred. After 2 h the reaction was quenched using sodium bicarbonate, extracted with DCM, filtered through a silica plug and concentrated in vacuo. The resulting ortho methyl product was used without further purification. LCMS m/z 391.8 [M+H]$^+$; $^1$H NMR (500 MHz, CDCL$_3$) δ 12.34 (s, 1 H),8.18 (s, 1 H),8.07-8.03 (m, 2 H),7.67 (d, J=8.0 Hz, 1 H),7.48-7.46 (m, 1H), 7.23 (d, J=7.5 Hz, 1 H),6.87 (d, t, J=7.5 Hz, 1 H),4.40 (q, J=7.0 Hz, 2 H),2.29 (s, 3 H), 1.40 (t, J=7.0 Hz, 3 H).

Step C. Ethyl 1-[6-(3-methyl-2-{[(trifluoromethyl)sulfonyl]oxy}phenyl)pyridin-2-yl]-5-(trifluoromethyl)-1H-pyrazole-4-carboxylate

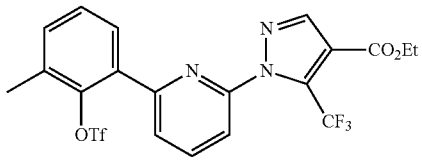 [SMILES: CCOC(=O)c1cnn(-c2cccc(-c3cccc(C)c3OS(=O)(=O)C(F)(F)F)n2)c1C(F)(F)F]

To a vial containing the product from the above Step B (0.20 g, 0.51 mmol) in DCM (20 ml), was added pyridine (0.10 mL, 0.13 mmol), and the reaction mixture was cooled to −78° C. Subsequently, trifluoromethanesulfonic anhydride (0.11 mL, 0.66 mmol) was added dropwise. After stirring the reaction mixture for 5 min it was allowed to warm to ambient temperature, then stirred for another 20 min. The reaction mixture was quenched with 2N HCl in water and then extracted with DCM. The organic phase was collected and concentrated in vacuo. Purification by flash chromatography on silica gel (0 to 25% EtOAc in hexanes, then 25 to 100% EtOAc in hexanes) provided the title compound: LCMS m/z 523.7 [M+H]$^+$; $^1$H NMR (500 MHz, CD$_2$Cl$_2$) δ 8.12 (s, 1 H),8.03 (t, J=7.9 Hz, 1 H),7.72 (d, J=7.5 Hz, 1 H),7.70 (d, J=8.0 Hz, 1 H),7.61 (t, J=4.8 Hz, 1 H),7.43 (d, J=4.9 Hz, 2 H),4.36 (q, J=7.2 Hz, 2 H),2.50 (s, 3 H),1.37 (t, J=7.2 Hz; 3 H).

Step D. 1-[6-(4'-butoxy-6-methylbiphenyl-2-yl)pyridin-2-yl]-5-(trifluoromethyl)-1H-pyrazole-4-carboxylic acid To a flask containing the title compound from the above Step C (55.1 mg, 0.11 mmol) was added (4-butoxyphenyl)boronic acid (30.6 mg, 0.16 mmol) and dichloro bis(triphenylphosphine) palladium (17.0 mg, 0.02 mmol). Acetonitrile (1.5 mL) and sodium carbonate (0.21 mL of 1.0 M aqueous solution, 0.21 mmol) were added, and the resulting mixture was degassed via nitrogen sparge. The reaction mixture was stirred at 80° C. for 1 h, then was allowed to cool to room temperature and was poured into water. The mixture was extracted with EtOAc, and the organic was concentrated in vacuo. To a solution of the crude material in 1,4-dioxane (0.5 mL) was added sodium hydroxide (0.1 mL of 1.0 M solution in water, 0.1 mmol), and the resulting mixture was stirred at 60° C. After 15 min, the reaction mixture was rendered acidic by addition of 2N trifluoroacetic acid in DMSO, then was diluted with a dioxane/water 2:1 mixture and passed through a 0.45 am syringe filter. Purification by reverse phase HPLC (30 to 100% acetonitrile in water, each with 0.1% v/v TFA) provided the title compound: LCMS m/z 495.8 [M+H]$^+$; $^1$H NMR (500 MHz, acetone-d$_6$) δ 8.18 (s, 1 H),7.74 (t, J=7.8 Hz, 1 H),7.56-7.49 (m, 2 H),7.40-7.35 (m, 2 H),7.02-6.99 (m, 3 H),6.86-6.83 (m, 2H), 3.96 (t, J=6.6 Hz, 2 H),2.18 (s, 3 H),1.77-1.70 (m, 2 H),1.53-1.44 (s, 2 H),0.96 (t, J=7.5 Hz, 3 H).

EXAMPLE 8

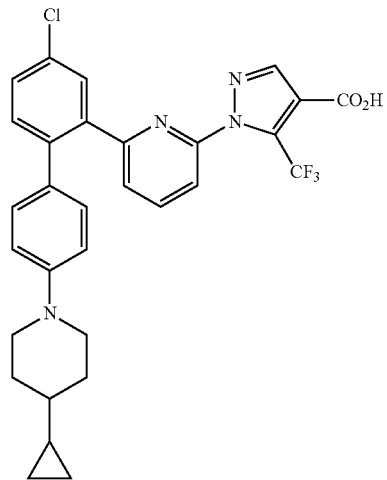 [SMILES: O=C(O)c1cnn(-c2cccc(-c3cc(Cl)ccc3-c3ccc(N4CCC(C5CC5)CC4)cc3)n2)c1C(F)(F)F]

Step A. Ethyl 1-{6-[5-chloro-2-(4,4,5,5-tetramethyl-1,3,2-dioxaborolan-2-yl)phenyl]pyridin-2-yl}-5-(trifluoromethyl)-1H-pyrazole-4-carboxylate

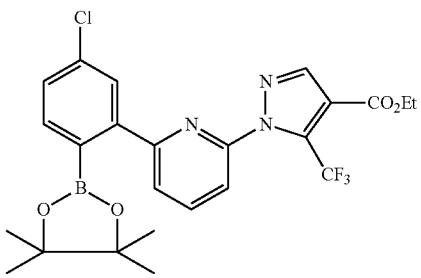 [SMILES: CCOC(=O)c1cnn(-c2cccc(-c3cc(Cl)ccc3B3OC(C)(C)C(C)(C)O3)n2)c1C(F)(F)F]

A round bottomed flask was charged with the title compound from Example 5 Step D (0.61 g, 1.12 mmol), bis (pinacolato)diboron (0.43 g, 1.68 mmol), potassium acetate (0.27 g, 2.8 mmol), and 1,1'-bis(di t-butylphosphino)ferrocene palladium dichloride (0.16 g, 0.22 mmol). The flask was purged with nitrogen. Anhydrous ACN (15 mL) was added, and the resulting suspension was degassed via nitrogen sparge. The mixture was then placed in a pre-heated oil bath (80° C.), and was held at this temperature for 1.5 h, whereupon it was allowed to cool to ambient temperature, then was poured into water. The aqueous phase was extracted with ethyl acetate and the organic phase was washed with brine. The organic phase was then dried over anhydrous sodium sulfate and concentrated in vacuo. Purification by flash chromatography on silica gel (0 to 100% EtOAc in hexanes) provided the title compound: LCMS m/z 521.8 [M+H]$^+$; $^1$H NMR (500 MHz, CD$_2$Cl$_2$) d 8.10 (s, 1 H),7.99 (t, J=7.8 Hz, 1 H),7.71-7.63 (m, 4H), 7.43 (dd, J=8.0, 1.9 Hz, 1 H),4.35 (q, J=7.1, 2 H),137 (t, J=7.2 Hz, 3 H),1.09 (s, 12 H).

Step B. 1-(4-bromophenyl)-4-cyclopropylpiperidine

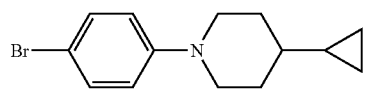 [SMILES: Brc1ccc(N2CCC(C3CC3)CC2)cc1]

A round bottomed flask was charged with 1-bromo-4-fluorobenzene (1.93 g, 11.0 mmol), 4-cyclopropylpiperidine (1.65 g, 13.2 mmol) and DIEA (7.67 g, 44.0 mmol). The flask was purged with nitrogen. Anhydrous 1-methyl-2-pyrrolidinone (25 mL) was added, and the resulting mixture was degassed via nitrogen sparge. The mixture was then placed in a pre-heated oil bath (180° C.), and was held at this temperature for 2 days, whereupon it was allowed to cool to ambient temperature, then was poured into water. The aqueous phase was extracted with ethyl acetate and the organic phase was washed with brine. The organic phase was then dried over anhydrous sodium sulfate and concentrated in vacuo. Purification by chromatography on silica gel (0 to 100% EtOAc in hexanes) provided the title compound: LCMS m/z 281.8 [M+H]$^+$; $^1$H NMR (500 MHz, CD$_2$Cl$_2$) δ 7.30 (d, J=8.8 Hz, 2 H),6.79 (d, J=8.8 Hz, 2 H),3.62 (d, J=12.2 Hz, 2 H),2.62 (t, J=12.1 Hz, 2 H),1.83 (d, J=12.8 Hz, 2 H),1.56-1.42 (m, 2 H),0.69-0.53 (m, 2 H),0.41 (d, J=7.5 Hz, 2 H),0.11 (d, J=4.5 Hz, 2 H).

Step C. 1-{6-[4-chloro-4'-(4-cyclopropylpiperidin-1-yl)biphenyl-2-yl]pyridin-2-yl}-5-(trifluoromethyl)-1H-pyrazole-4-carboxylic acid To a flask containing the title compound from the above Step A (19.9 mg, 0.04 mmol) were added the title compound from the above Step B (16.0 mg, 0.06 mmol) and 1,1'-bis(di t-butylphosphino)ferrocene palladium dichloride (5.58 mg, 0.008 mmol). Dioxane (1 mL) and sodium carbonate (0.08 mL of a 1.0 M aqueous solution, 0.08 mmol) were added, and the resulting mixture was degassed via nitrogen sparge. The reaction mixture was stirred at 80° C. for 48 h, then was allowed to cool to room temperature and was poured into water. The mixture was extracted with EtOAc, and the organic was concentrated in vacuo. The crude material was taken up in 1,4-dioxane (0.5 mL) and sodium hydroxide (0.1 mL of a 1.0 M solution in water, 0.1 mmol) was added, and the resulting mixture was stirred at 60° C. After 15 min, the reaction mixture was rendered acidic by addition of 2N trifluoroacetic acid in DMSO, then was diluted with a dioxane/water 2:1 mixture and passed through a 0.45 µm syringe filter. Purification by reverse phase HPLC (30 to 100% acetonitrile in water, each with 0.1% v/v TFA) provided the title compound: LCMS m/z 566.7 [M+H]$^+$; $^1$H NMR (500 MHz, acetone-d$_6$) δ 8.22 (s, 1 H), 7.86 (t, J=7.9 Hz, 1 H),7.71 (d, J=2.1 Hz, 1 H),7.68 (d, J=8.0 Hz, 1 H),7.53 (dd, J=8.3, 2.1 Hz, 1 H),7.46 (d, J=8.2 Hz, 1 H),7.11 (d, J=8.5 Hz, 1 H),7.06 (d, J=8.7 Hz, 2 H),6.99 (d, J=8.4 Hz, 2 H),3.73 (d, J=12.3 Hz, 2 H),2.76 (m, 2 H),1.88-1.80 (m, 2 H),1.57-1.47 (m, 2 H),0.78-0.68 (m, 1 H),0.63-0.54 (m, 1 H),0.42-0.37 (m, 2 H),0.14-0.10 (m, 2 H).

EXAMPLE 9

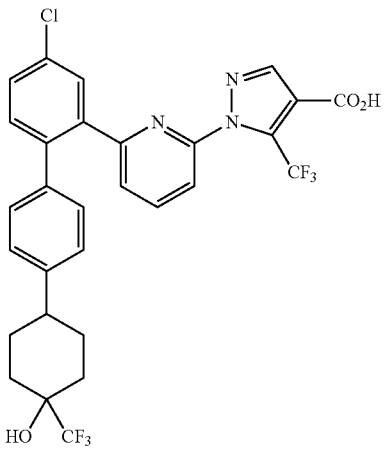 [SMILES: O=C(O)c1cnn(-c2cccc(-c3cc(Cl)ccc3-c3ccc(C4CCC(O)(C(F)(F)F)CC4)cc3)n2)c1C(F)(F)F]

Step A. 4-[4-(4,4,5,5-tetramethyl-1,3,2-dioxaborolan-2-yl)phenyl]cyclohexanone

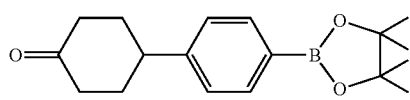

A round bottomed flask was charged with the title compound from Example 4 Step A (1.00 g, 3.12 mmol), bis(pinacolato)diboron (1.19 g, 4.67 mmol), potassium acetate (0.92 g, 9.35 mmol), and 1,1'-bis(di t-butylphosphino)ferrocene palladium dichloride (0.23 g, 0.31 mmol). The flask was purged with nitrogen. Anhydrous 1,4-dioxane (15 mL) was added, and the resulting suspension was degassed via nitrogen sparge. The mixture was then placed in a pre-heated oil bath (80° C.), and was held at this temperature for 1.5 h, whereupon it was allowed to cool to ambient temperature, then was poured into water. The aqueous phase was extracted with ethyl acetate and the organic phase was washed with brine. The organic phase was then dried over anhydrous sodium sulfate and concentrated in vacuo. Purification by chromatography on to silica gel (0 to 100% EtOAc in hexanes) provided the title compound: LCMS m/z 217.6 [M–$C_6H_{11}$]$^-$; $^1$H NMR (500 MHz, $CD_2Cl_2$) δ 7.70 (d, J=8.0 Hz, 2 H), 7.27 (d, J=7.8 Hz, 2 H), 3.09-3.22 (m, 1 H), 2.55-2.40 (m, 4 H), 2.22-2.16 (m, 2 H), 1.99-1.87 (m, 2 H), 1.32 (s, 12 H).

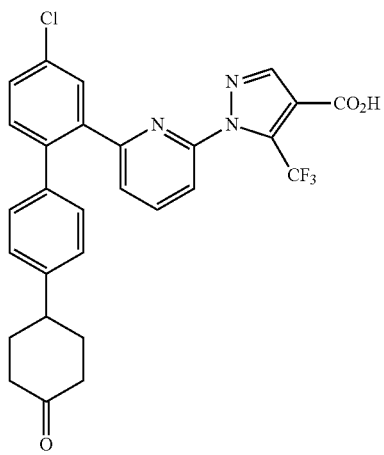 [SMILES: O=C1CCC(c2ccc(-c3ccc(Cl)cc3-c3cccc(-n4ncc(C(=O)O)c4C(F)(F)F)n3)cc2)CC1]

Step B. 1-{6-[4-Chloro-4'-(4-oxocyclohexyl)biphenyl-2-yl]pyridin-2-yl}-5-(trifluoromethyl)-1H-pyrazole-4-carboxylic acid To a flask containing the title compound from the above Step A (56.5 mg, 0.19 mmol) were added the title compound from Example 5 Step D (154 mg, 0.28 mmol) and 1,1'-bis(di t-butylphosphino)ferrocene palladium dichloride (13.8 mg, 0.02 mmol). Acetonitrile (1 mL) and sodium carbonate (0.2 mL of 1.0 M aqueous solution, 0.2 mmol) were added, and the resulting mixture was degassed via nitrogen sparge. The reaction mixture was stirred at 80° C. for 15 h, then was allowed to cool to room temperature and was poured into water. The mixture was extracted with EtOAc, and the organic was concentrated in vacuo. To a solution of the crude material in 1,4-dioxane (0.5 mL) was added sodium hydroxide (0.1 mL of a 1.0 M solution in water, 0.1 mmol), and the resulting mixture was stirred at 60° C. After 15 min, the reaction mixture was rendered acidic by addition of 2N trifluoroacetic acid in DMSO, then was diluted with a dioxane/water 2:1 mixture and passed through a 0.45 μm syringe filter. Purification by reverse phase HPLC (30 to 100% acetonitrile in water, each with 0.1% v/v TFA) provided the title compound: LCMS m/z 539.7 [M+H]$^+$; $^1$H NMR (500 MHz, $CD_2Cl_2$) δ 8.20 (s, 1 H), 7.71 (d, J=2.1 Hz, 1 H), 7.65 (t, J=7.9 Hz, 1 H), 7.51 (d, J=7.8 Hz, 1 H), 7.48 (dd, J=8.3, 2.3 Hz, 1 H), 7.40 (d, J=8.2 Hz, 1 H), 7.18 (d, J=8.2 Hz, 2 H), 7.10 (d, J=8.3 Hz, 2 H), 6.99 (d, J=7.9 Hz, 1 H), 3.06-2.98 (m, 1 H), 2.56-2.40 (m, 4 H), 2.22-2.15 (m, 2 H), 1.96-1.85 (m, 2 H).

Step C. Methyl 1-{6-[4-chloro-4'-(4-oxocyclohexyl)biphenyl-2-yl]pyridin-2-yl}-5-(trifluoromethyl)-1H-pyrazole-4-carboxylate

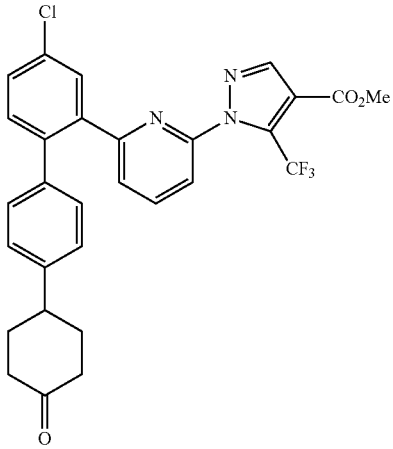 [SMILES: COC(=O)c1cnn(-c2cccc(-c3cc(Cl)ccc3-c3ccc(C4CCC(=O)CC4)cc3)n2)c1C(F)(F)F]

To a vial with a solution of the title compound from the above Step B (14.4 mg, 0.03 mmol) in 4:1 $CH_2Cl_2$:MeOH (0.5 mL) was added dropwise (trimethylsilyl) diazomethane (0.02 mL, 2M in diethyl ether, 0.04 mmol), then the resulting mixture was stirred at ambient temperature. After 20 min, the resulting methyl ester compound was quenched with acetic acid, neutralized with sodium bicarbonate, extracted using DCM, and concentrated. Then the crude mixture was diluted with a 2:1 dioxane/water mixture and passed through a 0.45 μm syringe filter. Purification by reverse phase HPLC (30 to 100% acetonitrile in water, each with 0.1% v/v TFA) provided the title compound: LCMS m/z 553.8 [M+H]$^+$.

Step D. 1-(6-{4'-[4-hydroxy-4-(trifluoromethyl cyclohexyl]-4-methylbiphenyl-2-yl}pyridin-2-yl)-5-(trifluoromethyl)-1H-pyrazole-4-carboxylic acid To a vial with a solution of the title compound from the above Step C (10 mg, 0.02 mmol) in THF (0.4 mL) was added trimethyl(trifluoromethyl)silane (3.34 mg, 0.02 mmol), and a catalytic amount of TBAF (0.004 mL of 1.0 M solution in THF, 0.004 mmol). The resulting mixture was stirred at ambient temperature. After 1 h, the resulting siloxy compound was hydrolyzed with 6M HCl in water and extracted using ether. The combined organic layers were washed with sodium bicarbonate followed by brine, dried over $MgSO_4$ and concentrated. To a solution of the crude material in 1,4-dioxane (0.5 mL) was added sodium hydroxide (0.1 mL, 1.0 M in water, 0.1 mmol), and the resulting mixture was stirred at 60° C. After 15 min, the reaction mixture was rendered acidic by addition of 2N trifluoroacetic acid in DMSO, then was diluted with a 2:1 mixture of dioxane:water and passed through a 0.45 μm syringe filter. Purification by reverse phase HPLC (30 to 100% acetonitrile in water, each with 0.1% v/v TFA) provided the title compound: LCMS m/z 609.7 [M+H]$^+$; $^1$H NMR (500 MHz, $CDCl_3$) δ 8.21 (s, 1 H), 7.74 (d, J=2.0 Hz, 1 H), 7.59 (t, J=7.9 Hz, 1 H), 7.49-7.44 (m, 2 H), 7.37 (d, J=8.2 Hz, 1 H), 7.16 (d, J=8.2 Hz, 2 H), 7.08 (d, J=8.2 Hz, 2 H), 6.93 (d, J=7.6 Hz, 1 H), 2.80-2.73 (m, 1 H), 2.15-2.06 (m, 2 H), 2.01-1.84 (m, 4 H), 1.72-1.63 (m, 2 H).

The compounds in TABLE 1 were prepared using the chemistry described in Examples 1A, 1B and 2~9.

TABLE 1
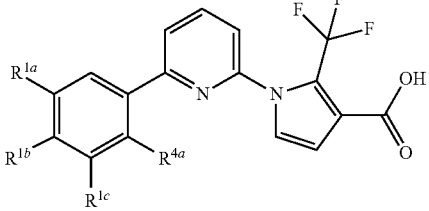
| Example | R¹ᵃ | R¹ᵇ | R¹ᶜ | R⁴ᵃ | MS [M + H]⁺ |
|---|---|---|---|---|---|
| 10 | Me | H | H |  | 479.9 |
| 11 | Me | H | H | 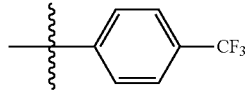 | 492.7 |
| 12 | Me | H | H | 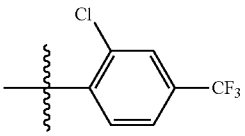 [SMILES: *c1ccc(C(F)(F)F)cc1Cl] | 526.7 |
| 13 | Me | H | H | 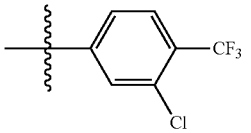 [SMILES: *c1ccc(C(F)(F)F)c(Cl)c1] | 526.7 |
| 14 | Me | H | Me | 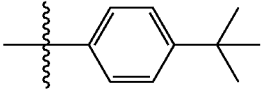 [SMILES: *c1ccc(C(C)(C)C)cc1] | 494.9 |
| 15 | Me | H | H | 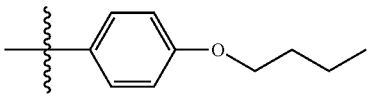 [SMILES: *c1ccc(OCCCC)cc1] | 496.1 |
| 16 | Me | H | H | 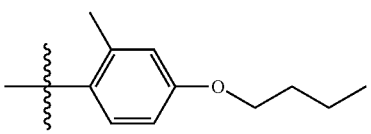 | 510.1 |
| 17 | Me | H | H | 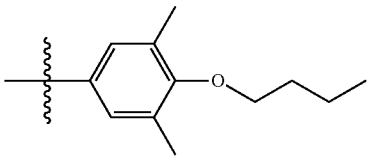 | 524.2 |
| 18 | Me | H | H | 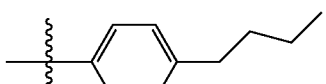 | 480.9 |
| 19 | Cl | H | H | 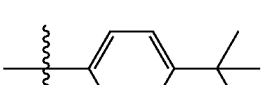 | 500.8 |

TABLE 1-continued
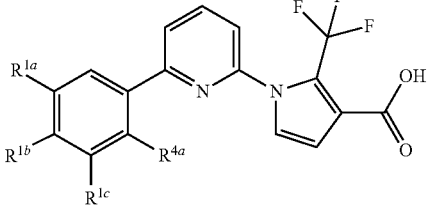
| Example | R¹ᵃ | R¹ᵇ | R¹ᶜ | R⁴ᵃ | MS [M + H]⁺ |
|---|---|---|---|---|---|
| 20 | Me | H | H | 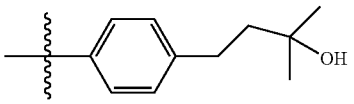 [SMILES: *c1ccc(CCC(C)(C)O)cc1] | 510.0 |
| 21 | Me | H | H | 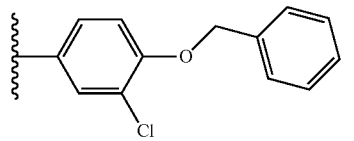 [SMILES: *c1ccc(OCc2ccccc2)c(Cl)c1] | 564.0 |
| 22 | Me | H | H | 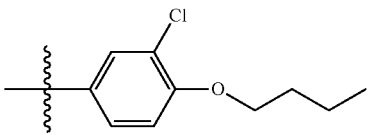 | 530.0 |
| 23 | Me | H | H | 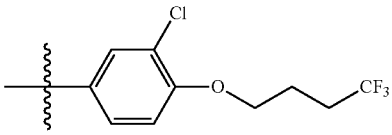 [SMILES: *c1ccc(OCCCC(F)(F)F)c(Cl)c1] | 584.0 |
| 24 | Me | H | Me | 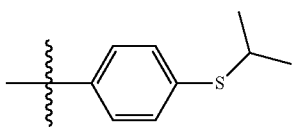 [SMILES: *c1ccc(SC(C)C)cc1] | 498.0 |
| 25 | Me | H | H | 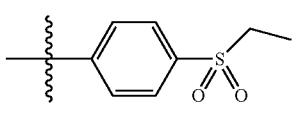 [SMILES: *c1ccc(S(=O)(=O)CC)cc1] | 517.9 |
| 26 | Me | H | H | 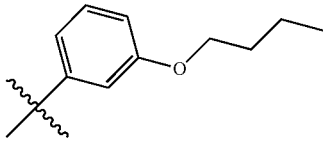 [SMILES: *c1cccc(OCCCC)c1] | 496.0 |
| 27 | Me | H | H | 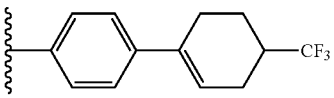 | 572.0 |
| 28 | Me | H | H | 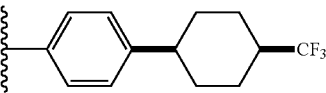 | 574.1 |
| 29 | Me | H | H | 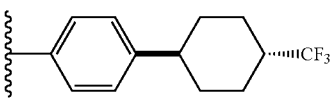 | 574.1 |

TABLE 1-continued
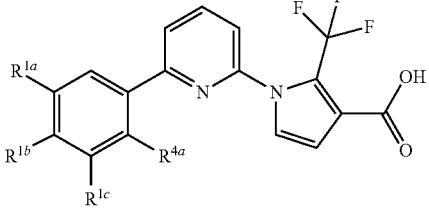
| Example | R1a | R1b | R1c | R4a | MS [M + H]+ |
|---|---|---|---|---|---|
| 30 | Me | H | H | 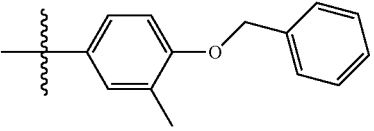 [SMILES: *c1ccc(OCc2ccccc2)c(C)c1] | 544.1 |
| 31 | H | H | H | 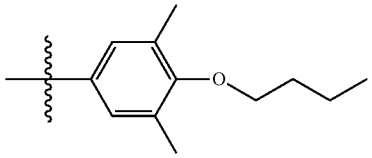 [SMILES: *c1cc(C)c(OCCCC)c(C)c1] | 510.1 |
| 32 | Me | H | H | 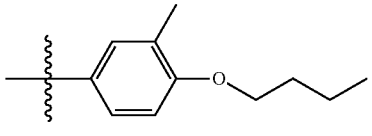 [SMILES: *c1ccc(OCCCC)c(C)c1] | 510.1 |
| 33 | Me | H | H | 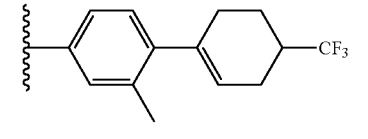 [SMILES: *c1ccc(C2=CCC(C(F)(F)F)CC2)c(C)c1] | 586.1 |
| 34 | Me | H | H | 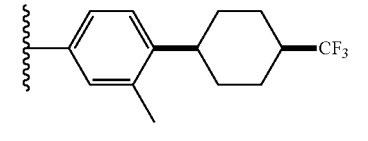 | 588.1 |
| 35 | Me | H | H | 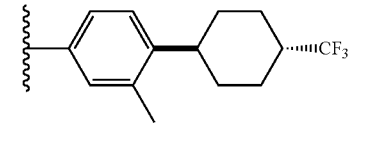 | 588.1 |
| 36 | H | Me | H | 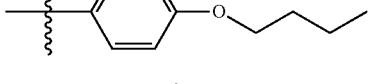 | 495.9 |
| 37 | H | H | Me | 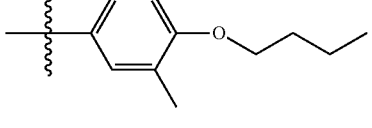 | 523.8 |
| 38 | F | H | H | 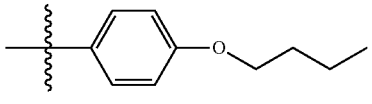 | 499.8 |
| 39 | CF3 | H | H | 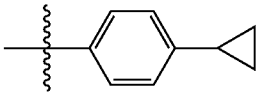 [SMILES: *c1ccc(C2CC2)cc1] | 517.9 |

TABLE 1-continued

| Example | R¹ᵃ | R¹ᵇ | R¹ᶜ | R⁴ᵃ | MS [M + H]⁺ |
|---------|-----|-----|-----|-----|-------------|
| 40 | CF₃ | H | H | 4-(benzyloxy)-3-methylphenyl | 597.8 |
| 41 | Me | H | H | 4-(4-oxocyclohexyl)phenyl | 519.9 |
| 42 | Cl | H | H | 4-(4-oxocyclohexyl)phenyl | 539.7 |
| 43 | CF₃ | H | H | 4-(4-oxocyclohexyl)phenyl | 573.8 |
| 44 | Cl | H | H | 4-(4,4-difluorocyclohexyl)phenyl | 561.8 |
| 45 | CF₃ | H | H | 4-(4,4-difluorocyclohexyl)phenyl | 595.8 |
| 46 | Cl | H | H | 3-methyl-4-(2-(pyrrolidin-1-yl)ethoxy)phenyl | 571.0 |
| 47 | Cl | H | H | 4-((2,2-difluorocyclopropyl)methoxy)phenyl | 549.9 |
| 48 | Cl | H | H | 4-(benzyloxy)phenyl | 549.9 |
| 49 | Cl | H | H | 4-((5-(trifluoromethyl)furan-2-yl)methoxy)phenyl | 607.9 |
| 50 | Cl | H | H | 4-(pyridin-4-ylmethoxy)phenyl | 550.9 |

TABLE 1-continued

| Example | R¹ᵃ | R¹ᵇ | R¹ᶜ | R⁴ᵃ | MS [M + H]⁺ |
|---|---|---|---|---|---|
| 51 | Cl | H | H | 4-(4-trifluoromethoxybenzyloxy)phenyl | 661.9 |
| 52 | Cl | H | H | 4-trifluoromethoxyphenyl | 527.8 |
| 53 | Cl | H | H | 3-fluoro-4-trifluoromethoxyphenyl | 545.8 |
| 54 | Cl | H | H | 4-difluoromethoxyphenyl | 509.8 |
| 55 | Cl | H | H | 4-benzyloxy-3-methylphenyl | 563.8 |
| 56 | Cl | H | H | 4-(4-methoxycyclohexyl)phenyl | 555.8 |
| 57 | Me | H | H | 4-(4-cyclopropylpiperidin-1-yl)phenyl | 547.0 |
| 58 | Cl | H | H | 4-(4-trifluoromethylpiperidin-1-yl)phenyl | 594.7 |
| 59 | Me | H | H | 4-(4-trifluoromethylpiperidin-1-yl)phenyl | 574.8 |

EXAMPLE 60

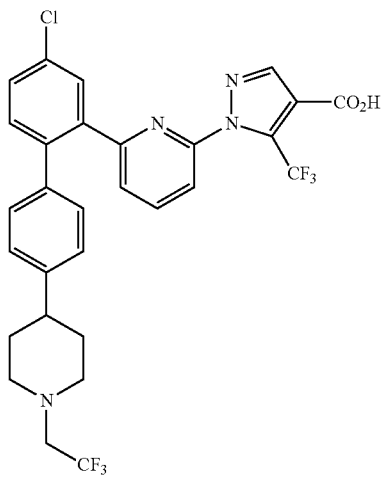 [SMILES: O=C(O)c1cnn(-c2cccc(-c3cc(Cl)ccc3-c3ccc(C4CCN(CC(F)(F)F)CC4)cc3)n2)c1C(F)(F)F]

Step A. 4-(4-bromophenyl)-1-(2,2,2-trifluoroethyl)piperidine

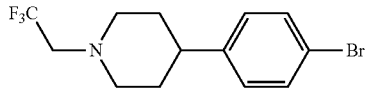

To a mixture of 4-(4-bromophenyl)piperidine hydrochloride (5 g, 18.1 mmol) and 2,2,2-trifluoroethyl trifluoromethanesulfonate (4.62 g, 19.9 mmol) in ACN (250 mL) was added N,N-diisopropylethyl amine (11 mL, 63.2 mmol). The reaction mixture was heated at 45° C. for 50 min. 2,2,2-trifluoroethyl trifluoromethanesulfonate (0.46 g, 2.0 mmol) was added and heating continued for 1 h. Another 0.46 g of 2,2,2-trifluoroethyl trifluoromethanesulfonate (2.0 mmol) was added and heating continued for 1 h. The reaction mixture was concentrated, diluted with brine and extracted twice with a mixture of hexanes-EtOAc-DCM. The organic layers were combined, concentrated, diluted with toluene and concentrated again. Purification by flash chromatography on silica gel (0 to 100% EtOAc in hexanes) provided the title compound: LCMS m/z 322.2 [M+H]$^+$. $^1$H NMR (400 MHz, CDCl$_3$) δ 7.40 (d, J=8.4 Hz, 2 H),7.08 (d, J=8.4 Hz, 2 H),3.06 (m, 2 H),3.00 (q, J=9.7 Hz, 2 H),2.45 (m, 3 H).1.77 (m, 4H).

Step B. 4-[4-(4,4,5,5-tetramethyl-1,3,2-dioxaborolan-2-yl)phenyl]-1-(2,2,2-trifluoroethyl)piperidine

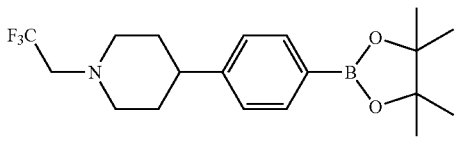 [SMILES: CC1(C)OB(c2ccc(C3CCN(CC(F)(F)F)CC3)cc2)OC1(C)C]

To a flask containing the title compound from the above Step A (5.44 g, 16.9 mmol) in 1,4-dioxane (65 mL) was added 1,1 bis(di-tert-butylphosphino)ferrocene palladium dichloride (330 mg, 0.51 mmol), bis(pinacolato)diboron (6.50 g, 25.4 mmol), and KOAc (4.20 g, 42.9 mmol). The reaction mixture was stirred under nitrogen at 95° C. for 1.5 h. The reaction mixture was then cooled to ambient temperature, diluted with hexanes, and passed through a pad of silica gel, eluted by 20% EtOAc in hexanes. Purification by flash chromatography on silica gel (20 to 50% DCM in hexanes, then 5 to 15% EtOAc in hexanes) provided the title compound: LCMS m/z 370.1 [M+H]$^+$. $^1$H NMR (400 MHz, CDCl$_3$) δ (ppm) 7.74 (d, J=8.0 Hz, 2 H),7.23 (d, J=8.0 Hz, 2 H),3.07 (m, 2 H),3.01 (q, J=9.7 Hz, 2 H),2.47 (m, 3 H).1.81 (m, 4 H),1.32 (s, 12 H).

Step C. 1-(6-{4-chloro-4'-[1-(2,2,2-trifluoroethyl)piperidin-4-yl]biphenyl-2-yl}pyridin-2-yl)-5-(trifluoromethyl)-1-pyrazole-4-carboxylic acid To a mixture of the title compound from Example 5 Step D (100 mg, 0.184 mmol) and the title compound from the above Step B (68 mg, 0.184 mmol) in ACN (1 mL) were added 1,1 bis(di-tert-butylphosphino)ferrocene palladium dichloride (10 mg, 0.015 mmol) and sodium carbonate (0.3 mL of 1M aq. solution, 0.3 mmol). The reaction mixture was placed in an oil bath at 80° C. for 30 min., then heated at 85° C. for 30 min, and then heated at 90° C. for 30 min. The reaction mixture was allowed to cool to ambient temperature, diluted with brine and extracted twice with hexanes-EtOAc. The organic layers were combined, concentrated and purified by flash chromatography on silica gel (10 to 20% EtOAc in hexanes). Product fractions were concentrated, diluted with a mixture of 1,4-dioxane (0.4 mL), methanol (0.4 mL), and 3N LiOH (0.4 mL) then the mixture was placed in an oil bath at 50° C. After 15 min, the reaction mixture was rendered acidic by addition of trifluoroacetic acid solution in ACN-water and passed through a 0.45 μm syringe filter. Purification by reverse phase HPLC (30 to 100% acetonitrile in water, each with 0.1% v/v TFA) provided the title compound: LCMS m/z 609.1 [M+H]$^+$; $^1$H NMR (500 MHz, CD$_3$OD) δ 8.18 (s, 1 H),7.76 (t, J=7.9 Hz, 1 H),7.67 (d, J=2.3 Hz, 1 H),7.58 (d, J=7.9 Hz, 1 H),7.53 (dd, J=8.2, 2.3 Hz, 1 H),7.43 (d, J=8.2 Hz, 1 H),7.20 (d, J=8.2 Hz, 2 H), 7.12 (d, J=8.2 Hz, 2 H),7.08 (d, J=7.9 Hz, 1 H),3.81 (q, J=9.2 Hz, 2 H),3.50 (d, J=12.0 Hz, 2 H),3.03 (m, 2 H),2.76 (m, 1 H),1.96 (m, 4 H).

EXAMPLE 61

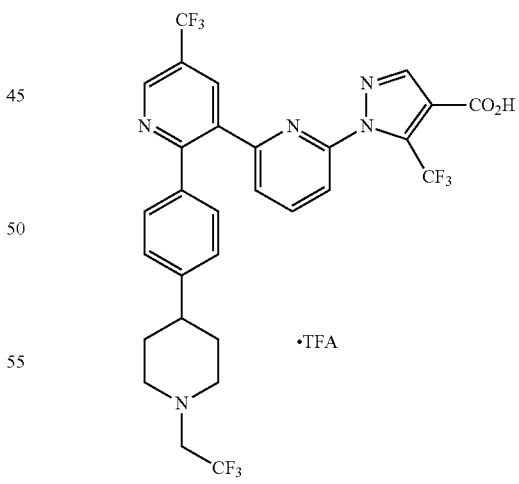

Step A. Ethyl 1-[2'-fluoro-5'-(trifluoromethyl)-2,3'-bipyridin-6-yl]-5-(trifluoromethyl)-1H-pyrazole-4-carboxylate A mixture of 3-chloro-2-fluoro-5-(trifluoromethyl)pyridine (1.30 g, 6.52 mmol), bis(pinacolato)diboron (2.00 g, 7.87 mmol), KOAc (1.52 g, 15.5 mmol), bis(tricyclohexylphosphine)palladium(0) (260 mg, 0.40 mmol) and 1,4-dioxane (10 mL) was heated at 100° C. for 50 min and was allowed to cool. Water was added and the reaction mixture was extracted with EtOAc. The organic phase was dried over sodium sulfate, passed through a silica pad and concentrated. Hexanes was added and the reaction mixture was filtered and concentrated to give the crude 2-fluoro-3-(4,4,5,5-tetramethyl-1,3,2-dioxaborolan-2-yl)-5-(trifluoromethyl)pyridine. 2.09 g such material was mixed with the title compound from Example 1 Step A (1.00 g, 3.1 mmol), trans-dichlorobis(triphenylphosphine) palladium (II) (154 mg, 0.22 mmol), CsF (1.43 g, 9.40 mmol), Na₂CO₃ (3.9 mL of 2.0 M aqueous solution, 7.8 mmol) and acetonitrile (15 mL). The resulting mixture was stirred at 100° C. under nitrogen for 45 min and was allowed to cool. Water was added and the reaction mixture was extracted by hexane and EtOAc, followed by silica gel flash chromatography (hexanes-EtOAc, 9:1 to 8.5:1.5 v/v) gave the title compound: LCMS m/z 449.1 [M+H]$^+$; $^1$H NMR (400 MHz, CDCl$_3$) δ 8.96 (dd, J=8.7, 2.5 Hz, 1 H), 8.56 (s, 1 H), 8.16-8.12 (m, 2 H), 8.08 (t, J=7.9 Hz, 1 H), 7.79 (dd, J=7.8, 0.8 Hz, 1 H), 4.39 (q, J=7.2 Hz, 2 H), 1.40 (t, J=7.2 Hz, 3 H).

Step B. Methyl 1-[2'-methoxy-5'-(trifluoromethyl)-2,3'-bipyridin-6-yl]-5-(trifluoromethyl)-1H-pyrazole-4-carboxylate AND ethyl 1-[2'-methoxy-5'-(trifluoromethyl)-2,3'-bipyridin-6-yl]-5-(trifluoromethyl)-1H-pyrazole-4-carboxylate (Mixture)

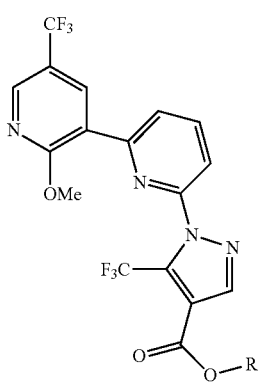

R = mixture of ethyl and methyl

To a cooled (0° C.) solution of the title compound from the above Step A dissolved in THF (10 mL), was added dropwise a solution of 0.5 M NaOMe (1.75 mL, 0.875 mmol) in THF. The reaction mixture was aged at 0° C. for 30 min then warmed to 4° C. and left at that temperature overnight. Another portion of 0.5 M NaOMe (0.3 mL, 0.15 mmol) solution was added at 0° C. After aging for 3 h, 2 N aqueous HCl was added, and the crude reaction mixture was extracted by a hexanes-EtOAc mixture, concentrated in vacuo and used directly in the following Step B. LCMS showed the formation of a mixture of ethyl and methyl esters: m/z 447.0, 461.0 [M+H]$^+$.

Step C. methyl 1-[2'-hydroxy-5'-(trifluoromethyl)-2,3'-bipyridin-6-yl]-5-(trifluoromethyl-1H-pyrazole-4-carboxylate AND ethyl 1-[2'-hydroxy-5'-(trifluoromethyl)-2,3'-bipyridin-6-yl]-5-(trifluoromethyl)-1H-pyrazole-4-carboxylate (Mixture)

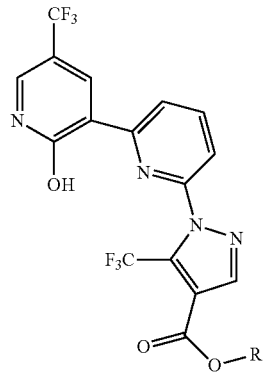

R = mixture of ethyl and methyl

The crude product obtained from the above Step B was dissolved in chloroform (8 mL) and TMSI (1.5 mL, 10.5 mmol) was added. The reaction mixture was placed in an oil bath brought to 60° C. for 2 h. After the reaction mixture was cooled to ambient temperature, it was concentrated, then diluted with toluene and concentrated. The residue was taken up in MeOH and reconcentrated. Lastly the crude material was diluted with toluene, concentrated, and then dried under high vacuum overnight. LCMS showed products as a mixture of ethyl and methyl esters: m/z 433.0, 447.0 [M+H]$^+$.

Step D. methyl 5-(trifluoromethyl)-1-(5'-(trifluoromethyl)-2'-{[(trifluoromethyl)sulfonyl]oxy}-2,3'-bipyridin-6-yl)-1H-pyrazole-4-carboxylate AND ethyl 5-(trifluoromethyl)-1-(5'-(trifluoromethyl)-2'-{[(trifluoromethyl)sulfonyl]oxy}-2,3'-bipyridin-6-yl-1H-pyrazole-4-carboxylate (Mixture)

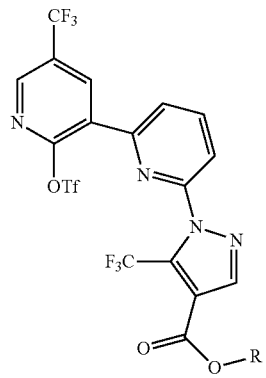

R = mixture of ethyl and methyl

To a cooled (−78° C.) solution of the crude material from the above Step C in DCM (10 mL), was added pyridine (0.222 mL, 2.75 mmol), followed by triflic anhydride (0.278 mL, 1.65 mmol). The reaction was allowed to warm to ambient temperature in about 10 min. The reaction was then quenched with 2 N aqueous HCl, and extracted with a hexanes-EtOAc mixture twice. The combined organic layers were concentrated and purified by flash chromatography on silica gel (1:0, 7:3 v/v hexanes:DCM) providing the triflate as a mixture of ethyl and methyl esters: LCMS m/z 565.1, 579.2 [M+H].

Step E. 1-[2'-{4-[1-(2,2,2-trifluoroethyl)piperidin-4-yl]phenyl}-5'-(trifluoromethyl)-2,3'-bipyridin-6-yl]-5-(trifluoromethyl)-1H-pyrazole-4-carboxylic acid To the mixture of the title compounds obtained from the above Step D (150 mg) in ACN (1.5 mL) was added the title compound from Example 60 Step B (125 mg, 0.34 mmol), 1,1 bis(di-tert-butylphosphino)ferrocene palladium dichloride (18 mg, 0.028 mmol), sodium carbonate (0.414 mL of a 1 M aqueous solution, 0.414 mmol) and the reaction mixture was heated at 70° C. overnight. Brine was added and the crude mixture was extracted twice with hexanes-EtOAc-DCM. The organic layers were combined and concentrated, then redissolved in toluene and reconcentrated. Purification by flash chromatography on silica gel (5 to 20% EtOAc in hexanes) provided a mixture of methyl and ethyl esters of the desired product: LCMS m/z 658.1, 672.1 [M+H]$^+$. The mixture was dissolved in 1,4-dioxane (1 mL). MeOH (0.3 mL) and 3 N LiOH (0.16 mL) were added and the reaction mixture was heated at 40° C. for 30 min, followed by a subsequent addition of 3 N LiOH (0.080 mL) and further heating for 15 min. The reaction mixture was allowed to cool to ambient temperature, followed by quenching with a mixture of TFA (0.1 mL), MeCN (0.167 mL) and water (0.333 mL). Purification by reverse phase HPLC using an YMC C-18 column eluted by 0.1% TFA-modified acetonitrile in water (30% to 100%) gave the title compound as a TFA salt after lyophilization: LCMS m/z 643.9 [M+H]$^+$. $^1$H NMR (600 MHz, CD$_3$CN) δ 9.02 (d, J=1.2 Hz, 1 H), 8.29 (d, J=2.0 Hz, 1 H), 8.14 (s, 1 H), 7.86 (t, J=7.8 Hz, 1 H), 7.65 (d, J=7.8 Hz, 1 H), 7.34 (d, J=8.1 Hz, 2 H), 7.28 (d, J=7.8 Hz, 1 H), 7.20 (d, J=8.1 Hz, 2 H), 3.80 (q, J=9.3 Hz, 2 H), 3.57 (d, J=12.2 Hz, 2 H), 3.11 (m, 2 H), 2.83 (m, 1 H), 2.01 (m, 4 H).

EXAMPLE 62A and 62B

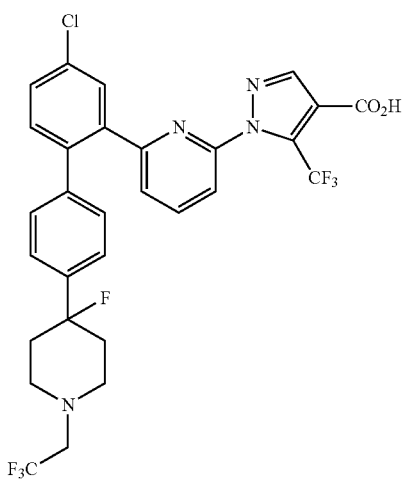

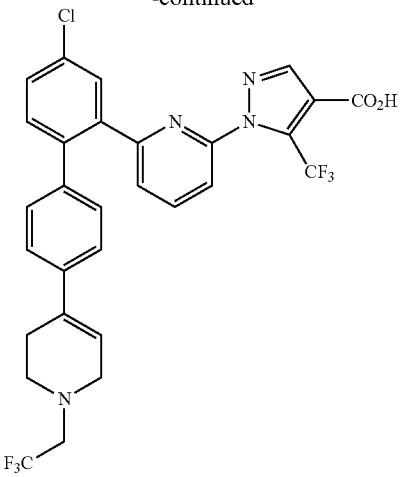

Step A. tert-butyl 4-fluoro-4-[4-(4,4,5,5-tetramethyl-1,3,2-dioxaborolan-2-yl)phenyl]piperidine-1-carboxylate

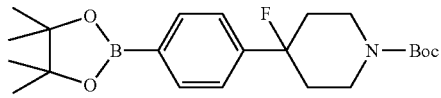

A flask was charged with 4-(4-bromophenyl)piperidin-4-ol (1 g, 3.90 mmol), di-tert-butyl dicarbonate (0.852 g, 3.90 mmol) and 5 mL DCM. Bubbling occurred and most of solid was dissolved. To the reaction mixture was added 0.15 g di-tert-butyl dicarbonate (0.7 mmol) and 0.1 ml N,N-diisopropyl ethyl amine (0.58 mmol). After 10 min of stirring, the reaction vessel was cooled in an ice-water bath. DAST (0.567 mL, 4.3 mmol) was added, and the resulting reaction mixture was stirred at 0° C. for 1 h, then at ambient temperature for 30 min. After another portion of DAST (0.15 mL, 1.1 mmol) was added and the reaction mixture was further stirred at ambient temperature for 1 h, saturated aq. NaHCO$_3$ was slowly added. Hexanes was added and reaction mixture was allowed to separate overnight. The organic layer was concentrated and purified by flash silica gel chromatography eluting with hexanes:dicholoromethane (1:0 then 7:3 then 6:4 v/v) and hexanes-EtOAc (9:1 v/v) to give a mixture of the desired product and the alkene elimination product. LCMS m/z 283.8 [M−HF−$^t$Bu+2H]$^+$. This material, 10 mL dioxane, 1,1-bis(di-tert-butylphosphino)ferrocene palladium dichloride (60 mg, 0.09 mmol), bis(pinacolato)diboron (806 mg. 3.15 mmol), and KOAc (600 mg, 6.1 mmol) were mixed and stirred under nitrogen at 95° C. for 2 hr. The reaction mixture was cooled, diluted with 60 ml hexanes, and passed through a pad of silica gel, eluting with hexanes:EtOAc (4:1 v/v) 100 mL. Flash silica gel chromatography eluting with hexanes-dicholoromethane then hexanes-dicholoromethane-EtOAc gave the title compound. LCMS m/z 405.9 [M+H]$^+$. $^1$H NMR (500 MHz, CD$_2$Cl$_2$) 5 (ppm) 7.80 (d, J=7.8 Hz, 2 H), 7.41 (d, J=7.8 Hz, 2 H), 4.14 (br, 2 H), 3.17 (br, 2 H), 2.06-1.97 (m, 4 H). 1.50 (s, 9 H), 1.36 (s, 12 H).

Step B. Ethyl 1-{6-[4-chloro-4'-(4-fluoropiperidin-4-yl)biphenyl-2-yl]pyridin-2-yl}-5-(trifluoromethyl)-1H-pyrazole-4-carboxylate AND ethyl 1-{6-[4-chloro-4'-(4-fluoropiperidin-4-yl)biphenyl-2-yl]pyridin-2-yl}-5-2-yl}-5-(trifluoromethyl)-1H-pyrazole-4-carboxylate (Mixture)

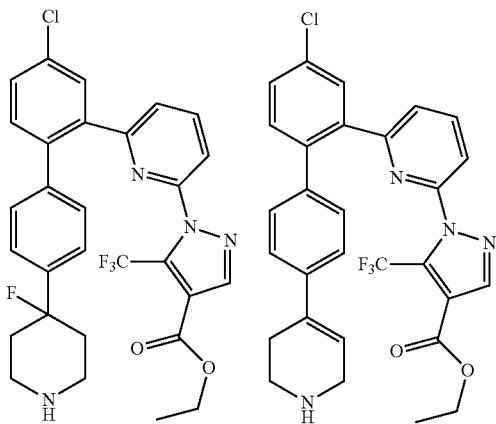

A mixture of the title compound from Example 5 Step D (168 mg, 0.31 mmol), the title compound from the above Step A (126 mg, 0.31 mmol), 1,1 bis(di-tert-butylphosphino)ferrocene palladium dichloride (21 mg, 0.032 mmol) and sodium carbonate (0.465 mL of 1M aq. solution, 0.465 mmol) were dissolved in ACN (2 mL) and then heated at 90° C. for 1 h. After the reaction mixture was cooled to ambient temperature, brine was added and the crude mixture was extracted by hexanes-EtOAc-DCM twice. The organic layers were combined and concentrated.

Purification by flash chromatography on silica gel (7 to 25% EtOAc in hexanes) provided an impure mixture containing the Boc-protected amines. LCMS m/z 552.9 [M-Boc+2H]$^+$. This material was dissolved in DCM (4 mL) and was treated with TFA (2 mL) for 15 min. Toluene was added and solvent was removed. DCM was added to dissolve the material and 2N HCl in ether was added. Solvent was removed and the material was dried under high vacuum overnight to give a crude mixture containing the desired free amine as the HCl salt. LCMS m/z 552.9 [M+H]$^+$.

Step C. 1-(6-{4-chloro-4'-[4-fluoro-1-(2,2,2-trifluoroethyl)piperidin-4-yl]biphenyl-2-yl}pyridin-2-yl)-5-(trifluoromethyl)-1H-pyrazole-4-carboxylic acid (Example 62A) AND 1-(6-{4-chloro-4'-[1-(2,2,2-trifluoroethyl)-1,2,3,6-tetrahydropyridin-4-yl]biphenyl-2-yl}pyridin-2-yl)-5-(trifluoromethyl)-1H-pyrazole-4-carboxylic acid (Example 62B)

A mixture of 20 mg crude product from the above Step B, 2,2,2-trifluoroethyl trifluoromethanesulfonate (17 ng, 0.07 mmol), Cs$_2$CO$_3$ (28 mg, 0.09 mmol) and DMF (0.3 mL) was heated at 60° C. for 40 min. After further treatment with 0.1 mL each of 3 N NaOH, MeOH and 1,4-dioxane for 15 min at 50° C., reverse phase HPLC using an YMC C-18 column eluted by 0.1% TFA-modified acetonitrile in water (45% to 100%) gave the title compounds. 1-(6-{4-chloro-4'-[4-fluoro-1-(2,2,2-trifluoroethyl)piperidin-4-yl]biphenyl-2-yl}pyridin-2-yl)-5-(trifluoromethyl)-1H-pyrazole-4-carboxylic acid: LCMS m/z 626.9 [M+H]$^+$; $^1$H NMR (500 MHz, acetone-d$_6$) δ (ppm) 8.25 (s, 1 H), 7.88 (t, J=7.9 Hz, 1 H), 7.78 (d, J=2.1 Hz, 1 H), 7.72 (d, J=7.8 Hz, 1 H), 7.60 (dd, J=8.2, 2.1 Hz, 1 H), 7.54 (d, J=8.5 Hz, 1 H), 7.45 (d, J=8.2 Hz, 2 H), 7.20 (d, J=8.2 Hz, 2 H), 7.13 (d, J=7.8 Hz, 1 H), 6.23 (s, 1 H), 3.52 (m, 2 H), 3.40 (q, J=9.8 Hz, 2 H), 3.07 (t, J=5.6 Hz, 2 H), 2.64 (m, 2 H). 1-(6-{4-chloro-4'-[1-(2,2,2-trifluoroethyl)-1,2,3,6-tetrahydropyridin-4-yl]biphenyl-2-yl}pyridin-2-yl)-5-(trifluoromethyl)-1H-pyrazole-4-carboxylic acid: LCMS m/z 607.6 [M+H]$^+$; $^1$H NMR (500 MHz, acetone-d$_6$) δ (ppm) 8.24 (s, 1 H), 7.90 (t, J=7.9 Hz, 1 H), 7.78 (d, J=2.1 Hz, 1 H), 7.72 (d, J=8.0 Hz, 1 H), 7.62 (dd, J=8.2, 2.1 Hz, 1 H), 7.54 (d, J=8.2 Hz, 1 H), 7.43 (d, J=8.2 Hz, 2 H), 7.26 (d, J=8.2 Hz, 2 H), 7.15 (d, J=7.8 Hz, 1 H), 3.51 (q, J=9.8 Hz, 2 H), 3.19 (m, 2 H), 3.05 (t, J=11.8 Hz, 2 H), 2.34 (m, 2 H), 2.04 (m, 2 H).

EXAMPLE 63

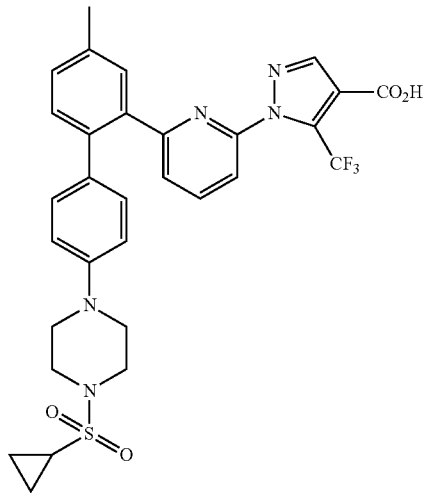 [SMILES: Cc1ccc(-c2ccc(N3CCN(S(=O)(=O)C4CC4)CC3)cc2)c(-c2cccc(-n3ncc(C(=O)O)c3C(F)(F)F)n2)c1]

Step A tert-butyl 4-(4-bromophenyl)piperazine-1-carboxylate

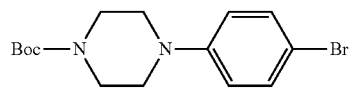 [SMILES: CC(C)(C)OC(=O)N1CCN(c2ccc(Br)cc2)CC1]

To a suspension of 1-(4-bromophenyl)piperazine (5.02 g, 20.8 mmol) in DCM was added di-tert-butyl dicarbonate (6.82 g, 31.2 mmol) and DIEA (7.26 mL, 41.7 mmol). The resulting mixture was degassed via nitrogen sparge and stirred for 30 min. The reaction mixture was then quenched with saturated ammonium chloride solution (aq), extracted with ethyl acetate and concentrated in vacuo. Purification by chromatography on silica gel (0 to 30% EtOAc in hexanes, then 30 to 100% EtOAc in hexanes) provided the title compound: LCMS m/z 286.7 [M-t-Bu+2H]$^+$; $^1$H NMR (500 MHz, acetone-d$_6$) δ 7.35 (d, J=9.1 Hz, 2 H), 6.92 (d, J=9.0 Hz, 2 H), 3.52 (t, J=5.0 Hz, 4 H), 3.13 (t, J=5.2 Hz, 4 H), 1.44 (s, 9 H).

Step B. tert-butyl 4-[4-(4,4,5,5-tetramethyl-1,3,2-dioxaborolan-2-yl)phenyl]piperazine-1-carboxylate

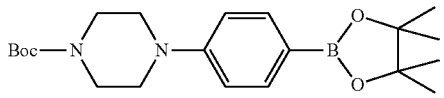 [SMILES: CC(C)(C)OC(=O)N1CCN(c2ccc(B3OC(C)(C)C(C)(C)O3)cc2)CC1]

A round bottomed flask was charged with the title compound from the Step A above (3.62 g, 10.6 mmol), bis(pinacolato)diboron (4.0 g, 15.9 mmol), potassium acetate (3.12 g, 31.8 mmol), and 1,1'-bis(di t-butylphosphino)ferrocene palladium dichloride (0.39 g, 0.53 mmol). The flask was purged with nitrogen. Anhydrous 1,4 dioxane (50 mL) was added, and the resulting suspension was degassed via nitrogen sparge. The mixture was then placed in a pre-heated oil bath (90° C.), and was held at this temperature for 1 h, whereupon it was allowed to cool to ambient temperature, then was poured into water. The aqueous phase was extracted with ethyl acetate and the organic phase was washed with brine. The organic phase was then dried over anhydrous sodium sulfate and concentrated in vacuo. Purification by chromatography on silica gel (0 to 100% EtOAc in hexanes) provided the title compound: LCMS m/z 250.9 [M-t-Bu—$C_6H_{10}$+2H]$^+$; $^1$H NMR (500 MHz, acetone-$d_6$) δ 7.61 (d, J=8.7 Hz, 2 H),6.94 (d, J=8.7 Hz, 2 H),3.53 (m, 4 H),3.22 (m, 4 H),1.45 (s, 9 H),1.29 (s, 12 H).

Step C. ethyl 1-{6-[4-methyl-4'-(piperazin-1-yl)biphenyl-2-yl]pyridin-2-yl}-5-(trifluoromethyl)-1H-pyrazole-4-carboxylate

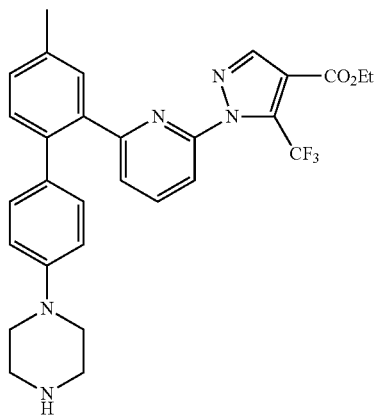 [SMILES: CCOC(=O)c1cnn(-c2cccc(-c3cc(C)ccc3-c3ccc(N4CCNCC4)cc3)n2)c1C(F)(F)F]

To a flask containing the title compound from the Step B above (121 mg, 0.31 mmol) was added the title compound from Examples 1A and 1B Step D (245 mg, 0.47 mmol) and 1,1'-bis(di t-butylphosphino)ferrocene palladium dichloride (23.0 mg, 0.03 mmol). Acetonitrile (4 mL) and sodium carbonate (0.62 mL of 1.0 M aqueous solution, 0.62 mmol) were added, and the resulting mixture was degassed via nitrogen sparge. The reaction mixture was stirred at 85° C. for 1 h, then was allowed to cool to room temperature and was poured into water. The mixture was extracted with EtOAc, and the organic phase was collected and concentrated in vacuo. Purification by chromatography on silica gel (0 to 25% EtOAc/hex, then 30 to 100% EtOAc/hex) provided the N-Boc protected piperazine compound. Deprotection was carried out by dissolving the Boc protected intermediate in DCM (5 mL), followed by the addition of 1 mL of trifluoroacetic acid and stirring for 20 min. The reaction mixture was then concentrated and the remaining trifluoroacetic acid was azeotroped three times with toluene. The resulting free piperazine compound was used without further purification: LCMS m/z 535.8 [M+H]$^+$; $^1$H NMR (500 MHz, CDCl$_3$) δ 8.14 (s, 1 H),7.60 (t, J=7.8 Hz, 1 H),7.55 (s, 1 H),7.43 (d, J=7.7, 1 H),7.30 (s, 2 H),7.10 (d, J=8.6 Hz, 2 H),6.95 (d, J=7.7 Hz, 1 H),6.82 (d, J=8.7 Hz, 2H), 4.39 (q, J=7.1 Hz, 2 H),3.44 (d, J=5.7 Hz, 4 H),3.38 (d, J=4.6 Hz, 4 H),2.44 (s, 3 H),1.40 (t, J=—7.1 Hz, 3 H).

Step D. 1-(6-{4'-[4-(cyclopropylsulfonyl)piperazin-1-yl]-4-methylbiphenyl-2-yl}pyridin-2-yl)-5-(trifluoromethyl)-1H-pyrazole-4-carboxylic acid To a solution of the title compound from the above Step C (29.5 mg, 0.06 mmol) and cyclopropanesulfonyl chloride (0.008 mL, 0.08 mmol) in DMF (1 mL) was added cesium carbonate (35.9 mg, 0.11 mmol), and the resulting mixture was stirred at 60° C. for 1 h. The mixture was quenched by addition of 2N HCl. The aqueous phase was extracted with ethyl acetate, and the organic phase was dried over sodium sulfate, and concentrated in vacuo. To a solution of the crude material in 1,4-dioxane (0.5 mL) was added sodium hydroxide (0.1 ml, 1.0 M in water, 0.1 mmol), and the resulting mixture was stirred at 60° C. After 15 min, the reaction mixture was rendered acidic by addition of 2N trifluoroacetic acid in DMSO, then was diluted with a 2:1 mixture of dioxane:water and passed through a 0.45 m syringe filter. Purification by reverse phase HPLC (30 to 100% acetonitrile in water, each with 0.1% v/v TFA) provided the title compound: LCMS m/z 611.8 [M+H]$^+$; $^1$H NMR (500 MHz, acetone-$d_6$) δ 8.22 (s, 1 H), 7.81 (t, J=7.8 Hz, 1 H),7.62 (d, J=7.7 Hz, 1 H),7.51 (s, 1 H),7.32 (s, 2 H),7.07-7.03 (m, 3 H), 6.92 (d, J=8.7 Hz, 2 H),3.42 (m, 4 H),3.28 (m, 4 H),2.53 (m, 1 H),2.41 (s, 3 H),1.04 (s, 2 H), 1.02 (s, 2 H).

EXAMPLE 64

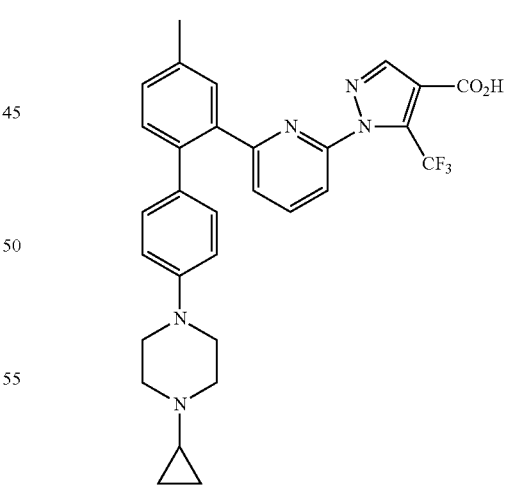

1-{6-[4'-(4-cyclopropylpiperazin-1-yl)-4-methylbiphenyl-2-yl]pyridin-2-yl}-5-(trifluoromethyl)-1H-pyrazole-4-carboxylic acid To a solution of the title compound from Example 63 Step C (32.2 mg, 0.06 mmol) and [(1-ethoxycyclopropyl)oxy](trimethyl)silane (31.4 mg, 0.18 mmol) in THF:H$_2$O:AcOH (10:1:0.2 mL) was added sodium cyanoborohydride (7.31 mg, 0.12 mmol), and the resulting mixture was stirred for at 70° C. for 1 h. The mixture was quenched by addition of 1M sodium carbonate (aq). The aqueous phase was extracted with ethyl acetate, and the organic phase was dried over sodium sulfate, and concentrated in vacuo. To a solution of the crude material in 1,4-dioxane (0.5 mL) was added sodium hydroxide (0.1 mL, 1.0 M in water, 0.1 mmol), and the resulting mixture was stirred at 60° C. After 15 min, the reaction mixture was rendered acidic by addition of 2N trifluoroacetic acid in DMSO, then was diluted with a 2:1 mixture of dioxane/water and passed through a 0.45 μm syringe filter. Purification by reverse phase HPLC (30 to 100% acetonitrile in water, each with 0.1% v/v TFA) provided the title compound: LCMS m/z 547.8 [M+H]$^+$; $^1$H NMR (500 MHz, acetone-d$_6$) δ 8.22 (s, 1 H),7.80 (t, J=7.9 Hz, 1 H),7.61 (d, J=7.9 Hz, 1 H),7.51 (s, 1 H),7.32 (d, J=1.0 Hz, 2 H),7.07-7.04 (m, 3 H),6.94 (d, J=8.9 Hz, 2 H), 3.54 (m, 8 H),2.87 (m, 1 H),2.41 (s, 3 H),1.23 (m, 2 H),0.86 (m, 2 H).

EXAMPLE 65

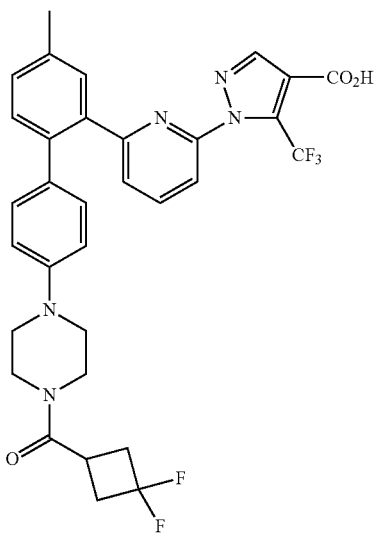 [SMILES: Cc1ccc(-c2ccc(N3CCN(C(=O)C4CC(F)(F)C4)CC3)cc2)c(-c2cccc(-n3ncc(C(=O)O)c3C(F)(F)F)n2)c1]

1-[6-(4'-{4-[(3,3-difluorocyclobutyl)carbonyl]piperazin-1-yl}-4-methylbiphenyl-2-yl)pyridin-2-yl]-5-(trifluoromethyl)-1H-pyrazole-4-carboxylic acid To a solution of the title compound from Example 63 Step C (21.5 mg, 0.04 mmol) and 2,2-difluorocyclopropanecarboxylic acid (10.9 mg, 0.08 mmol) in DMF (1 mL) were added 1-hydroxy-benzotriazole (10.8 mg, 0.08 mmol) and 1-(3-dimethylaminopropyl)-3-ethylcarbodiimide hydrochloride (12.4 mg, 0.08 mmol) and the resulting mixture was stirred for 1 h at 50° C. The mixture was quenched by addition of 2N HCl. The aqueous phase was extracted with ethyl acetate, and the organic phase was dried over sodium sulfate, and concentrated in vacuo. To a solution of the crude material in 1,4-dioxane (0.5 mL) was added sodium hydroxide (0.1 ml, 1.0 M in water, 0.1 mmol), and the resulting mixture was stirred at 60° C. After 15 min, the reaction mixture was rendered acidic by addition of 2N trifluoroacetic acid in DMSO, then was diluted with a mixture of 2:1 dioxane/water and passed through a 0.45 μm syringe filter. Purification by reverse phase HPLC (30 to 100% acetonitrile in water, each with 0.1% v/v TFA) provided the title compound: LCMS m/z 626.0 [M+H]$^+$; $^1$H NMR (500 MHz, acetone-d6) δ 8.22 (s, 1 H),7.80 (t, J=7.9 Hz, 1 H),7.62 (d, J=7.8 Hz, 1 H),7.51 (s, 1 H), 7.32 (d, J=1.0 Hz, 2 H),7.05-7.02 (m, 3 H),6.90 (d, J=8.8 Hz, 2 H),3.70 (t, J=5.2 Hz, 2 H), 3.64 (t, J=5.2 Hz, 2 H),3.32 (m, 1 H),3.20 (t, J=5.2 Hz, 2 H),3.17 (t, J=5.3 Hz, 2 H),2.93-2.74 (m, 4 H),2.41 (s, 3 H).

EXAMPLE 66

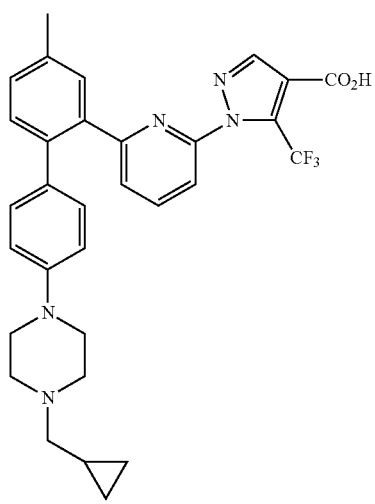 [SMILES: Cc1ccc(-c2ccc(N3CCN(CC4CC4)CC3)cc2)c(-c2cccc(-n3ncc(C(=O)O)c3C(F)(F)F)n2)c1]

1-(6-{4'-[4-(cyclopropylmethyl)piperazin-1-yl]-4-methylbiphenyl-2-yl}pyridin-2-yl)-5-(trifluoromethyl)-1H-pyrazole-4-carboxylic acid To a solution of the title compound from Example 63 Step C (32.2 mg, 0.06 mmol) and (bromomethyl)cyclopropane (16.2 mg, 0.12 mmol) in DMF (1 mL) was added cesium carbonate (58.8 mg, 0.18 mmol), and the resulting mixture was stirred at 50° C. for 30 min. The mixture was quenched by addition of 2N HCl. The aqueous phase was extracted with ethyl acetate, and the organic phase was dried over sodium sulfate, and concentrated in vacuo. To a solution of the crude material in 1,4-dioxane (0.5 mL) was added sodium hydroxide (0.1 mL, 1.0 M in water, 0.1 mmol), and the resulting mixture was stirred at 60° C. After 15 min, the reaction mixture was rendered acidic by addition of 2N trifluoroacetic acid in DMSO, then was diluted with a 2:1 mixture of dioxane:water and passed through a 0.45 μm syringe filter. Purification by reverse phase HPLC (30 to 100% acetonitrile in water, each with 0.1% v/v TFA) provided the title compound: LCMS m/z 561.9 [M+H]$^+$; $^1$H NMR (500 MHz, acetone-d$_6$) δ 8.22 (s, 1 H),7.81 (t, J=7.9 Hz, 1 H),7.61 (d, J=7.6 Hz, 1 H),7.51 (s, 1 H),7.32 (d, J=1.0 Hz, 2 H),7.07-7.04 (m, 3 H),6.95 (d, J=8.7 Hz, 2 H),3.40-2.88 (m, 8 H),3.15 (d, J=7.3 Hz, 2 H),2.41 (s, 3 H), 1.25 (m, 1 H),0.71 (m, 2 H),0.46 m, 2 H).

EXAMPLE 67

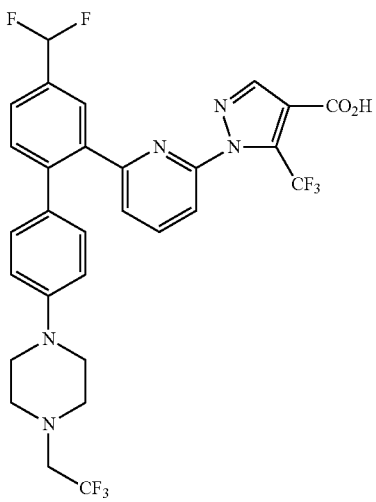 [SMILES: O=C(O)c1cnn(-c2cccc(-c3cc(C(F)F)ccc3-c3ccc(N4CCN(CC(F)(F)F)CC4)cc3)n2)c1C(F)(F)F]

Step A. 1-(4-bromophenyl)-4-(2,2,2-trifluoroethyl)piperazine

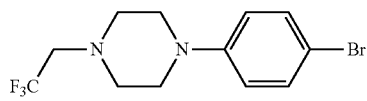

To a suspension of 1-(4-bromophenyl)piperazine (1.24 g, 5.16 mmol) in DCM were added 2,2,2-trifluoroethyl trifluoromethanesulfonate (1.20 mL, 7.22 mmol) and cesium carbonate (5.04 g, 15.0 mmol). The resulting mixture was stirred for 30 min. The reaction mixture was then quenched with saturated aqueous ammonium chloride solution, extracted with ethyl acetate, the organic layer was collected and concentrated in vacuo. Purification by chromatography on silica gel (0 to 100% EtOAc in hexanes) provided the title compound: LCMS m/z 324.8 [M+H]$^+$; $^1$H NMR (500 MHz, CDCl$_3$) δ 7.34 (d, J=9.1 Hz, 2 H), 6.78 (d, J=9.0 Hz, 2 H), 3.19-3.16 (m, 4 H), 3.03 (q, J=9.5 Hz, 2 H), 2.84-2.81 (m, 4 H).

Step B. 1-[4-(4,4,5,5-tetramethyl-1,3,2-dioxaborolan-2-yl)phenyl]-4-(2,2,2-trifluoroethyl)piperazine

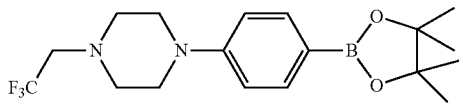 [SMILES: CC1(C)OB(c2ccc(N3CCN(CC(F)(F)F)CC3)cc2)OC1(C)C]

A round bottomed flask was charged with the title compound from the above Step A (0.15 g, 0.46 mmol), bis(pinacolato)diboron (0.18 g, 0.67 mmol), potassium acetate (0.09 g, 0.93 mmol), and 1,1'-bis(di t-butylphosphino)ferrocene palladium dichloride (0.04 g, 0.05 mmol). The flask was purged with nitrogen. Anhydrous 1,4-dioxane (5 mL) was added, and the resulting suspension was degassed via nitrogen sparge. The mixture was then placed in a pre-heated oil bath (85° C.), and was held at this temperature for 2 h, whereupon it was allowed to cool to ambient temperature, then was poured into water. The aqueous phase was extracted with ethyl acetate and the organic phase was washed with brine. The organic phase was then dried over anhydrous sodium sulfate and concentrated in vacuo. Purification by chromatography on silica gel (0 to 100% EtOAc in hexanes) provided the title compound: LCMS m/z 264.9 [M-C$_6$H$_{10}$+H]$^+$; $^1$H NMR (500 MHz, CD$_2$Cl$_2$) δ 7.62 (d, J=8.6 Hz, 2 H), 6.87 (d, J=8.5 Hz, 2 H), 3.28-3.25 (m, 4 H), 3.03 (q, J=9.7 Hz, 2 H), 2.82-2.78 (m, 4 H), 1.30 (s, 12 H).

Step C. ethyl 1-[6-(5-formyl-2-methoxyphenyl)pyridin-2-yl]-5-(trifluoromethyl-1H-pyrazole-4-carboxylate

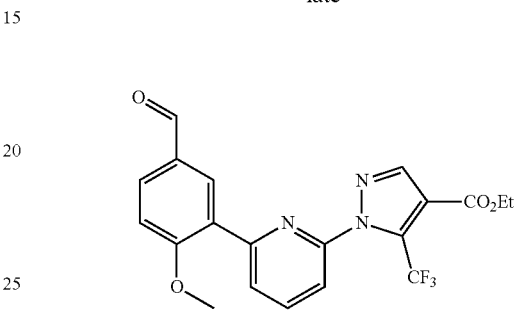

To a flask containing the title compound from Examples 1A and 1B Step A (1.78 g, 5.56 mmol) was added (5-formyl-2-methoxyphenyl)boronic acid (1.72 g, 9.46 mmol) and dichlorobis(triphenylphosphine) palladium (586 mg, 0.84 mmol). Acetonitrile (12 mL) and sodium carbonate (5.56 mL of 1.0 M aqueous solution, 5.56 mmol) were added, and the resulting mixture was degassed via nitrogen sparge. The reaction mixture was stirred at 80° C. for 18 h, then was allowed to cool to room temperature and was poured into water. The mixture was extracted with EtOAc, and the organic phase was concentrated in vacuo. Purification by chromatography on silica gel (0 to 100% EtOAc in hexanes) provided the title compound: LCMS m/z 419.7 [M+H]$^+$; $^1$H NMR (500 MHz, acetone-d$_6$) δ 9.98 (s, 1 H), 8.49 (d, J=2.2 Hz, 1H), 8.22 (m, 2 H), 8.16 (t, J=8.0 Hz, 1 H), 7.99 (dd, J=8.6, 2.1 Hz, 1 H), 7.76 (d, J=8.0 Hz, 1 H), 7.36 (d, J=8.6 Hz, 1 H), 4.36 (q, J=7.1 Hz, 2 H), 4.05 (s, 3 H), 1.36 (t, J=7.1 Hz, 3 H).

Step D. ethyl 1-{6-[5-(difluoromethyl)-2-methoxyphenyl]pyridin-2-yl}-5-(trifluoromethyl-1H-pyrazole-4-carboxylate

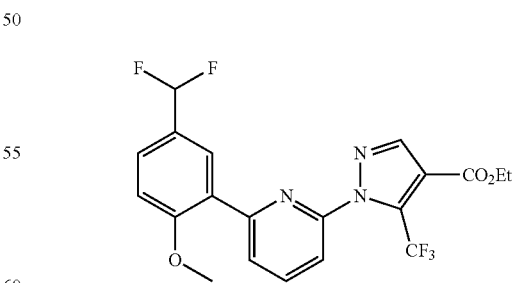

A teflon vial was charged with a solution of the title compound from the Step C above (0.83 g, 1.88 mmol) in DCM (15 mL). (Diethylamino)sulfur trifluoride (0.30 mL, 2.25 mmol) was added, and the resulting mixture was stirred at ambient temperature. After 18 h another 1 equivalent of DAST was added. Subsequently, another 1 equivalent was added after each 24 hour period for the next 3 days. The reaction mixture was quenched by addition of saturated aqueous sodium bicarbonate and was extracted with DCM. The organic phase was dried over anhydrous sodium sulfate, filtered, and concentrated in vacuo. Purification by chromatography on silica gel (0 to 100% EtOAc in hexanes) provided the title compound: LCMS m/z 441.8 [M+H]$^+$; $^1$H NMR (500 MHz, CD$_2$Cl$_2$) δ 8.17 (d, J=7.9 Hz, 1 H),8.14 (s, 1 H),8.11 (s, 1 H),7.98 (t, J=7.9 Hz, 1 H),7.62-7.56 (m, 2 H),7.13 (d, J=8.6 Hz, 1 H),6.68 (t, J=56.7 Hz, 1 H),4.37 (q, J=7.1 Hz, 2 H),1.38 (t, J=7.2 Hz, 3 H).

Step E. ethyl 1-{6-[5-(difluoromethyl)-2-hydroxyphenyl]pyridin-2-yl}-5-(trifluoromethyl)-1H-pyrazole-4-carboxylate

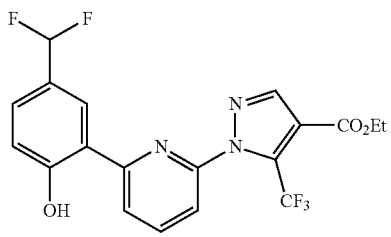 [SMILES: CCOC(=O)c1cnn(-c2cccc(-c3cc(C(F)F)ccc3O)n2)c1C(F)(F)F]

A plastic vial was charged with a solution of the title compound from the Step D above (0.83 g, 1.88 mmol) in DCM (10 mL). Iodo(trimethyl)silane (0.51 mL, 3.75 mmol) was added, and the resulting mixture was stirred at 80° C. for 2 h. The mixture was concentrated in vacuo, and the crude residue was azeotroped with toluene three times. The crude material was diluted with methanol and concentrated in vacuo. Purification by chromatography on silica gel (0 to 100% EtOAc in hexanes) provided the title compound: LCMS m/z 427.9 [M+H]$^+$; $^1$H NMR (500 MHz, CD$_2$Cl$_2$) δ 8.19-8.10 (m, 3 H),8.02 (s, 1 H),7.59 (d, J=7.5 Hz, 1 H),7.50 (d, J=8.4 Hz, 1 H),7.09 (d, J=7.5 Hz, 1 H),6.70 (t, J=56.6 Hz, 1 H),4.38 (q, J=7.1 Hz, 2 H),1.39 (t, J=7.1 Hz, 3 H).

Step F. ethyl 1-{6-[5-(difluoromethyl)-2-{[(trifluoromethyl)sulfonyl]oxy}phenyl]pyridin-2-yl}-5-(trifluoromethyl)-1H-pyrazole-4-carboxylate

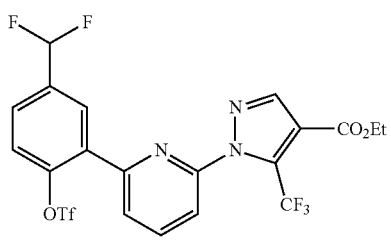 [SMILES: CCOC(=O)c1cnn(-c2cccc(-c3cc(C(F)F)ccc3OS(=O)(=O)C(F)(F)F)n2)c1C(F)(F)F]

To a vial containing the title compound from the Step E above (0.60 g, 1.40 mmol) in dichloromethane (10 mL), was added pyridine (0.34 mL, 4.20 mmol), and then reaction mixture was cooled to 0° C. Subsequently, triflic anhydride (0.36 mL, 2.10 mmol) was added dropwise. After stirring for 5 min the reaction mixture was allowed to warm to ambient temperature, then stirred for another 20 min. The reaction mixture was quenched with 2N HCl in water and then extracted with DCM. The organic phase was collected and concentrated in vacuo. Purification by flash chromatography on silica gel (0 to 100% EtOAc in hexanes) provided the title compound: LCMS m/z 559.6 [M+H]$^+$; $^1$H NMR (500 MHz, acetone-d6) δ 8.35 (t, J=8.0 Hz, 1 H), 8.23 (s, 1 H),8.16 (s, 1 H),8.08 (d, J=7.8 Hz, 1 H),7.94 (m, 2 H),7.79 (d, J=8.6 Hz, 1 H), 7.10 (t, J=55.7 Hz, 1 H),4.36 (q, J=7.1 Hz, 2 H),1.35 (t, J=7.1 Hz, 3 H).

Step G. 1-(6-{4-(difluoromethyl)-4'-[4-(2,2,2-trifluoroethyl)piperazin-1-yl]biphenyl-2-yl}pyridin-2-yl)-5-(trifluoromethyl)-1H-pyrazole-4-carboxylic acid To a flask containing the title compound from the Step F above (47.0 mg, 0.08 mmol) were added the title compound from the above Step B (46.7 mg, 0.13 mmol) and 1,1'-bis(di-tert-butylphosphino)ferrocene palladium dichloride (4.62 mg, 0.006 mmol). Acetonitrile (1 mL) and sodium carbonate (0.17 mL of 1.0 M aqueous solution, 0.17 mmol) were added, and the resulting mixture was degassed via nitrogen sparge. The reaction mixture was stirred at 85° C. for 2 h, then was allowed to cool to room temperature and was poured into water. The mixture was extracted with EtOAc, and the organic layer was concentrated in vacuo. To a solution of the crude material in 1,4-dioxane (0.5 mL) was added sodium hydroxide (0.15 mL of a 1.0 M solution in water, 0.15 mmol), and the resulting mixture was stirred at 60° C. After 15 min, the reaction mixture was rendered acidic by addition of 2N trifluoroacetic acid in DMSO, then was diluted with a 2:1 mixture of dioxane/water and passed through a 0.45 μm syringe filter. Purification by reverse phase HPLC (30 to 100% acetonitrile in water, each with 0.1% v/v TFA) provided the title compound: LCMS m/z 629.9 [M+H]$^+$; $^1$H NMR (500 MHz, CD$_2$Cl$_2$) δ 8.17 (s, 1 H),7.85 (s, 1 H),7.72 (t, J=7.9 Hz, 1 H),7.66 (d, J=8.0 Hz, 1 H),7.55-7.51 (m, 2 H), 7.23-7.14 (m, 4 H),7.09 (d, J=7.8 Hz, 1 H),6.77 (t, J=56.5 Hz, 1 H),3.44 (s, 4 H),3.20 (q, J=9.4 Hz, 2 H),3.09 (s, 4 H).

EXAMPLE 68A and 68B

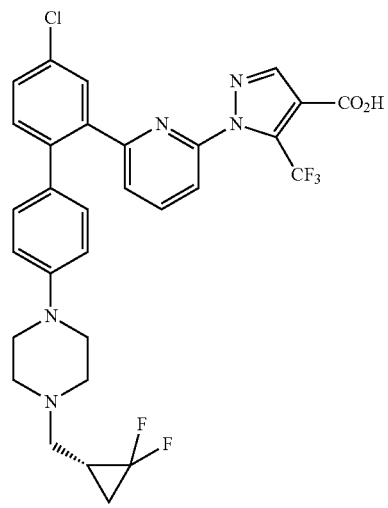

91

-continued

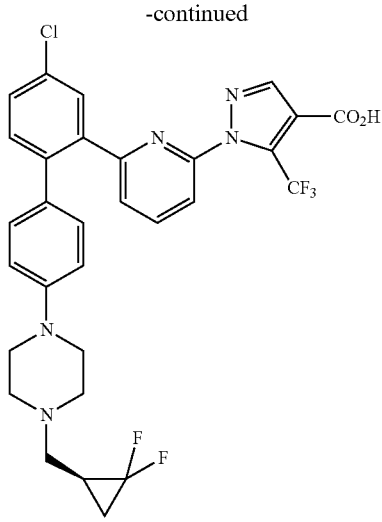

Step A. [4-(4-bromophenyl)piperazin-1-yl](2,2-difluorocyclopropyl)methanone, enantiomer A and enantiomer B To a solution of 1-(4-bromophenyl)piperazine (2.53 g, 10.5 mmol) in DMF (10 mL) was added 2,2-difluorocyclopropanecarboxylic acid (1.92 g, 15.7 mmol) 1H-benzotriazol-1-ol (2.84 g, 21.0 mmol), N-[3-(dimethylamino)propyl]-N'-ethylcarbodiimide (3.26 g, 21.0 mmol) and DIEA (7.31 mL, 42.0 mmol). The resulting mixture was stirred at 50° C. for 1 h. The reaction mixture was then quenched with saturated ammonium chloride solution, extracted with ethyl acetate, and concentrated in vacuo. Purification by chromatography on silica gel (0 to 75% EtOAc in hexanes, then 75 to 100% EtOAc in hexanes) provided the racemic compound. The racemate was then dissolved in 10% ethanol in heptane and the enantiomers were separated on an OD chiral column by eluting column with 30% ethanol in heptane. The first eluting peak was defined as enantiomer A and the second eluting peak was defined as enantiomer B. LCMS m/z 346.8 [M+H]$^+$; $^1$H NMR (500 MHz, CD$_2$Cl$_2$) δ 7.37 (d, J=9.0 Hz, 2 H),6.80 (d, J=9.0 Hz, 2 H), 4.00-3.93 (m, 1 H),3.84-3.61 (m, 3 H),3.31-3.02 (m, 4 H),2.60-2.50 (m, 1 H),2.23-2.11 (m, 1 H),1.75-1.64 (m, 1 H).

Step B. 1-[6-(4-chloro-4'-{4-[(2,2-difluorocyclopropyl)methyl]piperazin-1-yl}biphenyl-2-yl)pyridin-2-yl]-5-(trifluoromethyl)-1H-pyrazole-4-carboxylic acid, enantiomer A and enantiomer B To a round bottomed flask charged with product enantiomer A from Step A above (0.39 g, 1.14 mmol), was added excess borane-THF complex (11.4 mL, 1.0 M in THF, 11.4 mmol), then the reaction mixture was stirred at ambient temperature. After 1 h, the reaction was quenched with methanol, concentrated and then filtered through a silica plug eluting with ethyl acetate. The reaction mixture was then concentrated again in vacuo and the resulting free amine compound was used without further purification. 71.8 mg of this material (0.22 mmol) was added to a flask containing the title compound from Example 8 Step A (94.3 mg, 0.18 mmol), followed by the addition of dichloro bis(triphenylphosphine) palladium (19.0 mg, 0.03 mmol). Acetonitrile (2 mL) and sodium carbonate (0.36 mL, 1.0 M aqueous, 0.36 mmol) were added, and the resulting mixture was degassed via nitrogen

92 sparge. The reaction mixture was stirred at 85° C. for 2 h, then was allowed to cool to room temperature and was poured into water. The mixture was extracted with EtOAc, and the combined organic phase was concentrated in vacuo. To a solution of the crude material in 1,4-dioxane (0.5 mL) was added sodium hydroxide (0.3 mL, 1.0 M in water, 0.3 mmol), and the resulting mixture was stirred at 60° C. After 15 min, the reaction mixture was rendered acidic by addition of 2N trifluoroacetic acid in DMSO, then was diluted with a 2:1 mixture of dioxane:water and passed through a 0.45 μm syringe filter. Purification by reverse phase HPLC (30 to 100% acetonitrile in water, each with 0.1% v/v TFA) provided enantiomer A of the title compound. Employing the above procedure utilizing enantiomer B obtained from Step A above provided enantiomer B of the title compound. For both enantiomer A and B: LCMS m/z 617.9 [M+H]$^+$; $^1$H NMR (500 MHz, CD$_2$Cl$_2$) δ 8.14 (s, 1 H), 7.70-7.65 (m, 2 H),7.50-7.43 (m, 2 H),7.36 (d, J=8.2 Hz, 1 H),7.08-7.01 (m, 3 H),6.83 (d, J=8.6 Hz, 2 H),4.10-2.85 (m, 10 H),2.18-2.07 (m, 1 H),1.84-1.74 (m, 1 H),1.41-1.30 (m, 1 H).

EXAMPLE 69

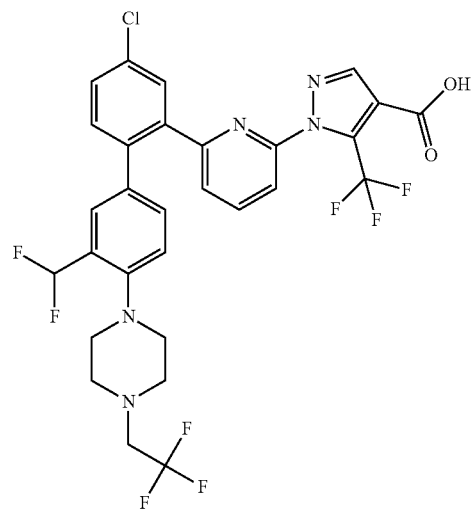 [SMILES: O=C(O)c1cnn(-c2cccc(-c3cc(Cl)ccc3-c3ccc(N4CCN(CC(F)(F)F)CC4)c(C(F)F)c3)n2)c1C(F)(F)F]

Step A. tert-butyl 4-(4-bromo-2-formylphenyl)piperazine-1-carboxylate

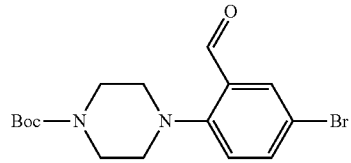 [SMILES: CC(C)(C)OC(=O)N1CCN(c2ccc(Br)cc2C=O)CC1]

To a solution of 5-bromo-2-fluorobenzaldehyde (1.62 g, 8.08 mmol) in NMP was added piperazine (1.39 g, 16.2 mmol) and DIEA (4.22 mL, 24.2 mmol). The resulting mixture was degassed via nitrogen sparge and stirred at 150° C. for 1 h. The mixture was added di-tert-butyl dicarbonate (3.52 g, 16.2 mmol) and stirred at ambient temperature for an additional 30 min. The reaction mixture was then quenched with 2N HCl in water, extracted with ethyl acetate, and the organic phase was dried with sodium sulfate and concentrated in vacuo. Purification by chromatography on silica gel (0 to 30% EtOAc in hexanes, then 30 to 100% EtOAc in hexanes) provided the title compound: LCMS m/z 312.7 [M-$^t$Bu+2H]$^+$; $^1$H NMR (500 MHz, acetone-d6) δ 10.27 (s, 1 H),7.82 (d, J=2.6 Hz, 1 H),7.72 (dd, J=8.7, J=2.5 Hz, 1 H),7.22 (d, J=8.7 Hz, 1 H), 3.62 (m, 2 H),3.07 (m, 2 H),2.81 (m, 2 H),2.04 (m, 2 H),1.43 (s, 9 H).

Step B. tert-butyl 4-[4-bromo-2-(difluoromethyl) phenyl]piperazine-1-carboxylate

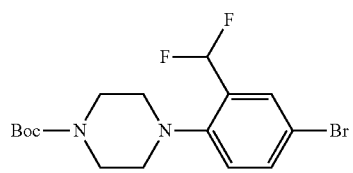 [SMILES: CC(C)(C)OC(=O)N1CCN(c2ccc(Br)cc2C(F)F)CC1]

To a solution of the title compound from the above Step A (500 mg, 1.37 mmol) in DCM (8 mL) was added DAST (0.5 mL, 3.77 mmol). The resulting mixture was stirred at ambient temperature overnight. Saturated aqueous sodium bicarbonate solution was added and the mixture was extracted twice with hexanes-EtOAc. After evaporation of the combined organic layers, the crude material was purified by flash chromatography on silica gel (96:4 then 9:1 hexanes:EtOAc, v/v) provided the title compound: LCMS m/z 336.8 [M-$^t$Bu+2H]$^+$, 292.8 [M-Boc+2H]$^+$. $^1$H NMR (400 MHz, CDCl$_3$) δ 7.75 (d, J=2.3 Hz, 1 H),7.54 (m, 1 H),7.05 (d, J=8.6 Hz, 1 H),6.98 (t, J=55.4 Hz, 1 H),3.55 (t, J=4.7 Hz, 4 H),2.84 (t, J=4.7 Hz, 4 H),1.47 (s, 9 H).

Step C. tert-butyl-4-[2-(difluoromethyl)-4-(4,4,5,5-tetramethyl-1,3,2-dioxaborolan-2-yl)phenyl]piperazine-1-carboxylate

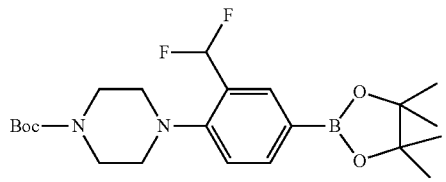 [SMILES: CC(C)(C)OC(=O)N1CCN(c2ccc(B3OC(C)(C)C(C)(C)O3)cc2C(F)F)CC1]

A mixture of the title compound from the Step B above (300 mg, 1.03 mmol), KOAc (250 mg, 2.55 mmol), bis(pinacolato)diboron (1300 mg, 18 mmol), and 1,1 bis(di-tert-butylphosphino)ferrocene palladium dichloride (50 mg, 0.078 mmol) in anhydrous 1,4-dioxane (10 mL) was stirred in a sealed vessel under nitrogen for 2 h at 80° C. After the reaction mixture was allowed to cool to ambient temperature, hexanes was added and the resulting mixture passed through a silica gel pad eluted by 25% EtOAc in hexanes. After concentration, the crude material was purified by flash chromatography on silica gel (5-10% EtOAc in hexanes) which provided the title compound: LCMS m/z 357.0 [M-C$_6$H$_{10}$+H]$^+$. $^1$H NMR (400 MHz, CDCl$_3$) δ 8.09 (s, 1 H), 7.85 (d, J=8.1 Hz, 1 H),7.12 (d, J=8.1 Hz, 1 H),7.00 (t, J=55.5 Hz, 1 H),3.56 (t, J=4.7 Hz, 4 H),2.89 (t, J=4.7 Hz, 4 H),1.47 (s, 9 H),1.32 (s, 12 H).

Step D. 1-(6-{4-chloro-3'-(difluoromethyl)-4'-[4-(2,2,2-trifluoroethyl)piperazin-1-yl]biphenyl-2-yl}pyridin-2-yl)-5-(trifluoromethyl)-1H-pyrazole-4-carboxylic acid Utilizing the title compound from the above Step C, and employing the method described in Examples 65A and 65B, the title compound was synthesized. LCMS m/z 660.0 [M+H]$^+$. $^1$H NMR (400 MHz, methanol-d$_4$) 8.12 (s, 1 H),7.79 (t, J=7.9 Hz, 1 H),7.64 (d, J=2.3 Hz, 1H), 7.56 (d, J=7.9 Hz, 1 H),7.52 (dd, J=8.3, 2.3 Hz, 1 H),7.42 (d, J=8.2 Hz, 1 H),7.31 (s, 1 H), 7.23 (d, J=8.2 Hz, 2 H),7.19 (d, J=8.4 Hz, 1 H),7.12 (d, J=8.7 Hz, 1 H),6.94 (t, J=55.5 Hz, 1 H),3.29 (m, 2 H),3.08-2.90 (m, 8 H).

EXAMPLE 70

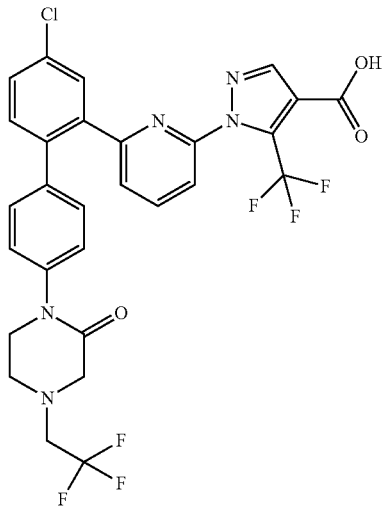 [SMILES: O=C(O)c1cnn(-c2cccc(-c3cc(Cl)ccc3-c3ccc(N4CCN(CC(F)(F)F)CC4=O)cc3)n2)c1C(F)(F)F]

Step A. tert-butyl 4-(4-bromophenyl)-3-oxopiperazine-1-carboxylate

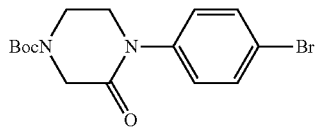

A mixture of 1-bromo-4-iodo benzene (1.00 g, 3.53 mmol), tert-butyl 3-oxopiperazine-1-carboxylate (0.71 g, 3.53 mmol), N,N'-dimethylethane-1,2-diamine (62 mg, 0.71 mmol), CuI (0.135 g, 0.71 mmol) and K$_3$PO$_4$ (2.25 g, 10.6 mmol) in DMF (50 mL) was stirred at 100° C. for 3 h. The mixture was partitioned between 0.1 N HCl and 2:1 hexanes:EtOAc. The organic layer was washed with saturated aq. NaHCO$_3$ and concentrated. Purification by chromatography on silica gel (20 to 35% EtOAc in hexanes provided the title compound: LCMS m/z 356.9 [M+H]$^+$. $^1$H NMR (400 MHz, CDCl$_3$) δ 7.52 (d, J=8.7 Hz, 2 H),7.17 (d, J=8.7 Hz, 2 H),4.23 (s, 2 H), 3.77 (m, 2 H),3.70 (m, 2 H),1.48 (s, 9 H).

Step B. tert-butyl 3-oxo-4-[4-(4,4,5,5-tetramethyl-1,3,2-dioxaborolan-2-yl)phenyl]piperazine-1-carboxylate

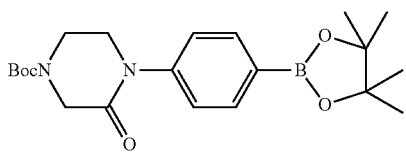 [SMILES: CC(C)(C)OC(=O)N1CCN(c2ccc(B3OC(C)(C)C(C)(C)O3)cc2)C(=O)C1]

A mixture of the title compound from the above Step A (400 mg, 1.12 mmol), KOAc (400 mg, 4.08 mmol), bis(pinacolato)diboron (500 mg, 1.97 mmol) and 1,1 bis(di-tert-butylphosphino)ferrocene palladium dichloride (50 mg, 0.078 mmol) were dissolved in anhydrous 1,4-dioxane (5 mL) and then stirred in a sealed vessel under nitrogen for 2 days in a 90° C. oil bath. The reaction mixture was diluted with hexanes and passed through a silica gel pad eluted by 25% EtOAc in hexanes. After concentration, the crude material was purified by flash chromatography on silica gel (20% EtOAc in hexanes) providing the title compound: LCMS m/z 403.0 [M+H]$^+$. $^1$H NMR (400 MHz, CDCl$_3$) δ 7.84 (d, J=8.3 Hz, 2 H), 7.29 (d, J=8.3 Hz, 2 H), 4.24 (s, 2 H), 3.75 (m, 4 H), 1.48 (s, 9 H), 1.32 (s, 12 H).

Step C. 1-(6-{4-chloro-4'-[2-oxo-4-(2,2,2-trifluoroethyl)piperazin-1-yl]biphenyl-2-yl}pyridin-2-yl)-5-(trifluoromethyl)-1H-pyrazole-4-carboxylic acid Utilizing the title compound from the above Step B, and employing the method described in Examples 65A and 65B, the title compound was synthesized. LCMS m/z 624.1 [M+H]$^+$. $^1$H NMR (400 MHz, acetone-d$_6$) δ (ppm) 8.18 (s, 1 H), 7.85 (t, J=7.9 Hz, 1 H), 7.67 (d, J=7.8 Hz, 1 H), 7.56 (dd, J=8.3, 2.3 Hz, 1 H), 7.28 (d, J=7.8 Hz, 1 H), 7.50 (d, J=8.2 Hz, 1 H), 7.33 (d, J=8.5 Hz, 2 H), 7.18 (d, J=8.5 Hz, 2 H), 7.10 (d, J=7.8 Hz, 1 H), 3.74 (m, 2 H), 3.48 (s, 2 H), 3.32 (m, 4 H).

The compounds in TABLES 2~4 were prepared using the chemistry described in Examples 60~70.

TABLE 2

| Example | X | R$^1$ | R$^3$ | R$^7$ | R$^5$ | MS [M + H]$^+$ |
|---|---|---|---|---|---|---|
| 71 | N | CF$_3$ | CF$_3$ | —C(=O)OMe | H | 688.0 |
| 72 | N | CF$_3$ | Cl | —C(=O)OMe | H | 654.0 |
| 73 | N | CF$_3$ | Cl | —CH$_2$CF$_3$ | H | 678.0 |
| 74 | CH | Cl | H | Me | H | 541.6 |
| 75 | CH | Cl | H | H | H | 526.8 |

TABLE 2-continued

| Example | X | R$^1$ | R$^3$ | R$^7$ | R$^5$ | MS [M + H]$^+$ |
|---|---|---|---|---|---|---|
| 76 | CH | Me | H | C(=O)-cyclopropyl (quaternary) | H | 570.0 |
| 77 | CH | Me | H | cyclopropylmethyl | H | 547.0 |
| 78 | CH | Me | H | S(=O)$_2$-cyclopropyl | H | 611.0 |
| 79 | CH | Me | H | S(=O)$_2$Me | H | 585.0 |
| 80 | CH | Me | H | C(=O)-(1-CF$_3$-cyclopropyl) | H | 642.9 |
| 81 | CH | Me | H | C(=O)-(1-CN-cyclopropyl) | H | 599.9 |
| 82 | CH | Me | H | C(=O)-(1-OH-cyclopropyl) | H | 590.9 |
| 83 | CH | Me | H | C(=O)-(1-NH$_2$-cyclopropyl) | H | 589.9 |
| 84 | CH | Me | H | C(=O)-(1-CH$_3$-cyclopropyl) | H | 588.9 |

TABLE 2-continued

| Example | X | R¹ | R³ | R⁷ | R⁵ | MS [M+H]⁺ |
|---|---|---|---|---|---|---|
| 85 | CH | Me | H | (1-oxo-2,2-difluorocyclopropyl) | H | 611.0 |
| 86 | CH | Me | H | (cyclobutyl, gem) | H | 561.0 |
| 87 | CH | Me | H | (CH₂-cyclopropyl) | H | 561.0 |
| 88 | CH | Me | H | (C(=O)-cyclobutyl) | H | 589.0 |
| 89 | CH | Me | H | —CH₂CF₃ | H | 588.9 |
| 90 | N | CF₃ | H | —CH₂CF₃ | I | 770.0 |
| 91 | CH | Cl | H | —CH₂CH₃ | H | 555.6 |
| 92 | CH | H | H | —CH₂CH₃ | H | 521.6 |
| 93 | CH | CF₃ | H | (C(=O)-cyclopropyl) | H | 629.7 |
| 94 | CH | Cl | H | (C(=O)-cyclopropyl) | H | 595.6 |
| 95 | CH | H | H | (C(=O)-cyclopropyl) | H | 561.6 |
| 96 | CH | Cl | H | (C(=O)-1-hydroxycyclopropyl) | H | 610.9 |
| 97 | CH | Cl | H | (C(=O)-cyclobutyl) | H | 608.9 |
| 98 | CH | Cl | H | —C(=O)OMe | H | 584.8 |
| 99 | CH | Cl | H | —C(=O)OEt | H | 598.9 |
| 100 | CH | F | H | (C(=O)-cyclopropyl) | H | 578.9 |
| 101 | CH | Cl | H | —C(=O)NMe₂ | H | 597.9 |
| 102 | CH | Cl | H | —C(=O)NEt₂ | H | 625.9 |
| 103 | CH | Cl | H | (C(=O)OCH₂CH₂F) | H | 616.9 |
| 104 | CH | Cl | H | (C(=O)OPr) | H | 612.9 |
| 105 | CH | Cl | H | (C(=O)OiPr) | H | 612.9 |
| 106 | CH | CF₂H | H | (C(=O)-cyclopropyl) | H | 610.9 |
| 107 | CH | CF₂H | H | —CH₂CF₃ | H | 624.9 |
| 108 | CH | OMe | H | (C(=O)-cyclopropyl) | H | 591.0 |
| 109 | CH | OMe | H | —CH₂CF₃ | H | 604.9 |
| 110 | N | CF₃ | H | (C(=O)-cyclopropyl) | H | 629.9 |
| 111 | CH | F | H | —CH₂CF₃ | H | 593.9 |
| 112 | CH | Cl | H | (CH(CF₃)-iPr) | H | 622.9 |

TABLE 2-continued

Structure: R1-substituted pyridine/pyrazine (with X) linked to central pyridine (R5) linked to pyrazole (CF3, COOH); central ring also bears phenyl with R3 and 4-piperidinyl-N-R7.

| Example | X | R¹ | R³ | R⁷ | R⁵ | MS [M + H]⁺ |
|---|---|---|---|---|---|---|
| 113 | CH | Me | H | —C(=O)OMe | H | 564.9 |
| 114 | CH | Me | H | —C(=O)OEt | H | 578.9 |
| 115 | N | CF₃ | H | —C(=O)OMe | H | 619.9 |
| 116 | N | CF₃ | H | —C(=O)OEt | H | 633.9 |
| 117 | N | Cl | H | —CH₂CF₃ | H | 609.9 |
| 118 | N | Cl | H | —C(=O)OMe | H | 587.0 |
| 119 | CH | Cl | Me | —CH₂CF₃ | H | 622.9 |
| 120 | CH | Cl | Me | —C(=O)OMe | H | 598.9 |
| 121 | CH | Cl | Me | —C(=O)OEt | H | 612.9 |
| 122 | CH | Cl | Me | cyclopropyl-C(=O)— | H | 609.0 |
| 123 | CH | Cl | Me | —S(=O)₂Me | H | 618.9 |
| 124 | CH | Cl | Me | —C(=O)NMe₂ | H | 612.0 |
| 125 | CH | F | F | —CH₂CF₃ | H | 611.0 |
| 126 | CH | F | F | —C(=O)OMe | H | 587.0 |
| 127 | CH | CF₃ | H | —C(=O)OMe | H | 619.0 |
| 128 (Ent. A) | CH | Cl | H | 2,2-difluorocyclopropyl-C(=O)— | H | 631.0 |
| 129 (Ent. B) | CH | Cl | H | 2,2-difluorocyclopropyl-C(=O)— | H | 631.0 |
| 130 (Ent. B) | CH | CF₃ | H | 2,2-difluorocyclopropyl-C(=O)— | H | 665.0 |
| 131 | CH | Cl | H | —C(=O)OCH₂CF₃ | H | 653.0 |
| 132 | CH | F | H | —C(=O)OEt | H | 583.0 |
| 133 | CH | F | H | —C(=O)OPr | H | 597.1 |
| 134 | CH | F | H | —C(=O)OCH₂CH₂F (gem-dimethyl) | H | 601.1 |
| 135 | CH | F | H | —C(=O)OCH₂CF₃ | H | 637.1 |
| 136 | CH | F | H | —CH₂CH₂CF₃ | H | 607.1 |
| 137 | CH | F | H | —CH(CF₃)₂ (1,1,1,3,3,3-hexafluoroisopropyl, methyl) | H | 675.1 |
| 138 | CH | F | Me | —CH₂CF₃ | H | 607.1 |
| 139 | N | Cl | Me | —CH₂CF₃ | H | 624.1 |
| 140 | N | CF₃ | Me | —CH₂CF₃ | H | 658.1 |
| 141 | CH | F | H | —C(CH₃)(CF₃)CHF₂ | H | 643.1 |
| 142 | CH | Cl | H | —C(CH₃)(CF₃)CHF₂ | H | 659.0 |
| 143 | N | CF₃ | Me | —C(=O)OMe | H | 634.0 |
| 144 | N | F | H | —CH₂CF₃ | H | 594.0 |
| 145 | N | F | Me | —CH₂CF₃ | H | 608.1 |

TABLE 3

Structure: R1a/R1b/R1c-substituted biphenyl linked to pyridine linked to pyrazole (CF3, COOH); biphenyl bears 4-piperidinyl with R8 and N-R7.

| Example | R¹ᵃ | R¹ᵇ | R¹ᶜ | R⁸ | R⁷ | MS |
|---|---|---|---|---|---|---|
| 146 | Me | H | H | OH | cyclopropyl-C(=O)— | 592.1 [M + H]⁺ |
| 147 | Me | H | H | F | cyclopropyl-C(=O)— | 573.1 [M − F]⁺ |

TABLE 3-continued

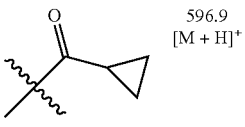

| Example | R¹ᵃ | R¹ᵇ | R¹ᶜ | R⁸ | R⁷ | MS |
|---|---|---|---|---|---|---|
| 148 | F | H | F | H | 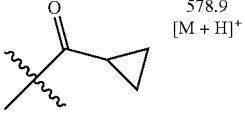 | 596.9 [M + H]⁺ |
| 149 | H | F | H | H | 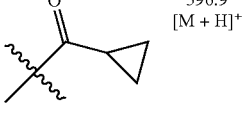 | 578.9 [M + H]⁺ |
| 150 | F | F | H | H | 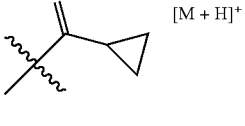 | 596.9 [M + H]⁺ |
| 151 | Cl | H | H | H |  | 612.9 [M + H]⁺ |
| 152 | Cl | H | H | F | —C(=O)OMe | 583.5 [M − F]⁺ |
| 153 | Cl | H | H | F | —C(=O)OEt | 598.0 [M − F]⁺ |

TABLE 4

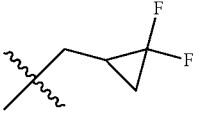 [SMILES: *CC1CC1(F)F]

| Example | X | R¹ | R³ | R⁷ | MS [M + H]⁺ |
|---|---|---|---|---|---|
| 154 | CH | Me | H | Me | 522.0 |
| 155 | N | Cl | H | —CH₂CF₃ | 610.8 |
| 156 | N | CF₃ | H | —C(=O)OMe | 620.9 |
| 157 | N | CF₃ | H | —CH₂CF₃ | 644.9 |
| 158 | N | Cl | H | —C(=O)OMe | 586.8 |
| 159 | CH | Cl | Me | —CH₂CF₃ | 623.9 |
| 160 | CH | Cl | Me |  | 596.0 |

TABLE 4-continued

| Example | X | R¹ | R³ | R⁷ | MS [M + H]⁺ |
|---|---|---|---|---|---|
| 161 | CH | CF₂H | Cl | —CH₂CF₃ | 659.9 |
| 162 (Ent. A) | CH | Cl | F | 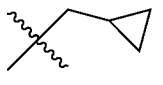 | 636.0 |
| 163 (Ent. B) | CH | Cl | F | | 636.0 |
| 164 | CH | CF₂H | H | —CH₂CH₂CF₃ | 640.1 |
| 165 | CH | Cl | CF₂H | —CH₂CH₂CF₃ | 674.0 |
| 166 | CH | CF₃ | H | —CH₂CH₂CF₃ | 658.1 |
| 167 (Ent. A) | CH | CF₃ | H | | 652.1 |
| 168 (Ent. B) | CH | CF₃ | H | | 652.1 |
| 169 | CH | Cl | H | 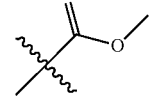 | 585.7 |
| 170 | CH | Cl | H | 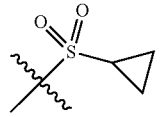 [SMILES: *S(=O)(=O)C1CC1] | 631.7 |
| 171 | CH | Cl | H | 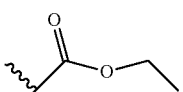 | 599.7 |
| 172 | CH | Cl | H | 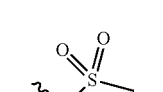 | 605.7 |

TABLE 4-continued
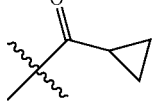
| Example | X | R¹ | R³ | R⁷ | MS [M + H]⁺ |
|---|---|---|---|---|---|
| 173 | CH | Cl | H | 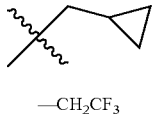 | 595.7 |
| 174 | CH | Cl | H | 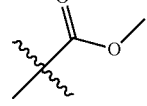 | 581.8 |
| 175 | CH | Cl | H | —CH₂CF₃ | 609.7 |
| 176 | CH | CH₃ | H | 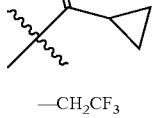 | 565.8 |
| 177 | CH | CH₃ | H | 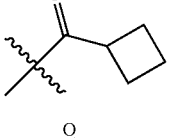 | 575.8 |
| 178 | CH | CH₃ | H | —CH₂CF₃ | 589.8 |
| 179 | CH | Cl | H | 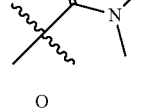 | 609.8 |
| 180 | CH | Cl | H | 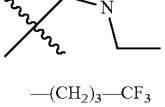 | 598.7 |
| 181 | CH | Cl | H |  | 626.8 |
| 182 | CH | Cl | H | —(CH₂)₃—CF₃ | 637.8 |
| 183 | CH | Cl | H | 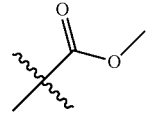 [SMILES: *C(=O)OC] | 568.6 |
| 184 | CH | CF₃ | H | —CH₂CF₃ | 643.8 |
| 185 | CH | F | H | —CH₂CF₃ | 593.8 |
| 186 | CH | CF₃ | H | 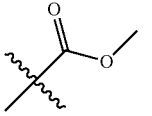 [SMILES: *C(=O)OC] | 619.8 |
| 187 | CH | F | H | 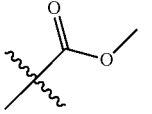 [SMILES: *C(=O)OC] | 569.8 |
| 188 | CH | Cl | H | —CH₃ | 541.8 |
| 189 | CH | CF₂H | H |  | 601.8 |
| 190 (Ent.A) | CH | Cl | H |  | 617.8 |
| 191 | CH | CH₃ | H | 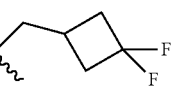 | 579.8 |
| 192 | CH | Cl | H | 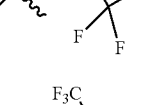 | 595.9 |
| 193 | CH | Cl | H | 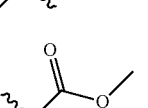 | 631.8 |
| 194 (racemic) | CH | Cl | H | 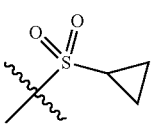 [SMILES: *S(=O)(=O)C1CC1] | 631.8 |
| 195 | CH | Cl | H |  | 649.8 |
| 196 | CH | Cl | Cl |  | 619.8 |
| 197 | CH | Cl | Cl |  | 665.7 |

TABLE 4-continued

| Example | X | R¹ | R³ | R⁷ | MS [M + H]⁺ |
|---|---|---|---|---|---|
| 198 (racemic) | CH | Cl | Cl | 2,2-difluorocyclopropylmethyl | 652.6 |
| 199 | CH | Cl | Cl | cyclopropylmethyl | 615.7 |
| 200 | CH | Cl | Cl | —CH₂CF₃ | 643.7 |
| 201 | CH | Cl | Cl | ethoxycarbonylmethyl | 633.7 |
| 202 | CH | Cl | Cl | N,N-dimethylcarbamoylmethyl | 632.8 |
| 203 | CH | Cl | Cl | cyclopropylcarbonyl | 629.8 |
| 204 | CH | F | Cl | —CH₂CF₃ | 627.9 |
| 205 | CH | F | Cl | methoxycarbonylmethyl | 603.9 |
| 206 | CH | Cl | H | —(CH₂)₂CF₃ | 623.83 |
| 207 (Ent A) | CH | Cl | H | 2,2-difluorocyclobutylmethyl | 631.9 |
| 208 | CH | Cl | F | —CH₂CF₃ | 627.8 |
| 209 (Ent B) | CH | Cl | H | 2,2-difluorocyclobutylmethyl | 631.8 |
| 210 | CH | Cl | H | 2-fluorocyclopropylmethyl | 600.0 |
| 211 | CH | Cl | Cl | —(CH₂)₂CF₃ | 657.8 |
| 212 (Ent. A) | CH | CF₂H | H | 2,2-difluorocyclopropylmethyl | 633.9 |
| 213 (Ent. B) | CH | CF₂H | H | 2,2-difluorocyclopropylmethyl | 633.9 |
| 214 | CH | Cl | F | —(CH₂)₂CF₃ | 641.8 |
| 215 | CH | CF₃ | H | cyclopropylcarbonyl | 630.2 |
| 216 (Ent.A) | CH | CF₃ | H | 2,2-difluorocyclopropylcarbonyl | 665.9 |
| 217 (Ent.B) | CH | CF₃ | H | 2,2-difluorocyclopropylcarbonyl | 665.9 |
| 218 (Ent A) | CH | CF₃ | H | 2,2-difluorocyclobutylmethyl | 666.0 |
| 219 | CH | F | H | —(CH₂)₂CF₃ | 641.8 |
| 220 (Ent. A) | CH | F | H | 2,2-difluorocyclopropylmethyl | 602.0 |
| 221 (Ent. B) | CH | F | H | 2,2-difluorocyclopropylmethyl | 601.9 |
| 222 | CH | Cl | H | —CH₂CF₂CF₃ | 659.8 |
| 223 | CH | F | H | —CH₂CF₂CF₃ | 644.0 |
| 224 | CH | H | H | —(CH₂)₂CF₃ | 589.2 |

EXAMPLE 225

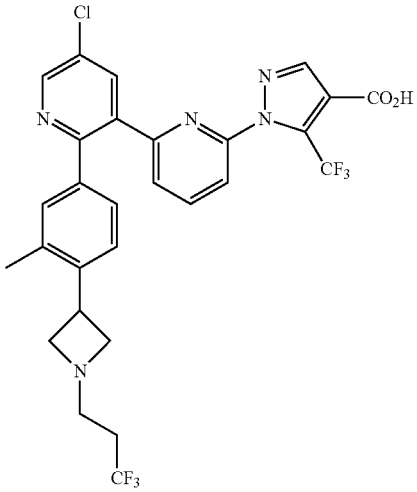 [SMILES: Cc1cc(-c2ncc(Cl)cc2-c2cccc(-n3ncc(C(=O)O)c3C(F)(F)F)n2)ccc1C1CN(CCC(F)(F)F)C1]

Step A. tert-butyl 3-(4-bromo-2-methylphenyl)azetidine-1-carboxylate

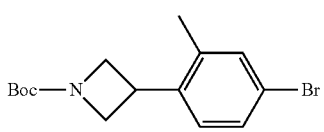 [SMILES: Cc1cc(Br)ccc1C1CN(C(=O)OC(C)(C)C)C1]

To a vial with zinc dust (2.77 g, 42.4 mmol) in anhydrous THF (15 mL) under nitrogen was added 1,2-dibromoethane (0.24 mL, 2.83 mmol), then the suspension was stirred at 65° C. for 3 min. After cooling to ambient temperature, chloro(trimethyl)silane (0.36 mL, 2.83 mmol) was added and the mixture was stirred at room temperature for 30 min. Then, a solution of tert-butyl 3-iodoazetidine-1-carboxylate (8.00 g, 28.3 mmol) in THF (10 mL) was added and the mixture was stirred for 45 min. P(2-furyl)$_3$ (1.31 g, 5.7 mmol) and tris(dibenzylidene acetone)dipalladium (0) (2.59 g, 2.83 mmol) were added to a separate vial, dissolved in THF (5 mL) and stirred under nitrogen at ambient temperature for 10 min, then the mixture and 5-bromo-2-iodotoluene (4.84 mL, 33.9 mmol) in THF (10 mL) were added to the organozine reagent solution. The mixture was then placed in a 65° C. oil bath for 2 h. The reaction mixture was allowed to cool to room temperature and then was poured into water. The mixture was extracted with EtOAc, and the organic layer was concentrated in vacuo. Purification by chromatography on silica gel (0 to 50% EtOAc in hexanes, then 50 to 100% EtOAc in hexanes) provided the title compound: LCMS m/z 271.8 [M-t-Bu+2H]$^+$; $^1$H NMR (500 MHz, acetone-d6) δ 7.40-7.30 (m, 3 H),4.23 (br, 2 H),3.99 (m, 1 H),3.91 (m, 2 H),2.21 (s, 3 H),1.42 (s, 9 H).

Step B. tert-butyl 3-[2-methyl-4-(4,4,5,5-tetramethyl-1,3,2-dioxaborolan-2-yl)-phenyl]azetidine-1-carboxylate

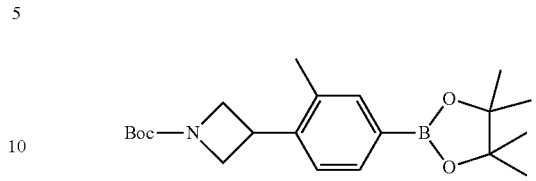

A round bottomed flask was charged with the title compound from the above Step A (0.46 g, 1.41 mmol), bis(pinacolato)diboron (0.54 g, 2.11 mmol), potassium acetate (0.35 g, 3.52 mmol), and [1,1'-bis(diphenylphosphino) ferrocene] palladium(II) dichloromethane adduct (0.12 g, 0.14 mmol). The flask was purged with nitrogen. Anhydrous 1,4 dioxane (15 mL) was added, and the resulting suspension was degassed via nitrogen sparge. The mixture was then placed in a pre-heated oil bath (85° C.) for 2 h, whereupon it was allowed to cool to ambient temperature, then was poured into water. The aqueous phase was extracted with ethyl acetate and the organic phase was washed with brine. The organic phase was dried over anhydrous sodium sulfate and concentrated in vacuo. Purification by chromatography on silica gel (0 to 30% EtOAc in hexanes, then 30 to 100% EtOAc in hexanes) provided the title compound: LCMS m/z 236.0 [M-C$_6$H$_{10}$-tBu+2H]J; $^1$H NMR (500 MHz, acetone-d$_6$) δ 7.61 (d, J=7.6 Hz, 1 H),7.53 (s, 1 H),7.39 (d, J=7.6 Hz, 1 H),4.29 (br, 2 H),4.05 (m, 1 H),3.93 (m, 2 H),2.22 (s, 3 H),1.42 (s, 9 H),1.32 (s, 12 H).

Step C. ethyl 1-{2'-[4-(azetidin-3-yl)-3-methylphenyl]-5'-(trifluoromethyl)-2,3'-bipyridin-6-yl}-5-(trifluoromethyl)-1H-pyrazole-4-carboxylate

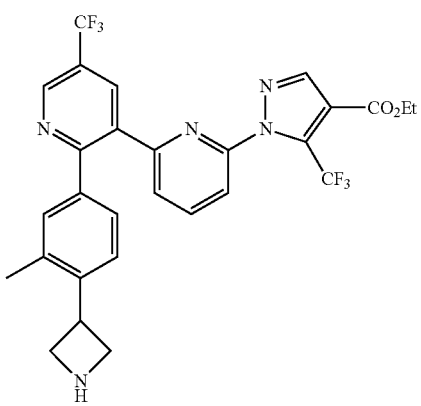 [SMILES: CCOC(=O)c1cnn(-c2cccc(-c3cc(C(F)(F)F)cnc3-c3ccc(C4CNC4)c(C)c3)n2)c1C(F)(F)F]

To a flask containing the title compound from Example 61 Step D (127 mg, 0.22 mmol) were added the title compound from the Step B above (114 mg, 0.31 mmol) and 1,1'-bis(di t-butylphosphino)ferrocene palladium dichloride (17.9 mg, 0.02 mmol). Acetonitrile (5 mL) and sodium carbonate (0.44 mL, 1.0 M aqueous, 0.44 mmol) were added, and the resulting mixture was degassed via nitrogen sparge. The reaction mixture was stirred at 80° C. for 1.5 h, then was allowed to cool to room temperature and was poured into water. The mixture was extracted with EtOAc, and the organic phase was collected and concentrated in vacuo. Purification by chromatography on silica gel (0 to 25% EtOAc in hexanes, then 30 to 100% EtOAc in hexanes) provided the N-Boc protected azetidine compound. Deprotection was carried out by dissolving the Boc protected intermediate in DCM (5 mL) followed by the addition of 1 mL of trifluoroacetic acid and stirring for 20 min. The reaction mixture was concentrated and the remaining trifluoroacetic acid was azeotroped three times with toluene. The resulting azetidine product was used without further purification: LCMS m/z 576.0 [M+H]+; 1H NMR (500 MHz, acetone-d6) δ 9.05 (s, 1 H),8.47 (s, 1 H),8.14 (s, 1 H),7.75 (t, J=7.9 Hz, 1 H),7.66 (d, J=7.9 Hz, 1 H),7.29 (s, 1 H),7.26 (s, 2 H),7.07 (d, J=7.7 Hz, 1 H),4.56-4.28 (m, 7 H),2.16 (s, 3 H), 1.38 (t, J=7.1 Hz, 3 H), 1.38 (t, J=7.1 Hz, 3 H).

Step D. 1-(6-{4-chloro-3'-methyl-4'-[1-(3,3,3-trifluoropropyl azetidin-3-yl]biphenyl-2-yl}pyridin-2-yl)-5-trifluoromethyl)-1H-pyrazole-4-carboxylic acid To a solution of the title compound from the above Step C (26.8 mg, 0.05 mmol) and 3-bromo-1,1,1-trifluoropropane (16.5 mg, 0.09 mmol) ACN (1 mL) was added DIEA (12.0 mg, 0.09 mmol), and the resulting mixture was stirred for 2 h at 90° C. The reaction mixture was concentrated in. The crude material was taken up in 1,4-dioxane (0.5 mL). Sodium hydroxide (0.1 mL of 1.0 M solution in water, 0.1 mmol), was added and the resulting mixture was stirred at 60° C. After 15 min, the reaction mixture was rendered acidic by addition of 2N trifluoroacetic acid in DMSO, then was diluted with a 2:1 mixture of dioxane/water and passed through a 0.45 µm syringe filter. Purification by reverse phase HPLC (30 to 100% acetonitrile in water, each with 0.1% v/v TFA) provided the title compound: LCMS m/z 644.0 [M+H]+; 1H NMR (500 MHz, acetone-d6) δ 9.09 (s, 1 H),8.40 (s, 1 H),8.25 (s, 1 H),7.97 (t, J=7.9 Hz, 1 H), 7.81 (d, J=8.0 Hz, 1 H),7.43-7.32 (m, 3 H),7.27 (d, J=8.4 Hz, 1 H),4.70 (br, 2 H),4.54 (br, 1 H),4.38 (br, 2 H),3.68 (br, 2 H),2.81 (m, 2 H),2.22 (s, 3 H).

EXAMPLE 226A and 226B

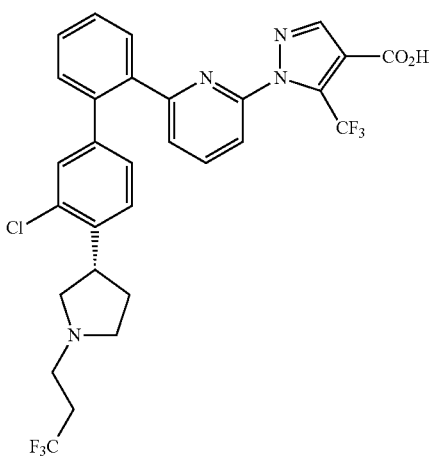

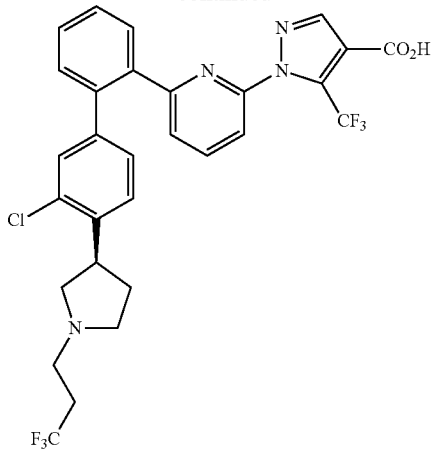

Step A. tert-butyl 3-(4-bromo-2-chlorophenyl-2,5-dihydro-1H-pyrrole-1-carboxylate

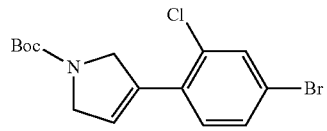 [SMILES: CC(C)(C)OC(=O)N1CC=C(c2ccc(Br)cc2Cl)C1]

To a flask containing 4-bromo-2-chloro-1-iodobenzene (415 mg, 1.31 mmol) were added tert-butyl 3-(4,4,5,5-tetramethyl-1,3,2-dioxaborolan-2-yl)-2,5-dihydro-1H-pyrrole-1-carboxylate (504 mg, 0.93 mmol) and dichloro bis(triphenylphosphine) palladium (65.0 mg, 0.09 mmol). Acetonitrile (5 mL) and sodium carbonate (1.85 mL of a 1.0 M aqueous solution, 1.85 mmol) were added, and the resulting mixture was degassed via nitrogen sparge. The reaction mixture was stirred at 80° C. for 16 h, then was allowed to cool to room temperature and was poured into water. The mixture was extracted with EtOAc, the organic phase was collected and concentrated in vacuo. Purification by chromatography on silica gel (0 to 25% EtOAc in hexanes, then 30 to 100% EtOAc in hexanes) provided the title compound. LCMS m/z 301.8 [M-tBu+2H]+.

Step B. benzyl 3-(4-bromo-2-chlorophenyl)pyrrolidine-1-carboxylate, enantiomer A and enantiomer B

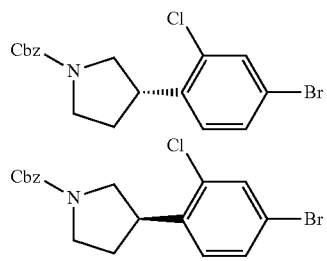

To a degassed solution of the title compound from the above Step A (469 mg, 1.31 mmol) in EtOAc:EtOH (8:2 mL) was added platinum(IV) oxide (188 mg, 0.83 mmol). The reaction flask was fitted with a 3-way adapter fitted with a hydrogen balloon. The reaction flask was then evacuated and back-filled with hydrogen. After this process was repeated three times, the reaction mixture was stirred vigorously. After 30 min, the reaction mixture was filtered through Celite, rinsing with EtOAc and the combined organic phase was concentrated. The crude product was dissolved in DCM (10 mL) to which was added trifluoroacetic acid (3 mL) and the reaction mixture was stirred at ambient temperature for 30 min. The reaction mixture was concentrated and azeotroped three times with toluene to provide the crude pyrrolidine. To a solution of the crude pyrrolidine in acetonitrile was added benzyl chloroformate (0.24 mL, 1.70 mmol) and DIEA (0.57 mL, 3.27 mmol), then the reaction mixture was stirred for 1 h at ambient temperature. The reaction mixture was quenched with sodium bicarbonate and extracted with EtOAc. The organic phase was collected, then dried with sodium sulfate and concentrated. Purification by chromatography on silica gel (0 to 25% EtOAc in hexanes, then 30 to 100% EtOAc in hexanes) provided the racemic compound. The enantiomers were then separated on a chiral OJ column eluting with 60% IPA in heptane. The first eluting peak was defined as enantiomer A and the second eluting peak was defined as enantiomer B. The separated enantiomers were collected, concentrated and taken individually to the following step. For both enantiomers: LCMS m/z 393.8 [M+H].

Step C. 1-(6-{3'-chloro-4'-[1-(3,3,3-trifluoropropyl)pyrrolidin-3-yl]biphenyl-2-yl}pyridin-2-yl)-5-(trifluoromethyl)-1H-pyrazole-4-carboxylic acid, enantiomer A and enantiomer B To a flask containing product enantiomer A from Step B above (45.9 mg, 0.12 mmol) were added the title compound from Example 5 Step D (79.0 mg, 0.15 mmol) and dichloro bis(triphenylphosphine) palladium (8.15 mg, 0.01 mmol). Acetonitrile (1 mL) and sodium carbonate (0.23 mL of 1.0 M aqueous solution, 0.23 mmol) were added, and the resulting mixture was degassed via nitrogen sparge. The reaction mixture was stirred at 80° C. for 16 h, then was allowed to cool to room temperature and was poured into water. The mixture was extracted with EtOAc, and the organic was concentrated in vacuo. Purification by chromatography on silica gel (0 to 25% then 30 to 100% EtOAc in hex) provided the Cbz-protected chiral compound. LCMS m/z 709.0 [M+H]$^+$. To the protected product dissolved in EtOAc:EtOH (4:1 mL) was added platinum(IV) oxide (30 mg). The reaction flask was fitted with a 3-way adapter with a hydrogen balloon attached. The reaction flask was then evacuated and back-filled with hydrogen. After this process was repeated three times, the reaction mixture was stirred vigorously. After 20 min, the reaction mixture was filtered through Celite, rinsing with EtOAc and combined filtrates were concentrated. The crude product dissolved in acetonitrile (10 mL) was subsequently alkylated by the addition of approximately 0.1 mL each of 3-bromo-1,1,1-trifluoropropane and DIEA, then was stirred at 90° C. for 2 h. The reaction mixture was then concentrated. To a solution of the crude material in 1,4-dioxane (2 mL) was added sodium hydroxide (0.4 mL, 1.0 M in water, 0.4 mmol), and the resulting mixture was stirred at 60° C. After 15 min, the reaction mixture was rendered acidic by addition of 2 N trifluoroacetic acid in DMSO, then was diluted with a 2:1 mixture of dioxane:water and passed through a 0.45 rpm syringe filter. Purification by reverse phase HPLC (30 to 100% acetonitrile in water, each with 0.1% v/v TFA) provided enantiomer A of the title compound. Employing the above procedure utilizing enantiomer B obtained from Step A above provided enantiomer B of the title compound. For both enantiomer A and B: LCMS m/z 608.9 [M+H]$^+$; $^1$H NMR (500 MHz, acetone-d$_6$) δ 8.21 (s, 1 H),7.90 (t, J=7.8 Hz, 1 H),7.73-7.69 (m, 1 H),7.66 (d, J=7.7 Hz, 1 H),7.58-7.55 (m, 2 H),7.52-7.48 (m, 2 H),7.29-7.25 (m, 1 H),7.22 (d, J=7.7 Hz, 1 H), 7.13-7.08 (m, 1 H),4.21-4.07 (m, 1 H),3.68-3.59 (m, 3 H),3.03-2.88 (m, 4 H),2.60-2.49 (m, 1 H), 2.30-2.20 (m, 1 H),1.35-1.25 (m, 1 H).

The compounds in TABLE 5 and 6 were prepared using the chemistry described in Examples 225, 226A and 226B.

TABLE 5

| Example | X | R$^1$ | R$^3$ | R$^7$ | MS [M + H]$^+$ |
|---|---|---|---|---|---|
| 227 | CH | Cl | H | —C(O)-cyclopropyl | 566.8 |
| 228 | CH | Cl | H | —CH$_2$CF$_3$ | 580.7 |
| 229 | CH | Cl | H | —C(O)OCH$_3$ | 556.8 |
| 230 | CH | Cl | H | —S(O)$_2$-cyclopropyl | 602.7 |
| 231 (racemic) | CH | Cl | H | —CH$_2$-(1-F-cyclopropyl)-F | 588.9 |
| 232 | CH | Cl | H | —(CH)$_3$CF$_3$ | 608.9 |
| 233 | CH | Cl | H | —(CH)$_2$CF$_3$ | 594.9 |
| 234 | CH | Cl | H | —C(O)OCH$_2$CF$_3$ | 624.9 |
| 235 | CH | Cl | H | —C(O)CH$_2$CF$_3$ | 622.9 |
| 236 | CH | CF$_3$ | H | —C(O)OCH$_2$CH$_3$ | 618.9 |

TABLE 5-continued

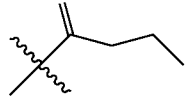

| Example | X | R¹ | R³ | R⁷ | MS [M + H]⁺ |
|---|---|---|---|---|---|
| 237 | CH | CF₃ | H | —(CH₂)₂CF₃ | 628.93 |
| 238 | CH | CF₃ | H | —(CH₂)₃CF₃ | 643.0 |
| 239 | CH | CF₃ | H | 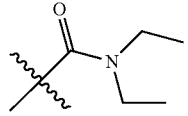 [SMILES: *C(=O)N(CC)CC] | 602.9 |
| 240 | CH | Cl | Me | —(CH₂)₂CF₃ | 608.9 |
| 241 | CH | Cl | Me | —(CH₂)₃CF₃ | 622.9 |
| 242 | CH | Cl | Me | 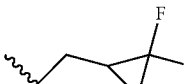 | 612.0 |
| 243 | CH | Cl | H | —CH₂CF₂CF₃ | 630.9 |
| 244 | CH | Cl | Me | —CH₂CF₂CF₃ | 644.9 |
| 245 | CH | Cl | Me | —CH₂CF₃ | 594.9 |
| 246 | CH | CF₃ | Me | —(CH₂)₂CF₃ | 642.9 |
| 247 | CH | CF₃ | Me | —CH₂CF₃ | 628.9 |
| 248 | CH | CF₃ | Me | —CH₂CF₂CF₃ | 678.9 |
| 249 | CH | Cl | Cl | —(CH₂)₂CF₃ | 628.9 |
| 250 (racemic) | CH | Cl | Cl | 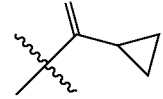 | 622.9 |
| 251 | CH | Cl | Cl | —(CH₂)₃CF₃ | 642.9 |
| 252 | CH | Cl | Cl | —CH₂CF₃ | 614.9 |
| 253 | CH | F | Me | —(CH₂)₂CF₃ | 593.0 |
| 254 | CH | F | Me | —CH₂CF₃ | 578.9 |
| 255 | CH | F | Cl | —(CH₂)₂CF₃ | 613.0 |
| 256 | CH | Cl | Cl | —(CH₂)₂OCH₃ | 590.9 |
| 257 | CH | Cl | Cl | —CH₂CH(OCH₃)₂ | 621.0 |
| 258 | N | CF₃ | Me | —CH₂CF₃ | 630.0 |
| 259 | N | CF₃ | Cl | —(CH₂)₂CF₃ | 663.9 |
| 260 | N | CF₃ | Cl | —CH₂CF₃ | 649.9 |

TABLE 6

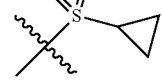

| Example | R¹ | R³ | R⁷ | MS [M + H]⁺ |
|---|---|---|---|---|
| 261 (racemic) | Cl | H | 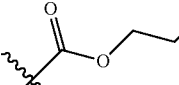 | 581.0 |
| 262 (racemic) | Cl | H | —CH₂CF₃ | 595.0 |
| 263 (racemic) | Cl | H | —CH₂CH₂CF₃ | 609.0 |
| 264 (racemic) | Cl | H | 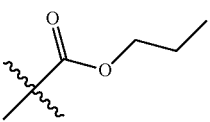 [SMILES: *C(=O)OCCC] | 616.9 |
| 265 (racemic) | Cl | H |  | 599.0 |
| 266 (Ent. A) | Cl | H | —CH₂CH₂CF₃ | 609.1 |
| 267 (Ent. B) | Cl | H | —CH₂CH₂CF₃ | 609.1 |
| 268 (Ent. A) | H | H | —CH₂CH₂CF₃ | 575.1 |
| 269 (Ent. B) | H | H | —CH₂CH₂CF₃ | 575.1 |
| 270 (Ent. A) | Cl | H | —CH₂CH₂CH₂CF₃ | 623.1 |
| 271 (Ent. A) | H | H | —CH₂CH₂CH₂CF₃ | 589.0 |
| 272 (Ent. A) | CF₃ | H | —CH₂CH₂CF₃ | 643.1 |
| 273 (Ent. B) | CF₃ | H | —CH₂CH₂CF₃ | 643.1 |
| 274 (Ent. A) | CF₃ | H | —CH₂CH₂CH₂CF₃ | 657.1 |
| 275 (Ent. A) | CF₃ | H | 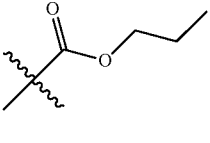 [SMILES: *C(=O)OCCC] | 633.1 |
| 276 (Ent. B) | CF₃ | H | 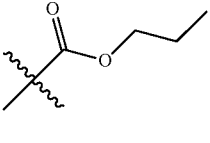 [SMILES: *C(=O)OCCC] | 633.1 |
| 277 (Ent. A) | Cl | H | 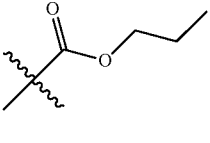 [SMILES: *C(=O)OCCC] | 599.1 |

TABLE 6-continued

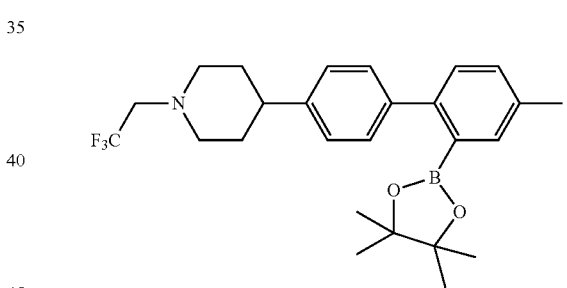

| Example | R¹ | R³ | R⁷ | MS [M + H]⁺ |
|---|---|---|---|---|
| 278 (Ent. B) | Cl | H | ![ester group] | 599.1 |
| 279 (racemic) | Cl | Me | —CH₂CH₂CF₃ | 623.0 |
| 280 (Ent. A) | Cl | H | ![CF₃/CF₃ group] | 677.0 |
| 281 (Ent. B) | Cl | H | ![F,F/CF₃ group] | 645.1 |
| 282 (Ent. A) | Cl | Me | —CH₂CH₂CF₃ | 623.0 |
| 283 (Ent. B) | Cl | Me | —CH₂CH₂CF₃ | 623.0 |

EXAMPLE 284

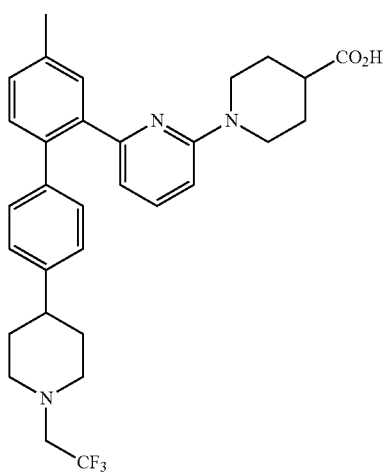 [SMILES: Cc1ccc(-c2ccc(C3CCN(CC(F)(F)F)CC3)cc2)c(-c2cccc(N3CCC(C(=O)O)CC3)n2)c1]

Step A. 4-(2'-bromo-4'-methylbiphenyl-4-yl)-1-(2,2,2-trifluoroethyl)piperidine

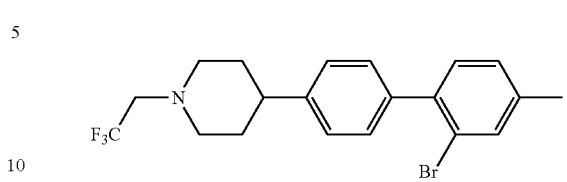

A mixture of 2-bromo-1-iodo-4-methylbenzene (0.764 g, 2.57 mmol), the title compound from Example 60 Step B (1.00 g, 2.71 mmol), dichloro bis(triphenylphosphine)palladium(II) (0.095 g, 0.135 mmol), sodium carbonate (5.42 mL of 1 M solution, 5.42 mmol) and MeCN (5.42 mL) was heated at 110° C. overnight. Organic layer was separated. Aqueous layer was extracted with hexanes-EtOAc. The organic layers were combined and concentrated. Silica gel flash chromatography eluting with hexanes:EtOAc (20:1 to 9:1 v/v) gave the title compound: LCMS m/z 414.0 [M+H⁺]; ¹H NMR (500 MHz, CDCl₃) δ 7.54 (s, 1 H),7.40 (d, J=8.1 Hz, 2 H), 7.31 (d, J=8.1 Hz, 2 H),7.26 (d, J=7.8 Hz, 1 H),7.20 (d, J=7.8 Hz, 1 H),3.16 (m, 2 H), 3.08 (q, J=9.8 Hz, 2 H),2.57 (m, 3 H),2.42 (s, 3 H).1.95-1.88 (m, 4 H).

Step B. 4-[4'-methyl-2'-(4,4,55-tetramethyl-1,3,2-dioxaborolan-2-yl)biphenyl-4-yl]-1-(2,2,2-trifluoroethyl)piperidine To a flask containing the title compound from the above Step A (0.6 g, 1.45 mmol), 1,1 bis(di-tert-butylphosphino)ferrocene palladium dichloride (50 mg, 0.077 mmol), bis(pinacolato)diboron (1.11 g, 4.4 mmol), and KOAc (0.568 g, 5.8 mmol) was added 1,4-dioxane (10 mL). The reaction mixture was stirred under nitrogen at 120° C. for 3 h. The reaction mixture was then cooled to ambient temperature, diluted with hexanes, and passed through a pad of silica gel, eluted by 20% EtOAc in hexanes. Concentration of the filtrate, followed by purification by flash chromatography on silica gel (5% then 15% EtOAc in hexanes) provided the title compound. LCMS m/z 460.2 [M+H]⁺. ¹H NMR (500 MHz, CDCl₃) δ 7.55 (s, 1 H),7.36 (d, J=8.0 Hz, 2 H),7.32 (d, J=8.0 Hz, 1 H),7.29 (d, J=7.7 Hz, 1 H),7.25 (d, J=8.0 Hz, 2 H), 3.16 (m, 2 H),3.08 (q, J=9.7 Hz, 2 H),2.55 (m, 3 H),2.43 (s, 3 H).1.95-1.84 (m, 4H), 133-1.23 (s, 12 H).

Step C. 2-bromo-6-{4-methyl-4'-[1-(2,2,2-trifluoro-ethyl)piperidin-4-yl]biphenyl-2-yl}pyridine

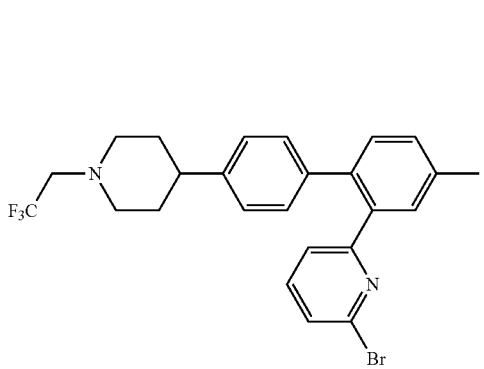 [SMILES: Cc1ccc(-c2ccc(C3CCN(CC(F)(F)F)CC3)cc2)c(-c2cccc(Br)n2)c1]

The title compound from the Step C above (150 mg, 0.33 mmol), 2,6-dibromopyridine (77 mg, 0.33 mmol), dichloro bis(triphenylphosphine)palladium(II) (23 mg, 0.033 mmol), sodium carbonate (0.653 mL of 1 M solution, 0.653 mmol) and MeCN (1.5 mL) were mixed in a sealed vial under nitrogen and heated at 90° C. for 4 h. Organic layer was separated. Aqueous layer was extracted with hexanes-EtOAc. The organic layers were combined and concentrated. Silica gel flash chromatography (hexanes-DCM 4:1 to 1:1, then hexanes-EtOAc, 20:1 to 7:1 v/v) gave the title compound: LCMS m/z 491.0 [M+H]$^+$; $^1$H NMR (500 MHz, CDCl$_3$) δ 7.58 (s, 1 H), 7.38-7.28 (m, 3 H), 7.24 (t, J=7.8 Hz, 1 H), 7.17-7.10 (q, 4 H), 6.82 (d, J=7.7 Hz, 1 H), 3.13 (m, 2 H), 3.06 (q, J=9.6 Hz, 2 H), 2.52 (m, 3 H), 2.49 (s, 3 H).1.92-1.76 (m, 4 H).

Step D. 1-(6-{4-methyl-4'-[1-(2,2,2-trifluoroethyl)piperidin-4-yl]biphenyl-2-yl}pyridin-2-yl)piperidine-4-carboxylic acid A mixture of the title compound from the above Step C (40 mg, 0.082 mmol), tris(dibenzylideneacetone)dipalladium (13.2 mg, 0.014 mmol), X-Phos(2-dicyclohexylphosphino-2',4',6'-triisopropylbiphenyl) (18 mg, 0.038 mmol), potassium phosphate (40 mg, 0.189 mmol) and 1,4-dioxane (0.6 mL) was heated at 90° C. overnight. The crude reaction mixture was concentrated, passed through a silica gel plug eluting with 1:1 DCM:EtOAc, and concentrated in vacuo. Treatment with NaOH (0.3 mL of 3 N solution, 0.9 mmol) and 0.15 mL each of MeOH and 1,4-dioxane at 65° C. for 0.5 h and at r.t. overnight, followed by purification on reverse phase HPLC using an YMC C-18 column eluted by 0.1% TFA-modified acetonitrile-water (30% to 100%) gave the title compound after lyophilization. LCMS m/z 538.3 [M+H]$^+$. $^1$H NMR (500 MHz, CD$_3$CN) δ 7.94 (dd, J=9.3, 7.3 Hz, 1 H), 7.51-7.42 (m, 3 H), 7.25 (d, J=8.2 Hz, 2 H), 7.20 (d, J=8.2 Hz, 2 H), 7.04 (d, J=9.3 Hz, 1 H), 6.99 (d, J=7.3 Hz, 1 H), 3.77 (q, J=9.5 Hz, 2 H), 3.55 (d, J=11.9 Hz, 2 H), 3.49 (m, 2 H), 3.10-2.95 (m, 4 H), 2.81 (m, 1 H), 2.60 (m, 1 H), 2.48 (s, 3 H), 2.20 (m, 4 H), 1.86 (m, 2 H), 1.45 (m, 2 H).

EXAMPLE 285

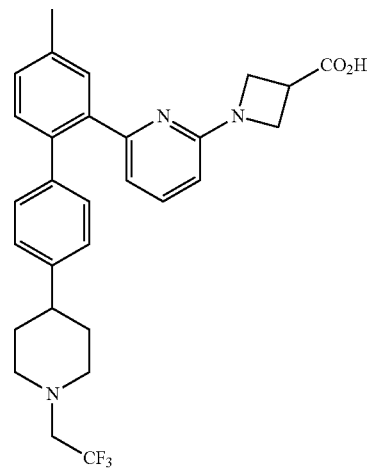 [SMILES: Cc1ccc(-c2ccc(C3CCN(CC(F)(F)F)CC3)cc2)c(-c2cccc(N3CC(C(=O)O)C3)n2)c1]

Step A. 2-fluoro-6-{4-methyl-4'-[1-(2,2,2-trifluoroethyl)piperidin-4-yl]biphenyl-2-yl}pyridine

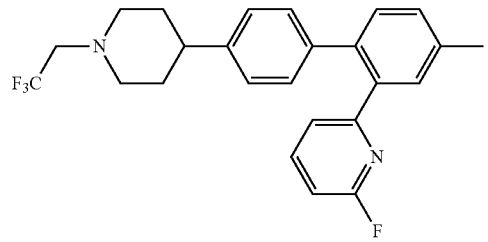 [SMILES: Cc1ccc(-c2ccc(C3CCN(CC(F)(F)F)CC3)cc2)c(-c2cccc(F)n2)c1]

The title compound from Example 284 Step B (150 mg, 0.33 mmol), 2-chloro-6-fluoropyridine (43 mg, 0.33 mmol), dichloro bis(triphenylphosphine)palladium(II) (23 mg, 0.033 mmol), sodium carbonate (0.653 mL of a 1 M aq. solution, 0.653 mmol) and MeCN (1.5 mL) were mixed in a sealed vial under nitrogen and heated at 90° C. for 4 h. Organic layer was separated. Aqueous layer was extracted with hexanes-EtOAc. The organic layers were combined and concentrated. Silica gel flash chromatography (4:1 to 1:1 hexanes-DCM, then 20:1 to 7:1 hexanes-EtOAc, v/v) gave the title compound: LCMS m/z 429.3 [M+H]$^+$; $^1$H NMR (500 MHz, CDCl$_3$) δ 7.57 (s, 1 H), 7.47 (dd, J=8.0, 8.0 Hz, 1 H), 7.36 (d, J=7.8 Hz, 1 H), 7.32 (d, J=8.7 Hz, 1 H), 7.16-7.11 (m, 4 H), 6.77 (m, 2 H), 3.12 (m, 2 H), 3.06 (q, J=9.7 Hz, 2 H), 2.52 (m, 3 H), 2.49 (s, 3 H).1.89-1.78 (m, 4 H).

Step B. 1-(6-{4-methyl-4'-[1-(2,2,2-trifluoroethyl)piperidin-4-yl]biphenyl-2-yl}pyridin-2-yl)azetidine-3-carboxylic acid A mixture of the title compound from the above Step A (7.7 mg, 0.018 mmol), azetidine-3-carboxylic acid (3.84 mg, 0.038 mmol), cesium carbonate (29 mg, 0.089 mmol) and 0.15 mL DMF was heated at 125° C. overnight. The reaction mixture was allowed to cool to ambient temperature, and the same amounts of azetidine-3-carboxylic acid and cesium carbonate were added. The reaction mixture was heated at 160° C. for another 6 h, cooled, acidified with TFA in DMSO, and purified on a reverse phase HPLC to give the title compound after lyophilization. LCMS m/z 510.2 [M+H]+. 1H NMR (500 MHz, CD3OD) δ 7.41-7.36 (m, 2 H),7.28 (s, 2 H), 7.11 (d, J=8.1 Hz, 2 H),7.05 (d, J=8.2 Hz, 2 H),6.47 (d, J=7.3 Hz, 1 H),6.26 (d, J=8.4 Hz, 1 H),3.96 (m, 4 H),3.40 (m, 1 H),3.09 (q, 4 H),2.49 (m, 3 H),2.43 (s, 3 H),1.78 (m, 4 H).

EXAMPLE 286

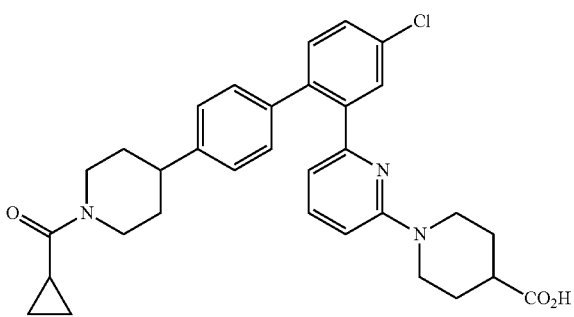 [SMILES: O=C(O)C1CCN(c2cccc(-c3cc(Cl)ccc3-c3ccc(C4CCN(C(=O)C5CC5)CC4)cc3)n2)CC1]

Step A. tert-butyl 4-(2'-bromo-4'-chlorobiphenyl-4-yl)piperidine-1-carboxylate

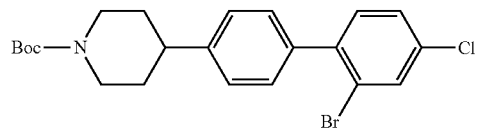

A mixture of 2-bromo-1-iodo-4-chorolbenzene (4 g, 12.6 mmol), tert-butyl 4-[4-(4,4,5,5-tetramethyl-1,3,2-dioxaborolan-2-yl)phenyl]piperidine-1-carboxylate (8.5 g, 21.9 mmol), dichloro bis(triphenylphosphine)palladium(II) (0.5 g, 0.71 mmol), sodium carbonate (20 mL of a1 M aq. solution, 20 mmol) and MeCN (100 mL) was heated at 95° C. for 14 h. Organic layer was separated. Aqueous layer was extracted with hexanes-EtOAc. The organic layers were combined and concentrated. Silica gel flash chromatography (4:1 to 2:1 to 1:1 hexanes:DCM, then 20:1 to 4:1 hexanes:EtOAc, all v/v) gave the title compound: LCMS m/z 352.2 [M-Boc+2H]+; 1H NMR (500 MHz, CDCl3) δ (ppm) 7.70 (d, 1H, J=2.1 Hz), 7.38-7.26 (m, 6 H),4.30 (broad s, 2 H),2.85 (broad s, 2 H),2.74 (m, 1 H),1.90 (d, 2H, J=13.0), 1.60 (m, 2 H),1.52 (s, 9 H).

Step B. tert-butyl 4-[4'-chloro-2'-(4,4,5,5-tetramethyl-1,3,2-dioxaborolan-2-yl)biphenyl-4-yl]piperidine-1-carboxylate

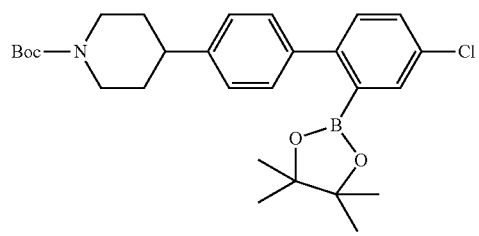 [SMILES: CC(C)(C)OC(=O)N1CCC(c2ccc(-c3ccc(Cl)cc3B3OC(C)(C)C(C)(C)O3)cc2)CC1]

To a flask containing the title compound from the above Step A (0.45 g, 1.20 mmol), 1,1 bis(di-tert-butylphosphino) ferrocene palladium dichloride (39 mg, 0.06 mmol), bis(pinacolato)diboron (0.381 g, 1.50 mmol), and KOAc (0.354 g, 3.60 mmol) was added 1,4-dioxane (8 mL). The reaction mixture was stirred under nitrogen at 90° C. for 16 h. The reaction mixture was then cooled to ambient temperature, diluted with hexanes (30 mL), and passed through a pad of silica gel, eluted by 250 mL 15% EtOAc in hexanes, and concentrated to provide a crude title compound. LCMS m/z 414.0 [M—C6H11]−.

Step C. tert-butyl 4-(4'-chloro-2'-{6-[4-(ethoxycarbonylpiperidin-1-yl]pyridin-2-yl}biphenyl-4-yl)piperidine-1-carboxylate

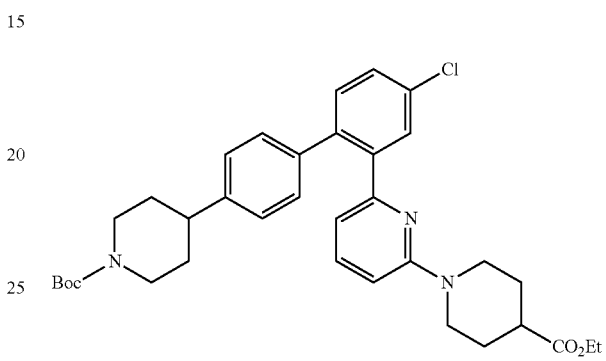

The crude product from Step 13 above (100 mg), ethyl 1-(6-chloropyridin-2-yl)piperidine-4-carboxylate (54 mg, 0.20 mmol), dichloro bis(triphenylphosphine)palladium(II) (24.6 mg, 0.035 mmol), sodium carbonate (0.30 mL of 1 M solution, 0.30 mmol) and MeCN (1.5 mL) were mixed in a sealed vial under nitrogen and heated at 65° C. for 40 h. Organic layer was separated. Aqueous layer was extracted three times with hexanes-EtOAc. The organic layers were combined and concentrated. The crude material was taken up in DMSO and purified on a reverse-phase HPLC YMC C-18 column (65% to 100% MeCN in water with 1% formic acid), and concentrated to give a crude form of the title compound. LCMS m/z 604.3 [M+H]+.

Step D. ethyl 1-[6-(4-chloro-4'-piperidin-4-ylbiphenyl-2-yl)pyridin-2-1]piperidine-4-carboxylate

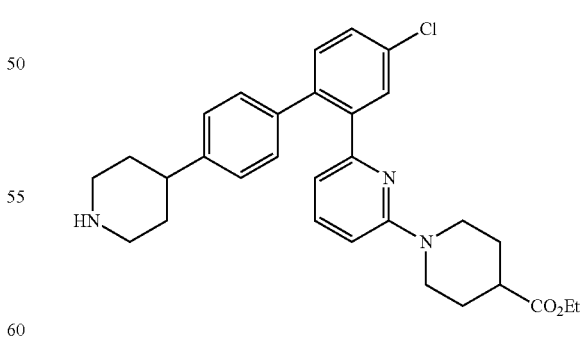

The crude material from the Step C above was further treated with 3 mL of 3:1 DCM:TFA for 20 min and the mixture was concentrated. Toluene was added and the material was concentrated again. DCM was added, followed by 2N HCl-ether. Concentration gave a crude form of the title compound. LCMS m/z 504.1 [M+H]+.

Step E. 1-(6-{4-chloro-4'-[1-(cyclopropylcarbonyl) piperidin-4-yl]biphenyl-2-yl}pyridin-2-yl)piperidine-4-carboxylic acid The crude material from the Step D above was treated with excess of cyclopropanecarbonyl chloride and N,N-diisopropylethylamine in DCM at rt for 1 h. The resulting mixture was concentrated. Treatment with NaOH (0.3 mL of 3 N solution, 0.9 mmol) and 0.15 mL each of MeOH and 1,4-dioxane at 65° C. for 0.5 h, followed by purification on reverse phase HPLC using an YMC C-18 column eluted by 0.1% TFA-modified acetonitrile in water (30% to 100%) provided the title compound. LCMS m/z 544.2 [M+H]$^+$; $^1$H NMR (500 MHz, CDCl$_3$) δ 7.73 (t, 1H, J=8.0 Hz), 7.55 (s, 1H), 7.51 (d, 1H, J=9 Hz), 7.38 (d, 1H, J=9 Hz), 7.15 (m, 4H), 6.83 (d, 1H, J=8.0), 6.75 (d, 1H, J=8.0 Hz), 4.71 (m, 1H), 4.42 (m, 1H), 3.64 (m, 2H), 3.27 (m, 1H), 3.07 (m, 2H), 2.85 (m, 1H), 2.75 (m, 1H), 2.58 (m, 1H), 2.00 (m, 2H), 1.85 (m, 4H), 1.57 (m, 1H), 1.44 (m, 2H), 1.08 (m, 2H), 0.84 (m, 2H).

The compounds in TABLE 7-10 were prepared using the chemistry described in Examples 284~286.

TABLE 7

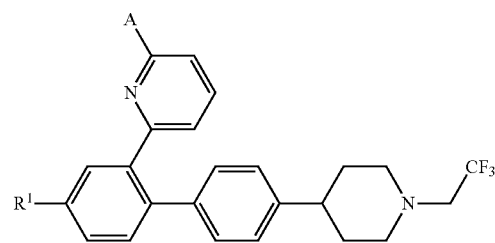

| Example | R$^1$ | A | MS [M + H]$^+$ |
|---|---|---|---|
| 287 | Me | (5-oxopyrrolidin-3-yl)-CO$_2$H | 538.2 |
| 288 | Me | (2-oxopiperidin-4-yl)-CO$_2$H | 552.2 |
| 289 (racemic) | Me | pyrrolidin-3-yl-CO$_2$H | 524.3 |
| 290 | Me | 4-methylpiperidin-4-yl-CO$_2$H | 552.3 |
| 291 | Cl | (R)-pyrrolidin-3-yl-CO$_2$H | 544.2 |

TABLE 8

| Example | R$^1$ | R$^3$ | Z | MS [M + H]$^+$ |
|---|---|---|---|---|
| 292 | Cl | H | —OMe | 534.2 |
| 293 | Cl | H | —NMe$_2$ | 547.2 |
| 294 | Cl | Me | —OMe | 548.3 |
| 295 | Cl | Me | cyclopropyl | 558.3 |
| 296 | Cl | Me | —NMe$_2$ | 561.2 |
| 297 | Me | H | —NMe$_2$ | 527.3 |
| 298 | Me | H | cyclopropyl | 524.3 |

TABLE 9

| Example | R$^1$ | R$^3$ | A | Z | MS [M + H]$^+$ |
|---|---|---|---|---|---|
| 299 | Cl | H | azetidin-3-yl-CO$_2$H | cyclopropyl | 516.2 |
| 300 | Cl | H | azetidin-3-yl-CO$_2$H | —OMe | 506.1 |
| 301 | Cl | H | azetidin-3-yl-CO$_2$H | —NMe$_2$ | 519.2 |

TABLE 9-continued

| Example | R¹ | R³ | A | Z | MS [M + H]⁺ |
|---|---|---|---|---|---|
| 302 | Me | H | azetidine-N-CO₂H | —OMe | 486.2 |
| 303 | Me | H | azetidine-N-CO₂H | cyclopropyl | 496.2 |
| 304 | Cl | Me | azetidine-N-CO₂H | cyclopropyl | 530.2 |
| 305 | Cl | Me | azetidine-N-CO₂H | —OMe | 520.2 |
| 306 | Cl | H | pyrrolidine-CO₂H | cyclopropyl | 530.3 |

TABLE 10

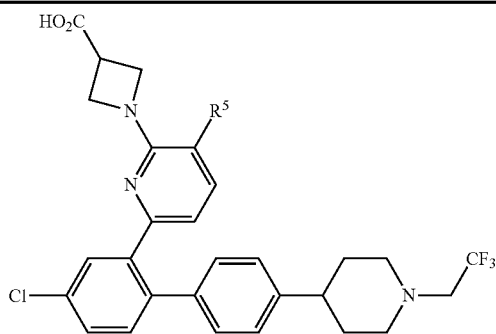

| Example | R⁵ | MS [M + H]⁺ |
|---|---|---|
| 307 | H | 530.0 |
| 308 | F | 548.1 |

Cell-based sGC Functional Assay

Methods:

A CHO-K1 cell line stably expressing the sGC α1/β1 heterodimer was generated using a standard transfection protocol. CHO-K1 cells were transfected with plasmids pIREShyghsGCα1 and pIRESneo-hsGCβ1 simultaneously using FUGENE reagent. Clones that stably express both subunits were selected with hygromycin and neomycin for ~2 weeks. Clone #7 was chosen for the assay and was designated CHO-K1/sGC. CHO-K1/sGC cells were maintained in F-K12 medium containing 10% heat-inactivated Fetal Bovine Serum (FBS), 100 µg/mL penicillin/streptomycin, 0.5 mg/mL hygromycin and 0.25 mg/mL G418. On the day of the assay, cells were harvested in EBSS (Earle's balanced salt solution) Assay Buffer (EAB) containing 5 mM $MgCl_2$, 10 mM HEPES (4-(2-hydroxyethyl)piperazine-1-ethanesulfonic acid) and 0.05% BSA (bovine serum albumin) and cell density was adjusted to 0.75–1.25×10^6 cells/ml with EAB. IBMX (3-isobutyl-1-methylxanthin, 0.5 mM) was added to inhibit degradation of cGMP. Compounds were diluted from DMSO stock solutions and added to the assay at a final DMSO concentration of 1%. Cells were incubated with compounds in the presence and absence of 10 µM of 1H-(1,2,4)oxadiazolo(4,3-a) quinoxalin-1-one (ODQ) for 1 hr at 37° C. At the end of the incubation period, the reaction was terminated and the cells were lysed. The level of intracellular cGMP was determined using an HTRF-based assay kit (Cis-Bio, 62GM2PEC), which detects the displacement of a fluorescence labeled cGMP from its specific antibody. The amount of cGMP was plotted against compound concentration in PRISM software and the inflection point (IP) and maximum fold induction over DMSO control were derived from the plot.

The compounds of the instant invention had inflection points (IP) less than or equal to 10 µM and a maximum fold induction over DMSO control of at least 4-fold in the cell based assay described above (with ODQ incubation), and more particularly less than or equal to about 200 nM/equal to or greater than about 20-fold. Preferred compounds had an IP of less than or equal to about 100 nM and a maximum fold induction over DMSO control of at least 50-fold.

Cell-based assay results (with ODQ incubation) for the following representative compounds are provided. Data are listed as inflection points (IP) and the maximal fold induction over DMSO control.

| Example # | IUPAC Name | IP (nM) (maximum fold induction) |
|---|---|---|
| 60 | 1-(6-{4-chloro-4'-[1-(2,2,2-trifluoroethyl)piperidin-4-yl]biphenyl-2-yl}pyridin-2-yl)-5-(trifluoromethyl)-1H-pyrazole-4-carboxylic acid | 14.6 nM (231-fold) |
| 61 | 1-[2'-{4-[1-(2,2,2-trifluoroethyl)piperidin-4-yl]phenyl}-5'-(trifluoromethyl)-2,3'-bipyridin-6-yl]-5-(trifluoromethyl)-1H-pyrazole-4-carboxylic acid | 16.3 nM (248-fold) |
| 89 | 1-(6-{4-methyl-4'-[1-(2,2,2-trifluoroethyl)piperidin-4-yl]biphenyl-2-yl}pyridin-2-yl)piperidine-4-carboxylic acid | 48.8 nM (166-fold) |

-continued

| Example # | IUPAC Name | IP (nM) (maximum fold induction) |
|---|---|---|
| 94 | 1-(6-{4-chloro-4'-[1-(cyclopropylcarbonyl)piperidin-4-yl]biphenyl-2-yl}pyridin-2-yl)-5-(trifluoromethyl)-1H-pyrazole-4-carboxylic acid | 30.2 nM (281-fold) |
| 127 | 1-{6-[4'-[1-(methoxycarbonyl)piperidin-4-yl]-4-(trifluoromethyl)biphenyl-2-yl]pyridin-2-yl}-5-(trifluoromethyl)-1H-pyrazole-4-carboxylic acid | 15.8 nM (119-fold) |
| 136 | 1-(6-{4-fluoro-4'-[1-(3,3,3-trifluoropropyl)piperidin-4-yl]biphenyl-2-yl}pyridin-2-yl)-5-(trifluoromethyl)-1H-pyrazole-4-carboxylic acid | 78.8 nM (162-fold) |
| 175 | 1-(6-{4-chloro-4'-[4-(2,2,2-trifluoroethyl)piperazin-1-yl]biphenyl-2-yl}pyridin-2-yl)-5-(trifluoromethyl)-1H-pyrazole-4-carboxylic acid | 9.8 nM (703-fold) |

While the invention has been described with reference to certain particular embodiments thereof, numerous alternative embodiments will be apparent to those skilled in the art from the teachings described herein. Recitation of a specific compound in the claims (i.e., a species) without a chiral designation is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound of structural Formula I:

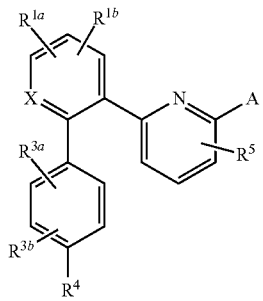

I and pharmaceutically acceptable salts thereof, wherein:
X is selected from the group consisting of CH, and $CR^2$;
$R^{1a}$ and $R^{1b}$ are independently selected from the group consisting of —H, —F, —Cl, —Br, —CN, cyclopropyl, —$C_{1-3}$alkyl optionally substituted with one to six of —F, and —O—$C_{1-3}$alkyl optionally substituted with one to six of —F;
$R^2$ is selected from the group consisting of —F, —Cl, —Br, —CN, cyclopropyl, —$C_{1-3}$alkyl optionally substituted with one to six of —F, and —O—$C_{1-3}$alkyl optionally substituted with one to six of —F;
$R^{3a}$ and $R^{3b}$ are independently selected from the group consisting of —H, —F, —Cl, —Br, —CN, —$C_{1-3}$alkyl optionally substituted with one to six of —F, and —O—$C_{1-3}$alkyl optionally substituted with one to six of —F;
A is

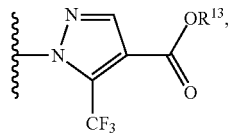

wherein $R^{13}$ is selected from the group consisting of —H and —$C_{1-6}$ alkyl;
$R^4$ is
a heterocycle selected from the group consisting of:

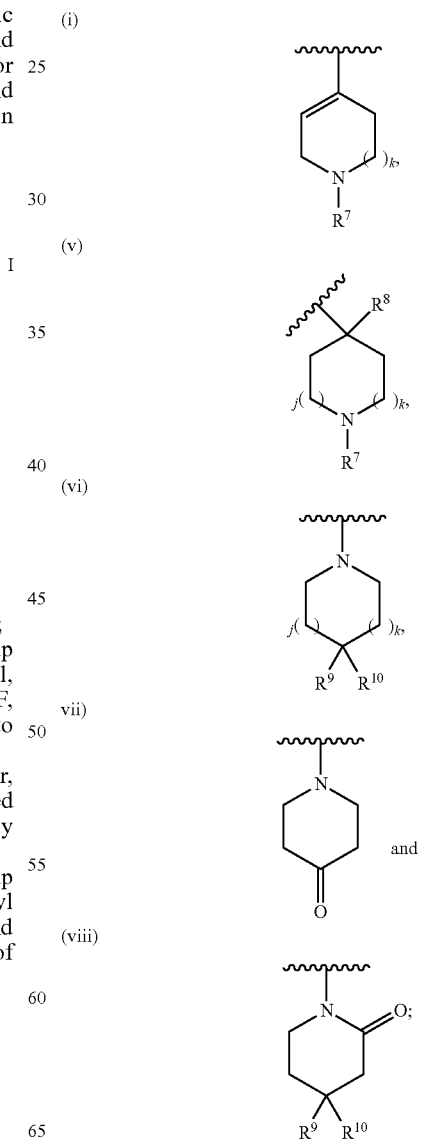

R$^5$ is selected from the group consisting of —H, —F, —OH, —CF$_3$, —OC$_{1-3}$ alkyl and —OCF$_3$;
j is an integer 1;
k is an integer 1;
R$^7$ is selected from the group consisting of (a) —H, (b) —C$_{1-6}$alkyl optionally substituted with one to six of —F, (c) —C$_{1-3}$alkyl substituted with one or two of —OCH$_3$,
(d) —(CH$_2$)$_{0-1}$—C$_{3-6}$cycloalkyl optionally substituted with (i) one to three of —F or (ii) C$_{1-3}$alkyl optionally substituted with one to three of —F, (e) 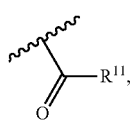

(f) 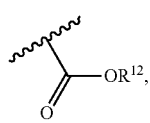

(g) 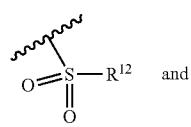

(h) 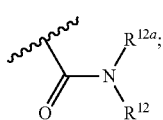

R$^8$ is selected from the group consisting of —H, —F, —OH, and —C$_{1-3}$alkyl optionally substituted with one to six of —F;
R$^9$ is selected from the group consisting of (a) —H, (b) —F, (c) —OH,
(d) —C$_{1-3}$alkyl optionally substituted with substituents selected from the group consisting of (i) —OH and (ii) one to six of —F,
(e) —C$_{3-6}$cycloalkyl optionally substituted with one to three of —F, and
(f) —O—C$_{1-3}$alkyl optionally substituted with —OH;
R$^{10}$ is selected from the group consisting of (a) —H, (b) —F, (c) —C$_{1-3}$alkyl optionally substituted with with substituents selected from (i) —OH and (ii) one to six of —F, and
(d) —O—C$_{1-3}$alkyl;
R$^{11}$ is selected from the group consisting of (a) —H, (b) —C$_{1-6}$alkyl optionally substituted with one to six of —F, (c) —C$_{3-6}$cycloalkyl optionally substituted with —CH$_3$, —CF$_3$, —CN, —OH, or —NH$_2$ or one to three of —F;
R$^{12a}$ is selected from the group consisting of (a) —H, (b) —C$_{1-6}$alkyl optionally substituted with one to six of —F, (c) —C$_{3-6}$cycloalkyl optionally substituted with —CH$_3$, —CF$_3$, —CN, —OH, or one to three of —F; and
R$^{12}$ is selected from the group consisting of (a) —C$_{1-6}$alkyl optionally substituted with one to six of —F, and (b) —C$_{3-6}$cycloalkyl optionally substituted with one to three of —F.

2. The compound of claim 1 or a pharmaceutically acceptable salt thereof wherein:
X is selected form CH and N;
A is selected from

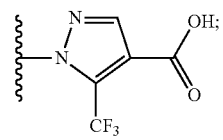 [SMILES: *n1ncc(C(=O)O)c1C(F)(F)F]

R$^{1a}$ is selected from the group consisting of —H, —Cl, —F, —CH$_3$ and —CF$_3$;
R$^{1b}$ is —H;
R$^{3a}$ and R$^{3b}$ are independently selected from the group consisting of —H, —Cl, —F, —CH$_3$, —CF$_3$, —OCH$_3$, and —OCF$_3$;
R$^4$ is
a heterocycle selected from the group consisting of:

(i) 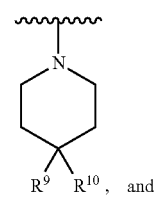

(ii) 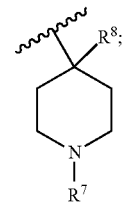

R$^5$ is —H;
R$^{6a}$ and R$^{6b}$ are each —H;
R$^7$ is selected from:
(i) —C$_{1-3}$alkyl optionally substituted with one to three of —F,
(ii) —(CH$_2$)$_{0-1}$—C$_{3-4}$cycloalkyl optionally substituted with —CF$_3$ or one to two of —F,
(iii) —C(=O)—C$_{3-4}$cycloalkyl optionally substituted with —CH$_3$, —CF$_3$, —CN, —OH, or —NH$_2$ or one to three of —F,
(iv) —C(=O) OC$_{1-3}$alkyl optionally substituted with one to three of —F,
(v) —C(=O)—N(C$_{1-3}$alkyl)$_2$, and
(vi) —SO$_2$—R$^{12}$ wherein R$^{12}$ is —C$_{1-3}$alkyl or cyclopropyl and R$^{12}$ is optionally substituted with one to three of —F;
R$^8$ is selected from —H, —F and —OH;
R$^9$ is selected from (i) cyclopropyl optionally substituted with one or two of —F and (ii) —C$_{1-3}$alkyl optionally substituted with one to three of —F;
R$^{10}$ is H;
R$^{11}$ is selected from —C$_{1-3}$alkyl and —C$_{3-6}$cycloalkyl wherein R$^{11}$ is optionally substituted with —CH$_3$, —CF$_3$, —CN, —OH, or —NH$_2$ or one to three of —F;

$R^{12a}$ is selected from the group consisting of —H and —$C_{1-3}$alkyl;

$R^{12}$ is selected from —$C_{1-3}$alkyl and cyclopropyl wherein $R^{12}$ is optionally substituted with one to three of —F; and $R^{13}$ is —H.

3. The compound of claim 1 or a pharmaceutically acceptable salt thereof wherein:

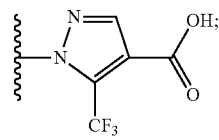 [SMILES: *n1ncc(C(=O)O)c1C(F)(F)F]

A is $R^4$ is selected from the group consisting of:

(i)

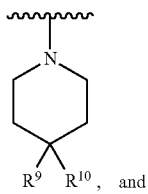

and (ii)

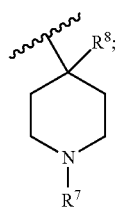

and $R^5$ is —H.

4. The compound of claim 1 selected form the group goup consisting of:

1-{6-[4-chloro-4'-(4-cyclopropylpiperidin-1-yl)biphenyl-2-yl]pyridin-2-yl}-5-(trifluoromethyl)-1H-pyrazole-4-carboxylic acid;

1-{6-[4'-(4-cyclopropylpiperidin-1-yl)-4-methylbiphenyl-2-yl]pyridin-2-yl}-5-(trifluoromethyl)-1H-pyrazole-4-carboxylic acid;

1-(6-{4-chloro-4'-[1-(2,2,2-trifluoroethyl)piperidin-4-yl]biphenyl-2-yl}pyridin-2-yl)-5-(trifluoromethyl)-1-pyrazole-4-carboxylic acid;

1-(2'-{4-[1-(2,2,2-trifluoroethyl)piperidin-4-yl]phenyl}-5'-(trifluoromethyl)-2,3'-bipyridin-6-yl]-5-(trifluoromethyl)-1H-pyrazole-4-carboxylic acid;

1-(6-{4-chloro-4'-[1-(methoxycarbonyl)piperidin-4-yl]biphenyl-2-yl}pyridin-2-yl)-5-(trifluoromethyl)-1H-pyrazole-4-carboxylic acid;

1-(6-{4-chloro-4'-[1-(ethoxycarbonyl)piperidin-4-yl]biphenyl-2-yl}pyridin-2-yl)-5-(trifluoromethyl)-1H-pyrazole-4-carboxylic acid;

1-(6-{4-chloro-4'-[1-(dimethylcarbamoyl)piperidin-4-yl]-3'-methylbiphenyl-2-yl}pyridin-2-yl)-5-(trifluoromethyl)-1H-pyrazole-4-carboxylic acid;

1-(6-{4-fluoro-4'-[1-(2,2,2-trifluoroethyl)piperidin-4-yl]biphenyl-2-yl}pyridin-2-yl)-5-(trifluoromethyl)-1H-pyrazole-4-carboxylic acid;

1-(6-{3'4-difluoro-4'-[1-(2,2,2-trifluoroethyl)piperidin-4-yl]biphenyl-2-yl}pyridin-2-yl)-5-(trifluoromethyl)-1H-pyrazole-4-carboxylic acid;

1-(6-{4-fluoro-4'-[1-(3,3,3-trifluoropropyl)piperidin-4-yl]biphenyl-2-yl}pyridin-2-yl)-5-(trifluoromethyl)-1H-pyrazole-4-carboxylic acid;

1-(6-{4-fluoro-3'-methyl-4'-[1-(2,2,2-trifluoroethyl)piperidin-4-yl]biphenyl-2-yl}pyridin-2-yl)-5-(trifluoromethyl)-1H-pyrazole-4-carboxylic acid; and 1-(5'-chloro-2'-{3-methyl-4-[1-(2,2,2-trifluoroethyl)piperidin-4-yl]phenyl}-2,3'-bipyridin-6-yl)-5-(trifluoromethyl)-1H-pyrazole-4-carboxylic acid; and the pharmaceutically acceptable salts thereof.

5. A pharmaceutical composition comprised of a compound of claim 1 and a pharmaceutically acceptable carrier.

* * * * *